US009574241B2

(12) United States Patent
Ferrando et al.

(10) Patent No.: US 9,574,241 B2
(45) Date of Patent: Feb. 21, 2017

(54) RECURRENT MUTATIONS IN EPIGENETIC REGULATORS, *RHOA* AND *FYN* KINASE IN PERIPHERAL T-CELL LYMPHOMAS

(71) Applicant: THE TRUSTEES OF COLUMBIA UNIVERSITY IN THE CITY OF NEW YORK, New York, NY (US)

(72) Inventors: Adolfo Ferrando, New York, NY (US); Raul Rabadan, New York, NY (US); Teresa Palomero, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 14/895,287

(22) PCT Filed: Jun. 3, 2014

(86) PCT No.: PCT/US2014/040647
§ 371 (c)(1),
(2) Date: Dec. 2, 2015

(87) PCT Pub. No.: WO2014/197453
PCT Pub. Date: Dec. 11, 2014

(65) Prior Publication Data

US 2016/0102367 A1 Apr. 14, 2016

Related U.S. Application Data

(60) Provisional application No. 61/830,631, filed on Jun. 3, 2013.

(51) Int. Cl.

| | |
|---|---|
| ***A61K 31/497*** | (2006.01) |
| ***C12Q 1/68*** | (2006.01) |
| ***A61K 31/506*** | (2006.01) |

(52) U.S. Cl.
CPC .......... *C12Q 1/6886* (2013.01); *A61K 31/506* (2013.01); *C12Q 2600/156* (2013.01)

(58) Field of Classification Search
CPC .................................................... C12Q 1/6886
See application file for complete search history.

(56) References Cited

U.S. PATENT DOCUMENTS

2016/0076107 A1* 3/2016 Chiba .................. C12Q 1/6886 506/9

FOREIGN PATENT DOCUMENTS

| | | |
|---|---|---|
| WO | 2012170711 | 12/2012 |
| WO | 2013071410 | 5/2013 |

OTHER PUBLICATIONS

Armitage, 2012, Am.J.Hematol, 87, 511-9.*
Biseg et al., "New Biomarkers in T-Cell Lymphomas", Mar. 1, 2012, pp. 13-28, vol. 25, No. 1, Publisher: Best Practice & Research Clinical Haematology, Published in: http://www.ncbi.nlm.nih.gov/pubmed/22409820.
Sakata-Yanagimoto et al., "Somatic RHOA Mutation in Angioimmunoblastic T Cell Lymphoma", Jan. 12, 2014, pp. 171-175, vol. 46, Publisher: Nature Genetics, Published in: http://www.ncbi.nlm.nih.gov/pubmed/24413737.
Palomero et al., "Recurrent Mutations in Epigenetic Regulators, RHOA and FYN Kinase in Peripheral T Cell Lymphomas", Jan. 12, 2014, pp. 166-170, vol. 46, Publisher: Nature Genetics, Published in: http://www.ncbi.nlm.nih.gov/pubmed/24413734.
ISA/US, "International Search Report and Written Opinion for the corresponding PCT application US2014/040647", Oct. 24, 2014, pp. 1-7.

* cited by examiner

*Primary Examiner* — Nizal Chandrakumar
(74) *Attorney, Agent, or Firm* — Judith A. Evans; Beusse Wolter Sanks & Maire

(57) ABSTRACT

Whole exome sequencing of 12 tumor-normal DNA pairs, RNAseq analysis and targeted deep sequencing identified new genetic alterations in PTCL transformation. These analyses identified highly recurrent epigenetic factor mutations in TET2, DN-MT3A and IDH2 as well as a new highly prevalent RHOA p.Gly17Val (NM_001664) mutation present in 22/35 (67%) of angioimmunoblastic T-cell lymphomas (AITL) and in 8/44 (18%) not otherwise specified PTCL (PTCL NOS) samples. Mechanistically, the RHOA Gly17Val protein interferes with RHOA signaling in biochemical and cellular assays, an effect potentially mediated by the sequestration of activated Guanine Exchange Factor (GEF) proteins. In addition, new and recurrent, genetic defects are described including mutations in FYN, ATM, B2M and CD58 implicating SRC signaling, impaired DNA damage response and escape from immune surveillance mechanisms in the pathogenesis of PTCL.

5 Claims, 9 Drawing Sheets

SEQUENCE LISTING

<160> NUMBER OF SEQ ID NOS: 386

<210> SEQ ID NO 1
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: FYN biotinylated peptide

<400> SEQUENCE: 1

Thr Glu Pro Gln Tyr Gln Pro Gly Glu Asn Leu
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: FYN biotinylated peptide
<220> FEATURE:
<221> NAME/KEY: misc_feature
<222> LOCATION: (5)..(5)
<223> OTHER INFORMATION: pY531

<400> SEQUENCE: 2

Thr Glu Pro Gln Tyr Gln Pro Gly Glu Asn Leu
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: FYN biotinylated peptide

<400> SEQUENCE: 3

Thr Glu Pro Gln His Gln Pro Gly Glu Asn Leu
1               5                   10

<210> SEQ ID NO 4
<211> LENGTH: 12
<212> TYPE: DNA
<213> ORGANISM: Artificial Sequence
<220> FEATURE:
<223> OTHER INFORMATION: Synthetic primer

<400> SEQUENCE: 4
tgggtgggct gc                                                          12

<210> SEQ ID NO 5
<211> LENGTH: 11
<212> TYPE: DNA
<213> ORGANISM: Artificial Sequence
<220> FEATURE:
<223> OTHER INFORMATION: Synthetic primer

<400> SEQUENCE: 5
cgcatcgcgc t 11

<210> SEQ ID NO 6
<211> LENGTH: 11
<212> TYPE: DNA
<213> ORGANISM: Artificial Sequence
<220> FEATURE:
<223> OTHER INFORMATION: Synthetic primer

<400> SEQUENCE: 6
gcgcactgcc a 11

<210> SEQ ID NO 7
<211> LENGTH: 34
<212> TYPE: DNA
<213> ORGANISM: Artificial Sequence
<220> FEATURE:
<223> OTHER INFORMATION: Synthetic primer

<400> SEQUENCE: 7
gtaggtttgg gaaaagttct taagttctga aacg 34

<210> SEQ ID NO 8
<211> LENGTH: 14
<212> TYPE: DNA
<213> ORGANISM: Artificial Sequence
<220> FEATURE:
<223> OTHER INFORMATION: Synthetic primer

<400> SEQUENCE: 8
ggggggtaac aagg 14

<210> SEQ ID NO 9
<211> LENGTH: 18
<212> TYPE: DNA
<213> ORGANISM: Artificial Sequence
<220> FEATURE:
<223> OTHER INFORMATION: Synthetic primer

<400> SEQUENCE: 9
acagggctct ccctctcc 18

<210> SEQ ID NO 10
<211> LENGTH: 23
<212> TYPE: DNA
<213> ORGANISM: Artificial Sequence
<220> FEATURE:
<223> OTHER INFORMATION: Synthetic primer

<400> SEQUENCE: 10
ataattcctt ccccaaagcc cag 23

<210> SEQ ID NO 11
<211> LENGTH: 23
<212> TYPE: DNA
<213> ORGANISM: Artificial Sequence
<220> FEATURE:
<223> OTHER INFORMATION: Synthetic primer -continued

<400> SEQUENCE: 11
cccatcactt ctggttttcc agt 23

<210> SEQ ID NO 12
<211> LENGTH: 17
<212> TYPE: DNA
<213> ORGANISM: Artificial Sequence
<220> FEATURE:
<223> OTHER INFORMATION: Synthetic primer

<400> SEQUENCE: 12
gtggcttggg ctgggag 17

<210> SEQ ID NO 13
<211> LENGTH: 21
<212> TYPE: DNA
<213> ORGANISM: Artificial Sequence
<220> FEATURE:
<223> OTHER INFORMATION: Synthetic primer

<400> SEQUENCE: 13
atggagagag gagagcagga c 21

<210> SEQ ID NO 14
<211> LENGTH: 19
<212> TYPE: DNA
<213> ORGANISM: Artificial Sequence
<220> FEATURE:
<223> OTHER INFORMATION: Synthetic primer

<400> SEQUENCE: 14
gcatccccca ctgtggcta 19

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
gcctcacctc ccttttccag 20

<210> SEQ ID NO 16
<211> LENGTH: 23
<212> TYPE: DNA
<213> ORGANISM: Artificial Sequence
<220> FEATURE:
<223> OTHER INFORMATION: Synthetic primer

<400> SEQUENCE: 16
accctaatgc cctaatgtct gtc 23

<210> SEQ ID NO 17
<211> LENGTH: 20
<212> TYPE: DNA
<213> ORGANISM: Artificial Sequence
<220> FEATURE:
<223> OTHER INFORMATION: Synthetic primer

<400> SEQUENCE: 17
cgtgtgtgtt gtgtgtgtgc 20

<210> SEQ ID NO 18
<211> LENGTH: 18

-continued

<212> TYPE: DNA
<213> ORGANISM: Artificial Sequence
<220> FEATURE:
<223> OTHER INFORMATION: Synthetic primer

<400> SEQUENCE: 18
gctgggatcc acctctgg 18

<210> SEQ ID NO 19
<211> LENGTH: 21
<212> TYPE: DNA
<213> ORGANISM: Artificial Sequence
<220> FEATURE:
<223> OTHER INFORMATION: Synthetic primer

<400> SEQUENCE: 19
ttagggccag aaggctggaa g 21

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
ctgtcctgac aaccccaacc 20

<210> SEQ ID NO 21
<211> LENGTH: 22
<212> TYPE: DNA
<213> ORGANISM: Artificial Sequence
<220> FEATURE:
<223> OTHER INFORMATION: Synthetic primer

<400> SEQUENCE: 21
ctcgtactct ggctcgtcat cg 22

<210> SEQ ID NO 22
<211> LENGTH: 23
<212> TYPE: DNA
<213> ORGANISM: Artificial Sequence
<220> FEATURE:
<223> OTHER INFORMATION: Synthetic primer

<400> SEQUENCE: 22
gcaggaatga atgctgtgga aga 23

<210> SEQ ID NO 23
<211> LENGTH: 19
<212> TYPE: DNA
<213> ORGANISM: Artificial Sequence
<220> FEATURE:
<223> OTHER INFORMATION: Synthetic primer

<400> SEQUENCE: 23
cagccctggt gtggatctg 19

<210> SEQ ID NO 24
<211> LENGTH: 22
<212> TYPE: DNA
<213> ORGANISM: Artificial Sequence
<220> FEATURE:
<223> OTHER INFORMATION: Synthetic primer

<400> SEQUENCE: 24
gatgagagtg acactgccaa gg 22

<210> SEQ ID NO 25
<211> LENGTH: 23
<212> TYPE: DNA
<213> ORGANISM: Artificial Sequence
<220> FEATURE:
<223> OTHER INFORMATION: Synthetic primer

<400> SEQUENCE: 25
attagcgaag aacatctgga gcc 23

<210> SEQ ID NO 26
<211> LENGTH: 20
<212> TYPE: DNA
<213> ORGANISM: Artificial Sequence
<220> FEATURE:
<223> OTHER INFORMATION: Synthetic primer

<400> SEQUENCE: 26
ctcctctgct cactgggtct 20

<210> SEQ ID NO 27
<211> LENGTH: 22
<212> TYPE: DNA
<213> ORGANISM: Artificial Sequence
<220> FEATURE:
<223> OTHER INFORMATION: Synthetic primer

<400> SEQUENCE: 27
cagccatttt ccactgctct tg 22

<210> SEQ ID NO 28
<211> LENGTH: 22
<212> TYPE: DNA
<213> ORGANISM: Artificial Sequence
<220> FEATURE:
<223> OTHER INFORMATION: Synthetic primer

<400> SEQUENCE: 28
tgatctccaa gtccccatcc at 22

<210> SEQ ID NO 29
<211> LENGTH: 20
<212> TYPE: DNA
<213> ORGANISM: Artificial Sequence
<220> FEATURE:
<223> OTHER INFORMATION: Synthetic primer

<400> SEQUENCE: 29
ctggagagcc aagtccctga 20

<210> SEQ ID NO 30
<211> LENGTH: 18
<212> TYPE: DNA
<213> ORGANISM: Artificial Sequence
<220> FEATURE:
<223> OTHER INFORMATION: Synthetic primer

<400> SEQUENCE: 30
ccagcagagg gagagggt 18

<210> SEQ ID NO 31
<211> LENGTH: 22
<212> TYPE: DNA
<213> ORGANISM: Artificial Sequence
<220> FEATURE:
<223> OTHER INFORMATION: Synthetic primer

<400> SEQUENCE: 31
ccagctaagg agaccactgg ag 22

<210> SEQ ID NO 32
<211> LENGTH: 21
<212> TYPE: DNA
<213> ORGANISM: Artificial Sequence
<220> FEATURE:
<223> OTHER INFORMATION: Synthetic primer

<400> SEQUENCE: 32
cctggtggtt tctgaccctt c 21

<210> SEQ ID NO 33
<211> LENGTH: 23
<212> TYPE: DNA
<213> ORGANISM: Artificial Sequence
<220> FEATURE:
<223> OTHER INFORMATION: Synthetic primer

<400> SEQUENCE: 33
agatgtccct cttgtcacta acg 23

<210> SEQ ID NO 34
<211> LENGTH: 22
<212> TYPE: DNA
<213> ORGANISM: Artificial Sequence
<220> FEATURE:
<223> OTHER INFORMATION: Synthetic primer

<400> SEQUENCE: 34
cacaccactg tcctatgcag ac 22

<210> SEQ ID NO 35
<211> LENGTH: 23
<212> TYPE: DNA
<213> ORGANISM: Artificial Sequence
<220> FEATURE:
<223> OTHER INFORMATION: Synthetic primer

<400> SEQUENCE: 35
cagggcagaa atatccaagg agg 23

<210> SEQ ID NO 36
<211> LENGTH: 21
<212> TYPE: DNA
<213> ORGANISM: Artificial Sequence
<220> FEATURE:
<223> OTHER INFORMATION: Synthetic primer

<400> SEQUENCE: 36
gcccatcacg ttgcctttat c 21

<210> SEQ ID NO 37
<211> LENGTH: 20
<212> TYPE: DNA
<213> ORGANISM: Artificial Sequence
<220> FEATURE:
<223> OTHER INFORMATION: Synthetic primer

<400> SEQUENCE: 37
ctctgcaagg ggaggagagc 20

-continued

<210> SEQ ID NO 38
<211> LENGTH: 18
<212> TYPE: DNA
<213> ORGANISM: Artificial Sequence
<220> FEATURE:
<223> OTHER INFORMATION: Synthetic primer

<400> SEQUENCE: 38
cagctgccta cgcaccac 18

<210> SEQ ID NO 39
<211> LENGTH: 23
<212> TYPE: DNA
<213> ORGANISM: Artificial Sequence
<220> FEATURE:
<223> OTHER INFORMATION: Synthetic primer

<400> SEQUENCE: 39
tggacataca tgcttctgtg tga 23

<210> SEQ ID NO 40
<211> LENGTH: 21
<212> TYPE: DNA
<213> ORGANISM: Artificial Sequence
<220> FEATURE:
<223> OTHER INFORMATION: Synthetic primer

<400> SEQUENCE: 40
ggagatggct ccaagtaacg g 21

<210> SEQ ID NO 41
<211> LENGTH: 23
<212> TYPE: DNA
<213> ORGANISM: Artificial Sequence
<220> FEATURE:
<223> OTHER INFORMATION: Synthetic primer

<400> SEQUENCE: 41
taccactgag aatttgccgt ctc 23

<210> SEQ ID NO 42
<211> LENGTH: 24
<212> TYPE: DNA
<213> ORGANISM: Artificial Sequence
<220> FEATURE:
<223> OTHER INFORMATION: Synthetic primer

<400> SEQUENCE: 42
gtgtaatgat ttctgctcct tggg 24

<210> SEQ ID NO 43
<211> LENGTH: 23
<212> TYPE: DNA
<213> ORGANISM: Artificial Sequence
<220> FEATURE:
<223> OTHER INFORMATION: Synthetic primer

<400> SEQUENCE: 43
ttcctaagtg cctctgctac tct 23

<210> SEQ ID NO 44
<211> LENGTH: 18
<212> TYPE: DNA
<213> ORGANISM: Artificial Sequence
<220> FEATURE:
<223> OTHER INFORMATION: Synthetic primer -continued

<400> SEQUENCE: 44
aggaggcctg catccgag 18

<210> SEQ ID NO 45
<211> LENGTH: 21
<212> TYPE: DNA
<213> ORGANISM: Artificial Sequence
<220> FEATURE:
<223> OTHER INFORMATION: Synthetic primer

<400> SEQUENCE: 45
gtggacacag tcagccagaa g 21

<210> SEQ ID NO 46
<211> LENGTH: 20
<212> TYPE: DNA
<213> ORGANISM: Artificial Sequence
<220> FEATURE:
<223> OTHER INFORMATION: Synthetic primer

<400> SEQUENCE: 46
ggtactcacc ccatcccctc 20

<210> SEQ ID NO 47
<211> LENGTH: 19
<212> TYPE: DNA
<213> ORGANISM: Artificial Sequence
<220> FEATURE:
<223> OTHER INFORMATION: Synthetic primer

<400> SEQUENCE: 47
acttccaggc ctcctagtg 19

<210> SEQ ID NO 48
<211> LENGTH: 16
<212> TYPE: DNA
<213> ORGANISM: Artificial Sequence
<220> FEATURE:
<223> OTHER INFORMATION: Synthetic primer

<400> SEQUENCE: 48
gcttgtcccc ccaggt 16

<210> SEQ ID NO 49
<211> LENGTH: 23
<212> TYPE: DNA
<213> ORGANISM: Artificial Sequence
<220> FEATURE:
<223> OTHER INFORMATION: Synthetic primer

<400> SEQUENCE: 49
aacaaaatga aaggaggcaa ggg 23

<210> SEQ ID NO 50
<211> LENGTH: 20
<212> TYPE: DNA
<213> ORGANISM: Artificial Sequence
<220> FEATURE:
<223> OTHER INFORMATION: Synthetic primer

<400> SEQUENCE: 50
ctcggaggtg tgtgaggact 20

<210> SEQ ID NO 51

```
<211> LENGTH: 18
<212> TYPE: DNA
<213> ORGANISM: Artificial Sequence
<220> FEATURE:
<223> OTHER INFORMATION: Synthetic primer

<400> SEQUENCE: 51

ctcaggcccc acaaccaa                                                   18

<210> SEQ ID NO 52
<211> LENGTH: 23
<212> TYPE: DNA
<213> ORGANISM: Artificial Sequence
<220> FEATURE:
<223> OTHER INFORMATION: Synthetic primer

<400> SEQUENCE: 52

attaaggaag acccctggaa ctg                                             23

<210> SEQ ID NO 53
<211> LENGTH: 19
<212> TYPE: DNA
<213> ORGANISM: Artificial Sequence
<220> FEATURE:
<223> OTHER INFORMATION: Synthetic primer

<400> SEQUENCE: 53

ggtggaacgc actgcaaaa                                                  19

<210> SEQ ID NO 54
<211> LENGTH: 23
<212> TYPE: DNA
<213> ORGANISM: Artificial Sequence
<220> FEATURE:
<223> OTHER INFORMATION: Synthetic primer

<400> SEQUENCE: 54

tatcactgta tctggtcccc tcc                                             23

<210> SEQ ID NO 55
<211> LENGTH: 18
<212> TYPE: DNA
<213> ORGANISM: Artificial Sequence
<220> FEATURE:
<223> OTHER INFORMATION: Synthetic primer

<400> SEQUENCE: 55

cagggctccc ctcctctg                                                   18

<210> SEQ ID NO 56
<211> LENGTH: 23
<212> TYPE: DNA
<213> ORGANISM: Artificial Sequence
<220> FEATURE:
<223> OTHER INFORMATION: Synthetic primer

<400> SEQUENCE: 56

accctcctct tgtgtatctt tct                                             23

<210> SEQ ID NO 57
<211> LENGTH: 21
<212> TYPE: DNA
<213> ORGANISM: Artificial Sequence
<220> FEATURE:
<223> OTHER INFORMATION: Synthetic primer

<400> SEQUENCE: 57
```

ggatcaagaa ccttccccca c 21

<210> SEQ ID NO 58
<211> LENGTH: 19
<212> TYPE: DNA
<213> ORGANISM: Artificial Sequence
<220> FEATURE:
<223> OTHER INFORMATION: Synthetic primer

<400> SEQUENCE: 58
ggaaactgcg gggcttctc 19

<210> SEQ ID NO 59
<211> LENGTH: 23
<212> TYPE: DNA
<213> ORGANISM: Artificial Sequence
<220> FEATURE:
<223> OTHER INFORMATION: Synthetic primer

<400> SEQUENCE: 59
catttcgttt tgccagagtt gcc 23

<210> SEQ ID NO 60
<211> LENGTH: 22
<212> TYPE: DNA
<213> ORGANISM: Artificial Sequence
<220> FEATURE:
<223> OTHER INFORMATION: Synthetic primer

<400> SEQUENCE: 60
catctgacct gttgtgctca ct 22

<210> SEQ ID NO 61
<211> LENGTH: 21
<212> TYPE: DNA
<213> ORGANISM: Artificial Sequence
<220> FEATURE:
<223> OTHER INFORMATION: Synthetic primer

<400> SEQUENCE: 61
ctcatcctgc ccttccttct c 21

<210> SEQ ID NO 62
<211> LENGTH: 23
<212> TYPE: DNA
<213> ORGANISM: Artificial Sequence
<220> FEATURE:
<223> OTHER INFORMATION: Synthetic primer

<400> SEQUENCE: 62
cgctgttatc caggtttctg ttg 23

<210> SEQ ID NO 63
<211> LENGTH: 24
<212> TYPE: DNA
<213> ORGANISM: Artificial Sequence
<220> FEATURE:
<223> OTHER INFORMATION: Synthetic primer

<400> SEQUENCE: 63
ccacagaggg atgtgtaaag aagg 24

<210> SEQ ID NO 64
<211> LENGTH: 23
<212> TYPE: DNA

<213> ORGANISM: Artificial Sequence
<220> FEATURE:
<223> OTHER INFORMATION: Synthetic primer

<400> SEQUENCE: 64
gaactggtcc ctttgttctt ccc 23

<210> SEQ ID NO 65
<211> LENGTH: 23
<212> TYPE: DNA
<213> ORGANISM: Artificial Sequence
<220> FEATURE:
<223> OTHER INFORMATION: Synthetic primer

<400> SEQUENCE: 65
tgtgcgctca tcaataatct cct 23

<210> SEQ ID NO 66
<211> LENGTH: 23
<212> TYPE: DNA
<213> ORGANISM: Artificial Sequence
<220> FEATURE:
<223> OTHER INFORMATION: Synthetic primer

<400> SEQUENCE: 66
ctgtcagcct gtaactgacc ttg 23

<210> SEQ ID NO 67
<211> LENGTH: 20
<212> TYPE: DNA
<213> ORGANISM: Artificial Sequence
<220> FEATURE:
<223> OTHER INFORMATION: Synthetic primer

<400> SEQUENCE: 67
ctcaggggct tccccactat 20

<210> SEQ ID NO 68
<211> LENGTH: 23
<212> TYPE: DNA
<213> ORGANISM: Artificial Sequence
<220> FEATURE:
<223> OTHER INFORMATION: Synthetic primer

<400> SEQUENCE: 68
tcatcttcaa accgtctcct gtt 23

<210> SEQ ID NO 69
<211> LENGTH: 22
<212> TYPE: DNA
<213> ORGANISM: Artificial Sequence
<220> FEATURE:
<223> OTHER INFORMATION: Synthetic primer

<400> SEQUENCE: 69
gatgaagcag cagtccaagg ta 22

<210> SEQ ID NO 70
<211> LENGTH: 22
<212> TYPE: DNA
<213> ORGANISM: Artificial Sequence
<220> FEATURE:
<223> OTHER INFORMATION: Synthetic primer

<400> SEQUENCE: 70
tctttgagtt ctaccgcctc ct 22

<210> SEQ ID NO 71
<211> LENGTH: 23
<212> TYPE: DNA
<213> ORGANISM: Artificial Sequence
<220> FEATURE:
<223> OTHER INFORMATION: Synthetic primer

<400> SEQUENCE: 71
atgtccctta cacacacgca aaa 23

<210> SEQ ID NO 72
<211> LENGTH: 21
<212> TYPE: DNA
<213> ORGANISM: Artificial Sequence
<220> FEATURE:
<223> OTHER INFORMATION: Synthetic primer

<400> SEQUENCE: 72
ctgccctctc tgccttttct c 21

<210> SEQ ID NO 73
<211> LENGTH: 17
<212> TYPE: DNA
<213> ORGANISM: Artificial Sequence
<220> FEATURE:
<223> OTHER INFORMATION: Synthetic primer

<400> SEQUENCE: 73
gatgcggggt cagtggg 17

<210> SEQ ID NO 74
<211> LENGTH: 23
<212> TYPE: DNA
<213> ORGANISM: Artificial Sequence
<220> FEATURE:
<223> OTHER INFORMATION: Synthetic primer

<400> SEQUENCE: 74
ccttgctaat tcctggagag gtc 23

<210> SEQ ID NO 75
<211> LENGTH: 23
<212> TYPE: DNA
<213> ORGANISM: Artificial Sequence
<220> FEATURE:
<223> OTHER INFORMATION: Synthetic primer

<400> SEQUENCE: 75
tggaaaacaa gtcaggtggg aaa 23

<210> SEQ ID NO 76
<211> LENGTH: 23
<212> TYPE: DNA
<213> ORGANISM: Artificial Sequence
<220> FEATURE:
<223> OTHER INFORMATION: Synthetic primer

<400> SEQUENCE: 76
aactccataa agcagggcaa aga 23

<210> SEQ ID NO 77
<211> LENGTH: 23
<212> TYPE: DNA
<213> ORGANISM: Artificial Sequence
<220> FEATURE:

<223> OTHER INFORMATION: Synthetic primer

<400> SEQUENCE: 77
ctccatcctc atgttcttgg tgt 23

<210> SEQ ID NO 78
<211> LENGTH: 17
<212> TYPE: DNA
<213> ORGANISM: Artificial Sequence
<220> FEATURE:
<223> OTHER INFORMATION: Synthetic primer

<400> SEQUENCE: 78
aggcagagac tgctggg 17

<210> SEQ ID NO 79
<211> LENGTH: 23
<212> TYPE: DNA
<213> ORGANISM: Artificial Sequence
<220> FEATURE:
<223> OTHER INFORMATION: Synthetic primer

<400> SEQUENCE: 79
tacctttcca tttcagtgca cca 23

<210> SEQ ID NO 80
<211> LENGTH: 23
<212> TYPE: DNA
<213> ORGANISM: Artificial Sequence
<220> FEATURE:
<223> OTHER INFORMATION: Synthetic primer

<400> SEQUENCE: 80
gcatatttgg tagacgcatg acc 23

<210> SEQ ID NO 81
<211> LENGTH: 23
<212> TYPE: DNA
<213> ORGANISM: Artificial Sequence
<220> FEATURE:
<223> OTHER INFORMATION: Synthetic primer

<400> SEQUENCE: 81
caggaagctc tgcaagtact caa 23

<210> SEQ ID NO 82
<211> LENGTH: 21
<212> TYPE: DNA
<213> ORGANISM: Artificial Sequence
<220> FEATURE:
<223> OTHER INFORMATION: Synthetic primer

<400> SEQUENCE: 82
cactctcact gcgcttgtct t 21

<210> SEQ ID NO 83
<211> LENGTH: 23
<212> TYPE: DNA
<213> ORGANISM: Artificial Sequence
<220> FEATURE:
<223> OTHER INFORMATION: Synthetic primer

<400> SEQUENCE: 83
gtccccgtat gagacgaaga gtt 23

```
<210> SEQ ID NO 84
<211> LENGTH: 23
<212> TYPE: DNA
<213> ORGANISM: Artificial Sequence
<220> FEATURE:
<223> OTHER INFORMATION: Synthetic primer

<400> SEQUENCE: 84

agaagcaaca aaactgacgg agg                                              23

<210> SEQ ID NO 85
<211> LENGTH: 23
<212> TYPE: DNA
<213> ORGANISM: Artificial Sequence
<220> FEATURE:
<223> OTHER INFORMATION: Synthetic primer

<400> SEQUENCE: 85

ctgcgtggaa gttgttgtag ttg                                              23

<210> SEQ ID NO 86
<211> LENGTH: 23
<212> TYPE: DNA
<213> ORGANISM: Artificial Sequence
<220> FEATURE:
<223> OTHER INFORMATION: Synthetic primer

<400> SEQUENCE: 86

cccttttttg tctttggcag gaa                                              23

<210> SEQ ID NO 87
<211> LENGTH: 23
<212> TYPE: DNA
<213> ORGANISM: Artificial Sequence
<220> FEATURE:
<223> OTHER INFORMATION: Synthetic primer

<400> SEQUENCE: 87

cttacctggg tatggcactc ttc                                              23

<210> SEQ ID NO 88
<211> LENGTH: 23
<212> TYPE: DNA
<213> ORGANISM: Artificial Sequence
<220> FEATURE:
<223> OTHER INFORMATION: Synthetic primer

<400> SEQUENCE: 88

ccctctgcct gatgaataac caa                                              23

<210> SEQ ID NO 89
<211> LENGTH: 24
<212> TYPE: DNA
<213> ORGANISM: Artificial Sequence
<220> FEATURE:
<223> OTHER INFORMATION: Synthetic primer

<400> SEQUENCE: 89

acttccattt ctctccccta aaca                                             24

<210> SEQ ID NO 90
<211> LENGTH: 23
<212> TYPE: DNA
<213> ORGANISM: Artificial Sequence
<220> FEATURE:
<223> OTHER INFORMATION: Synthetic primer
```

-continued

<400> SEQUENCE: 90
caatgtcccc cgaatcattc ctt 23

<210> SEQ ID NO 91
<211> LENGTH: 23
<212> TYPE: DNA
<213> ORGANISM: Artificial Sequence
<220> FEATURE:
<223> OTHER INFORMATION: Synthetic primer

<400> SEQUENCE: 91
gctggctacg gaattgaaag cta 23

<210> SEQ ID NO 92
<211> LENGTH: 23
<212> TYPE: DNA
<213> ORGANISM: Artificial Sequence
<220> FEATURE:
<223> OTHER INFORMATION: Synthetic primer

<400> SEQUENCE: 92
atgatccact gctggaaaaa gga 23

<210> SEQ ID NO 93
<211> LENGTH: 23
<212> TYPE: DNA
<213> ORGANISM: Artificial Sequence
<220> FEATURE:
<223> OTHER INFORMATION: Synthetic primer

<400> SEQUENCE: 93
attgccaaaa gatttaaggg tgg 23

<210> SEQ ID NO 94
<211> LENGTH: 23
<212> TYPE: DNA
<213> ORGANISM: Artificial Sequence
<220> FEATURE:
<223> OTHER INFORMATION: Synthetic primer

<400> SEQUENCE: 94
ctccatcccc aactacaaca act 23

<210> SEQ ID NO 95
<211> LENGTH: 22
<212> TYPE: DNA
<213> ORGANISM: Artificial Sequence
<220> FEATURE:
<223> OTHER INFORMATION: Synthetic primer

<400> SEQUENCE: 95
gcccatttcc cagtctcttg at 22

<210> SEQ ID NO 96
<211> LENGTH: 23
<212> TYPE: DNA
<213> ORGANISM: Artificial Sequence
<220> FEATURE:
<223> OTHER INFORMATION: Synthetic primer

<400> SEQUENCE: 96
acatgtgttc tgctcttctc tcc 23

<210> SEQ ID NO 97
<211> LENGTH: 23

<212> TYPE: DNA
<213> ORGANISM: Artificial Sequence
<220> FEATURE:
<223> OTHER INFORMATION: Synthetic primer

<400> SEQUENCE: 97
gaggatgggg cttagaaagc aaa 23

<210> SEQ ID NO 98
<211> LENGTH: 23
<212> TYPE: DNA
<213> ORGANISM: Artificial Sequence
<220> FEATURE:
<223> OTHER INFORMATION: Synthetic primer

<400> SEQUENCE: 98
gtacgggagg ttcacaatca agt 23

<210> SEQ ID NO 99
<211> LENGTH: 23
<212> TYPE: DNA
<213> ORGANISM: Artificial Sequence
<220> FEATURE:
<223> OTHER INFORMATION: Synthetic primer

<400> SEQUENCE: 99
tcttctatca atcgggccaa tcc 23

<210> SEQ ID NO 100
<211> LENGTH: 23
<212> TYPE: DNA
<213> ORGANISM: Artificial Sequence
<220> FEATURE:
<223> OTHER INFORMATION: Synthetic primer

<400> SEQUENCE: 100
cgtgtctaag tacattgggt cgt 23

<210> SEQ ID NO 101
<211> LENGTH: 22
<212> TYPE: DNA
<213> ORGANISM: Artificial Sequence
<220> FEATURE:
<223> OTHER INFORMATION: Synthetic primer

<400> SEQUENCE: 101
accagaaatg caagacccct tc 22

<210> SEQ ID NO 102
<211> LENGTH: 23
<212> TYPE: DNA
<213> ORGANISM: Artificial Sequence
<220> FEATURE:
<223> OTHER INFORMATION: Synthetic primer

<400> SEQUENCE: 102
tctcccttct tgtgaatttc gtt 23

<210> SEQ ID NO 103
<211> LENGTH: 23
<212> TYPE: DNA
<213> ORGANISM: Artificial Sequence
<220> FEATURE:
<223> OTHER INFORMATION: Synthetic primer

<400> SEQUENCE: 103
tttctgaagg aagggaaggg aag 23

<210> SEQ ID NO 104
<211> LENGTH: 23
<212> TYPE: DNA
<213> ORGANISM: Artificial Sequence
<220> FEATURE:
<223> OTHER INFORMATION: Synthetic primer

<400> SEQUENCE: 104
gcgatcagca aacattctag tgg 23

<210> SEQ ID NO 105
<211> LENGTH: 23
<212> TYPE: DNA
<213> ORGANISM: Artificial Sequence
<220> FEATURE:
<223> OTHER INFORMATION: Synthetic primer

<400> SEQUENCE: 105
ccttccatct ttggtgtttg gga 23

<210> SEQ ID NO 106
<211> LENGTH: 24
<212> TYPE: DNA
<213> ORGANISM: Artificial Sequence
<220> FEATURE:
<223> OTHER INFORMATION: Synthetic primer

<400> SEQUENCE: 106
ggcttaccga tctgtctgtc aaaa 24

<210> SEQ ID NO 107
<211> LENGTH: 23
<212> TYPE: DNA
<213> ORGANISM: Artificial Sequence
<220> FEATURE:
<223> OTHER INFORMATION: Synthetic primer

<400> SEQUENCE: 107
agcctttcat cccctctgac taa 23

<210> SEQ ID NO 108
<211> LENGTH: 23
<212> TYPE: DNA
<213> ORGANISM: Artificial Sequence
<220> FEATURE:
<223> OTHER INFORMATION: Synthetic primer

<400> SEQUENCE: 108
ggtggtactt tggaaaactt ggc 23

<210> SEQ ID NO 109
<211> LENGTH: 23
<212> TYPE: DNA
<213> ORGANISM: Artificial Sequence
<220> FEATURE:
<223> OTHER INFORMATION: Synthetic primer

<400> SEQUENCE: 109
atgtagatgg gctcctcaga cac 23

<210> SEQ ID NO 110
<211> LENGTH: 25
<212> TYPE: DNA
<213> ORGANISM: Artificial Sequence
<220> FEATURE:
<223> OTHER INFORMATION: Synthetic primer

<400> SEQUENCE: 110
tggtttgact tcatattctg ggatg 25

<210> SEQ ID NO 111
<211> LENGTH: 23
<212> TYPE: DNA
<213> ORGANISM: Artificial Sequence
<220> FEATURE:
<223> OTHER INFORMATION: Synthetic primer

<400> SEQUENCE: 111
gtcaactgga gccacataat tgc 23

<210> SEQ ID NO 112
<211> LENGTH: 23
<212> TYPE: DNA
<213> ORGANISM: Artificial Sequence
<220> FEATURE:
<223> OTHER INFORMATION: Synthetic primer

<400> SEQUENCE: 112
gtggcaggat gattaggtga cag 23

<210> SEQ ID NO 113
<211> LENGTH: 23
<212> TYPE: DNA
<213> ORGANISM: Artificial Sequence
<220> FEATURE:
<223> OTHER INFORMATION: Synthetic primer

<400> SEQUENCE: 113
tacctttggt ggtttcactc tcg 23

<210> SEQ ID NO 114
<211> LENGTH: 23
<212> TYPE: DNA
<213> ORGANISM: Artificial Sequence
<220> FEATURE:
<223> OTHER INFORMATION: Synthetic primer

<400> SEQUENCE: 114
agaggggaat tcatgggcaa aaa 23

<210> SEQ ID NO 115
<211> LENGTH: 21
<212> TYPE: DNA
<213> ORGANISM: Artificial Sequence
<220> FEATURE:
<223> OTHER INFORMATION: Synthetic primer

<400> SEQUENCE: 115
actttcctgc tctgggccta t 21

<210> SEQ ID NO 116
<211> LENGTH: 24
<212> TYPE: DNA
<213> ORGANISM: Artificial Sequence
<220> FEATURE:
<223> OTHER INFORMATION: Synthetic primer

<400> SEQUENCE: 116
tgggatgata tgaaaggaga ccat 24

<210> SEQ ID NO 117
<211> LENGTH: 24
<212> TYPE: DNA
<213> ORGANISM: Artificial Sequence
<220> FEATURE:
<223> OTHER INFORMATION: Synthetic primer

<400> SEQUENCE: 117
gcccaatgct gatggcattt tatt 24

<210> SEQ ID NO 118
<211> LENGTH: 23
<212> TYPE: DNA
<213> ORGANISM: Artificial Sequence
<220> FEATURE:
<223> OTHER INFORMATION: Synthetic primer

<400> SEQUENCE: 118
tttacaggga aggagattgg tgg 23

<210> SEQ ID NO 119
<211> LENGTH: 23
<212> TYPE: DNA
<213> ORGANISM: Artificial Sequence
<220> FEATURE:
<223> OTHER INFORMATION: Synthetic primer

<400> SEQUENCE: 119
ctgctgaagt gtttcaaact ggg 23

<210> SEQ ID NO 120
<211> LENGTH: 23
<212> TYPE: DNA
<213> ORGANISM: Artificial Sequence
<220> FEATURE:
<223> OTHER INFORMATION: Synthetic primer

<400> SEQUENCE: 120
atgaggccta aaaagcaagc tga 23

<210> SEQ ID NO 121
<211> LENGTH: 23
<212> TYPE: DNA
<213> ORGANISM: Artificial Sequence
<220> FEATURE:
<223> OTHER INFORMATION: Synthetic primer

<400> SEQUENCE: 121
acccaatgta cttagacacg tca 23

<210> SEQ ID NO 122
<211> LENGTH: 26
<212> TYPE: DNA
<213> ORGANISM: Artificial Sequence
<220> FEATURE:
<223> OTHER INFORMATION: Synthetic primer

<400> SEQUENCE: 122
agctctctgt tgggaattat ctttca 26

<210> SEQ ID NO 123
<211> LENGTH: 25
<212> TYPE: DNA
<213> ORGANISM: Artificial Sequence
<220> FEATURE:
<223> OTHER INFORMATION: Synthetic primer

<400> SEQUENCE: 123
ccttgcttaa tgggtgtaga tacca 25

<210> SEQ ID NO 124
<211> LENGTH: 23
<212> TYPE: DNA
<213> ORGANISM: Artificial Sequence
<220> FEATURE:
<223> OTHER INFORMATION: Synthetic primer

<400> SEQUENCE: 124
ggcttgtgag tggatgggta aaa 23

<210> SEQ ID NO 125
<211> LENGTH: 23
<212> TYPE: DNA
<213> ORGANISM: Artificial Sequence
<220> FEATURE:
<223> OTHER INFORMATION: Synthetic primer

<400> SEQUENCE: 125
tgtactgcag agacaagagg atg 23

<210> SEQ ID NO 126
<211> LENGTH: 22
<212> TYPE: DNA
<213> ORGANISM: Artificial Sequence
<220> FEATURE:
<223> OTHER INFORMATION: Synthetic primer

<400> SEQUENCE: 126
ggagcccatc atctgcaaaa ac 22

<210> SEQ ID NO 127
<211> LENGTH: 22
<212> TYPE: DNA
<213> ORGANISM: Artificial Sequence
<220> FEATURE:
<223> OTHER INFORMATION: Synthetic primer

<400> SEQUENCE: 127
ggactaggcg tgggatgttt tt 22

<210> SEQ ID NO 128
<211> LENGTH: 23
<212> TYPE: DNA
<213> ORGANISM: Artificial Sequence
<220> FEATURE:
<223> OTHER INFORMATION: Synthetic primer

<400> SEQUENCE: 128
gtgttgttgc ttggggttca aat 23

<210> SEQ ID NO 129
<211> LENGTH: 20
<212> TYPE: DNA
<213> ORGANISM: Artificial Sequence
<220> FEATURE:
<223> OTHER INFORMATION: Synthetic primer

<400> SEQUENCE: 129
gctccccaaa cctccaaact 20

<210> SEQ ID NO 130

<211> LENGTH: 23
<212> TYPE: DNA
<213> ORGANISM: Artificial Sequence
<220> FEATURE:
<223> OTHER INFORMATION: Synthetic primer

<400> SEQUENCE: 130
aaacatccca gaaaagtgga ccc 23

<210> SEQ ID NO 131
<211> LENGTH: 23
<212> TYPE: DNA
<213> ORGANISM: Artificial Sequence
<220> FEATURE:
<223> OTHER INFORMATION: Synthetic primer

<400> SEQUENCE: 131
catgtctgct tttcagccac ttg 23

<210> SEQ ID NO 132
<211> LENGTH: 23
<212> TYPE: DNA
<213> ORGANISM: Artificial Sequence
<220> FEATURE:
<223> OTHER INFORMATION: Synthetic primer

<400> SEQUENCE: 132
ctgggcagga agattatgat cgc 23

<210> SEQ ID NO 133
<211> LENGTH: 23
<212> TYPE: DNA
<213> ORGANISM: Artificial Sequence
<220> FEATURE:
<223> OTHER INFORMATION: Synthetic primer

<400> SEQUENCE: 133
tctgccacat agttctcaaa cac 23

<210> SEQ ID NO 134
<211> LENGTH: 23
<212> TYPE: DNA
<213> ORGANISM: Artificial Sequence
<220> FEATURE:
<223> OTHER INFORMATION: Synthetic primer

<400> SEQUENCE: 134
tgacttcttg tgcattgcag gta 23

<210> SEQ ID NO 135
<211> LENGTH: 23
<212> TYPE: DNA
<213> ORGANISM: Artificial Sequence
<220> FEATURE:
<223> OTHER INFORMATION: Synthetic primer

<400> SEQUENCE: 135
caggcagtga caaatatcag ggt 23

<210> SEQ ID NO 136
<211> LENGTH: 23
<212> TYPE: DNA
<213> ORGANISM: Artificial Sequence
<220> FEATURE:
<223> OTHER INFORMATION: Synthetic primer

<400> SEQUENCE: 136
ccttgcactc ttgtggttgt ttt 23

<210> SEQ ID NO 137
<211> LENGTH: 23
<212> TYPE: DNA
<213> ORGANISM: Artificial Sequence
<220> FEATURE:
<223> OTHER INFORMATION: Synthetic primer

<400> SEQUENCE: 137
gtttcacaag acaaggcacc cag 23

<210> SEQ ID NO 138
<211> LENGTH: 23
<212> TYPE: DNA
<213> ORGANISM: Artificial Sequence
<220> FEATURE:
<223> OTHER INFORMATION: Synthetic primer

<400> SEQUENCE: 138
gtgaaacctg aagaaggcag aga 23

<210> SEQ ID NO 139
<211> LENGTH: 27
<212> TYPE: DNA
<213> ORGANISM: Artificial Sequence
<220> FEATURE:
<223> OTHER INFORMATION: Synthetic primer

<400> SEQUENCE: 139
tgaaaaaggc cagtaatcat acactaa 27

<210> SEQ ID NO 140
<211> LENGTH: 23
<212> TYPE: DNA
<213> ORGANISM: Artificial Sequence
<220> FEATURE:
<223> OTHER INFORMATION: Synthetic primer

<400> SEQUENCE: 140
tggagtgttc agcaaagacc aaa 23

<210> SEQ ID NO 141
<211> LENGTH: 19
<212> TYPE: DNA
<213> ORGANISM: Artificial Sequence
<220> FEATURE:
<223> OTHER INFORMATION: Synthetic primer

<400> SEQUENCE: 141
ctagctcccg ccttgtgtg 19

<210> SEQ ID NO 142
<211> LENGTH: 23
<212> TYPE: DNA
<213> ORGANISM: Artificial Sequence
<220> FEATURE:
<223> OTHER INFORMATION: Synthetic primer

<400> SEQUENCE: 142
tgcaatttca ctgaggttct tgg 23

<210> SEQ ID NO 143
<211> LENGTH: 24
<212> TYPE: DNA

<213> ORGANISM: Artificial Sequence
<220> FEATURE:
<223> OTHER INFORMATION: Synthetic primer

<400> SEQUENCE: 143
agctctaatt ctctacatgc tcca 24

<210> SEQ ID NO 144
<211> LENGTH: 24
<212> TYPE: DNA
<213> ORGANISM: Artificial Sequence
<220> FEATURE:
<223> OTHER INFORMATION: Synthetic primer

<400> SEQUENCE: 144
tggaaagaca tgcttgctca tagt 24

<210> SEQ ID NO 145
<211> LENGTH: 23
<212> TYPE: DNA
<213> ORGANISM: Artificial Sequence
<220> FEATURE:
<223> OTHER INFORMATION: Synthetic primer

<400> SEQUENCE: 145
acctctctca ctccatcttt ggt 23

<210> SEQ ID NO 146
<211> LENGTH: 36
<212> TYPE: DNA
<213> ORGANISM: Artificial Sequence
<220> FEATURE:
<223> OTHER INFORMATION: Synthetic primer

<400> SEQUENCE: 146
aatcttttag atgaatttga atacttttta cttact 36

<210> SEQ ID NO 147
<211> LENGTH: 23
<212> TYPE: DNA
<213> ORGANISM: Artificial Sequence
<220> FEATURE:
<223> OTHER INFORMATION: Synthetic primer

<400> SEQUENCE: 147
gaacactcca tgtacccaaa agc 23

<210> SEQ ID NO 148
<211> LENGTH: 22
<212> TYPE: DNA
<213> ORGANISM: Artificial Sequence
<220> FEATURE:
<223> OTHER INFORMATION: Synthetic primer

<400> SEQUENCE: 148
gaccgacgag caaaactgtc tc 22

<210> SEQ ID NO 149
<211> LENGTH: 23
<212> TYPE: DNA
<213> ORGANISM: Artificial Sequence
<220> FEATURE:
<223> OTHER INFORMATION: Synthetic primer

<400> SEQUENCE: 149
gtccactctt atggcaccaa cat 23

-continued

<210> SEQ ID NO 150
<211> LENGTH: 25
<212> TYPE: DNA
<213> ORGANISM: Artificial Sequence
<220> FEATURE:
<223> OTHER INFORMATION: Synthetic primer

<400> SEQUENCE: 150
tgcagtggtt tcaacaatta agagg 25

<210> SEQ ID NO 151
<211> LENGTH: 29
<212> TYPE: DNA
<213> ORGANISM: Artificial Sequence
<220> FEATURE:
<223> OTHER INFORMATION: Synthetic primer

<400> SEQUENCE: 151
ctcactagcc ttcataaaat aatcatcaa 29

<210> SEQ ID NO 152
<211> LENGTH: 20
<212> TYPE: DNA
<213> ORGANISM: Artificial Sequence
<220> FEATURE:
<223> OTHER INFORMATION: Synthetic primer

<400> SEQUENCE: 152
ctctgtctga gggtgatgtg 20

<210> SEQ ID NO 153
<211> LENGTH: 23
<212> TYPE: DNA
<213> ORGANISM: Artificial Sequence
<220> FEATURE:
<223> OTHER INFORMATION: Synthetic primer

<400> SEQUENCE: 153
aacttttgcg actttcagga cca 23

<210> SEQ ID NO 154
<211> LENGTH: 23
<212> TYPE: DNA
<213> ORGANISM: Artificial Sequence
<220> FEATURE:
<223> OTHER INFORMATION: Synthetic primer

<400> SEQUENCE: 154
ctaactggat tgggccgtct cat 23

<210> SEQ ID NO 155
<211> LENGTH: 24
<212> TYPE: DNA
<213> ORGANISM: Artificial Sequence
<220> FEATURE:
<223> OTHER INFORMATION: Synthetic primer

<400> SEQUENCE: 155
gcagtgaaga gaagctactg tgtt 24

<210> SEQ ID NO 156
<211> LENGTH: 23
<212> TYPE: DNA
<213> ORGANISM: Artificial Sequence
<220> FEATURE:

<223> OTHER INFORMATION: Synthetic primer

<400> SEQUENCE: 156
ttactcttca ttcaaggcac acc 23

<210> SEQ ID NO 157
<211> LENGTH: 23
<212> TYPE: DNA
<213> ORGANISM: Artificial Sequence
<220> FEATURE:
<223> OTHER INFORMATION: Synthetic primer

<400> SEQUENCE: 157
ttgttttgtt ttggttgggg tgg 23

<210> SEQ ID NO 158
<211> LENGTH: 23
<212> TYPE: DNA
<213> ORGANISM: Artificial Sequence
<220> FEATURE:
<223> OTHER INFORMATION: Synthetic primer

<400> SEQUENCE: 158
cgagtagagt ttgtcagcca gag 23

<210> SEQ ID NO 159
<211> LENGTH: 23
<212> TYPE: DNA
<213> ORGANISM: Artificial Sequence
<220> FEATURE:
<223> OTHER INFORMATION: Synthetic primer

<400> SEQUENCE: 159
acaaactcta ctcggagctt acc 23

<210> SEQ ID NO 160
<211> LENGTH: 23
<212> TYPE: DNA
<213> ORGANISM: Artificial Sequence
<220> FEATURE:
<223> OTHER INFORMATION: Synthetic primer

<400> SEQUENCE: 160
aaagtgcacg ctgaactctc ttc 23

<210> SEQ ID NO 161
<211> LENGTH: 23
<212> TYPE: DNA
<213> ORGANISM: Artificial Sequence
<220> FEATURE:
<223> OTHER INFORMATION: Synthetic primer

<400> SEQUENCE: 161
atgctaatgg tcaggaaaag cag 23

<210> SEQ ID NO 162
<211> LENGTH: 23
<212> TYPE: DNA
<213> ORGANISM: Artificial Sequence
<220> FEATURE:
<223> OTHER INFORMATION: Synthetic primer

<400> SEQUENCE: 162
tttaaagggg ttgtggcatg cag 23

<210> SEQ ID NO 163
<211> LENGTH: 22
<212> TYPE: DNA
<213> ORGANISM: Artificial Sequence
<220> FEATURE:
<223> OTHER INFORMATION: Synthetic primer

<400> SEQUENCE: 163
gaggacaacg atgaggtctg gt 22

<210> SEQ ID NO 164
<211> LENGTH: 23
<212> TYPE: DNA
<213> ORGANISM: Artificial Sequence
<220> FEATURE:
<223> OTHER INFORMATION: Synthetic primer

<400> SEQUENCE: 164
tgctggtaaa agacgaggga gat 23

<210> SEQ ID NO 165
<211> LENGTH: 23
<212> TYPE: DNA
<213> ORGANISM: Artificial Sequence
<220> FEATURE:
<223> OTHER INFORMATION: Synthetic primer

<400> SEQUENCE: 165
atatgaacac agagcaccag agt 23

<210> SEQ ID NO 166
<211> LENGTH: 20
<212> TYPE: DNA
<213> ORGANISM: Artificial Sequence
<220> FEATURE:
<223> OTHER INFORMATION: Synthetic primer

<400> SEQUENCE: 166
ctaagctgtc ctcagcccaa 20

<210> SEQ ID NO 167
<211> LENGTH: 23
<212> TYPE: DNA
<213> ORGANISM: Artificial Sequence
<220> FEATURE:
<223> OTHER INFORMATION: Synthetic primer

<400> SEQUENCE: 167
tcgagaattt ggaggaaaac ctg 23

<210> SEQ ID NO 168
<211> LENGTH: 23
<212> TYPE: DNA
<213> ORGANISM: Artificial Sequence
<220> FEATURE:
<223> OTHER INFORMATION: Synthetic primer

<400> SEQUENCE: 168
gtcttgactg gctctgctaa cat 23

<210> SEQ ID NO 169
<211> LENGTH: 22
<212> TYPE: DNA
<213> ORGANISM: Artificial Sequence
<220> FEATURE:
<223> OTHER INFORMATION: Synthetic primer

<400> SEQUENCE: 169
cccttaccct gggcttttga at 22

<210> SEQ ID NO 170
<211> LENGTH: 23
<212> TYPE: DNA
<213> ORGANISM: Artificial Sequence
<220> FEATURE:
<223> OTHER INFORMATION: Synthetic primer

<400> SEQUENCE: 170
accttggctg gtaaagtgta tgg 23

<210> SEQ ID NO 171
<211> LENGTH: 23
<212> TYPE: DNA
<213> ORGANISM: Artificial Sequence
<220> FEATURE:
<223> OTHER INFORMATION: Synthetic primer

<400> SEQUENCE: 171
gcttacttca agcaaagctc agt 23

<210> SEQ ID NO 172
<211> LENGTH: 23
<212> TYPE: DNA
<213> ORGANISM: Artificial Sequence
<220> FEATURE:
<223> OTHER INFORMATION: Synthetic primer

<400> SEQUENCE: 172
agtgttgtgt tactttggtt ggg 23

<210> SEQ ID NO 173
<211> LENGTH: 23
<212> TYPE: DNA
<213> ORGANISM: Artificial Sequence
<220> FEATURE:
<223> OTHER INFORMATION: Synthetic primer

<400> SEQUENCE: 173
tcaggaggag aaaaaacgga gtg 23

<210> SEQ ID NO 174
<211> LENGTH: 23
<212> TYPE: DNA
<213> ORGANISM: Artificial Sequence
<220> FEATURE:
<223> OTHER INFORMATION: Synthetic primer

<400> SEQUENCE: 174
tggggctgac ttttcctttt cat 23

<210> SEQ ID NO 175
<211> LENGTH: 23
<212> TYPE: DNA
<213> ORGANISM: Artificial Sequence
<220> FEATURE:
<223> OTHER INFORMATION: Synthetic primer

<400> SEQUENCE: 175
catgctttcc cacacagcta atg 23

<210> SEQ ID NO 176
<211> LENGTH: 22

-continued

<212> TYPE: DNA
<213> ORGANISM: Artificial Sequence
<220> FEATURE:
<223> OTHER INFORMATION: Synthetic primer

<400> SEQUENCE: 176
ctgaccagac ctcatcgttg tc 22

<210> SEQ ID NO 177
<211> LENGTH: 23
<212> TYPE: DNA
<213> ORGANISM: Artificial Sequence
<220> FEATURE:
<223> OTHER INFORMATION: Synthetic primer

<400> SEQUENCE: 177
ccattcctga taccatcacc tcc 23

<210> SEQ ID NO 178
<211> LENGTH: 23
<212> TYPE: DNA
<213> ORGANISM: Artificial Sequence
<220> FEATURE:
<223> OTHER INFORMATION: Synthetic primer

<400> SEQUENCE: 178
actcacacga ctattctggc ttc 23

<210> SEQ ID NO 179
<211> LENGTH: 23
<212> TYPE: DNA
<213> ORGANISM: Artificial Sequence
<220> FEATURE:
<223> OTHER INFORMATION: Synthetic primer

<400> SEQUENCE: 179
gagacaagga gcaaacacga gat 23

<210> SEQ ID NO 180
<211> LENGTH: 23
<212> TYPE: DNA
<213> ORGANISM: Artificial Sequence
<220> FEATURE:
<223> OTHER INFORMATION: Synthetic primer

<400> SEQUENCE: 180
tccagtgtat tgtttggagg tca 23

<210> SEQ ID NO 181
<211> LENGTH: 23
<212> TYPE: DNA
<213> ORGANISM: Artificial Sequence
<220> FEATURE:
<223> OTHER INFORMATION: Synthetic primer

<400> SEQUENCE: 181
acacacacac acgttttctt tgg 23

<210> SEQ ID NO 182
<211> LENGTH: 23
<212> TYPE: DNA
<213> ORGANISM: Artificial Sequence
<220> FEATURE:
<223> OTHER INFORMATION: Synthetic primer

<400> SEQUENCE: 182

-continued cttccacact cccaaactca tcc 23

<210> SEQ ID NO 183
<211> LENGTH: 23
<212> TYPE: DNA
<213> ORGANISM: Artificial Sequence
<220> FEATURE:
<223> OTHER INFORMATION: Synthetic primer

<400> SEQUENCE: 183
tcagctgcac agcctatata atg 23

<210> SEQ ID NO 184
<211> LENGTH: 23
<212> TYPE: DNA
<213> ORGANISM: Artificial Sequence
<220> FEATURE:
<223> OTHER INFORMATION: Synthetic primer

<400> SEQUENCE: 184
acttccttgg gatcttgctt ctg 23

<210> SEQ ID NO 185
<211> LENGTH: 25
<212> TYPE: DNA
<213> ORGANISM: Artificial Sequence
<220> FEATURE:
<223> OTHER INFORMATION: Synthetic primer

<400> SEQUENCE: 185
tcagcagttg taccattaga ccaaa 25

<210> SEQ ID NO 186
<211> LENGTH: 23
<212> TYPE: DNA
<213> ORGANISM: Artificial Sequence
<220> FEATURE:
<223> OTHER INFORMATION: Synthetic primer

<400> SEQUENCE: 186
ggagctgcac tgtagttatg gat 23

<210> SEQ ID NO 187
<211> LENGTH: 23
<212> TYPE: DNA
<213> ORGANISM: Artificial Sequence
<220> FEATURE:
<223> OTHER INFORMATION: Synthetic primer

<400> SEQUENCE: 187
aaaatggctg aaaaagcccg tga 23

<210> SEQ ID NO 188
<211> LENGTH: 21
<212> TYPE: DNA
<213> ORGANISM: Artificial Sequence
<220> FEATURE:
<223> OTHER INFORMATION: Synthetic primer

<400> SEQUENCE: 188
gtcacggaca tggtcctttc g 21

<210> SEQ ID NO 189
<211> LENGTH: 23
<212> TYPE: DNA
<213> ORGANISM: Artificial Sequence
<220> FEATURE:
<223> OTHER INFORMATION: Synthetic primer

<400> SEQUENCE: 189
tgagccacat gaaacttcag agc 23

<210> SEQ ID NO 190
<211> LENGTH: 23
<212> TYPE: DNA
<213> ORGANISM: Artificial Sequence
<220> FEATURE:
<223> OTHER INFORMATION: Synthetic primer

<400> SEQUENCE: 190
acaggttggt tgtggtcttt tca 23

<210> SEQ ID NO 191
<211> LENGTH: 23
<212> TYPE: DNA
<213> ORGANISM: Artificial Sequence
<220> FEATURE:
<223> OTHER INFORMATION: Synthetic primer

<400> SEQUENCE: 191
tctaactctg agctgcctcc aaa 23

<210> SEQ ID NO 192
<211> LENGTH: 23
<212> TYPE: DNA
<213> ORGANISM: Artificial Sequence
<220> FEATURE:
<223> OTHER INFORMATION: Synthetic primer

<400> SEQUENCE: 192
gctttgtggt tccctggatg tta 23

<210> SEQ ID NO 193
<211> LENGTH: 23
<212> TYPE: DNA
<213> ORGANISM: Artificial Sequence
<220> FEATURE:
<223> OTHER INFORMATION: Synthetic primer

<400> SEQUENCE: 193
tgaggcatca ctgccatcaa ttc 23

<210> SEQ ID NO 194
<211> LENGTH: 23
<212> TYPE: DNA
<213> ORGANISM: Artificial Sequence
<220> FEATURE:
<223> OTHER INFORMATION: Synthetic primer

<400> SEQUENCE: 194
ttgggactgc ccttgattca ttt 23

<210> SEQ ID NO 195
<211> LENGTH: 22
<212> TYPE: DNA
<213> ORGANISM: Artificial Sequence
<220> FEATURE:
<223> OTHER INFORMATION: Synthetic primer

<400> SEQUENCE: 195
caggttcctc agcttccttc ag 22

<210> SEQ ID NO 196
<211> LENGTH: 23
<212> TYPE: DNA
<213> ORGANISM: Artificial Sequence
<220> FEATURE:
<223> OTHER INFORMATION: Synthetic primer

<400> SEQUENCE: 196
tttcagaaag catcggagaa ggg 23

<210> SEQ ID NO 197
<211> LENGTH: 23
<212> TYPE: DNA
<213> ORGANISM: Artificial Sequence
<220> FEATURE:
<223> OTHER INFORMATION: Synthetic primer

<400> SEQUENCE: 197
ccatgcaaat gtttttcctg tgc 23

<210> SEQ ID NO 198
<211> LENGTH: 23
<212> TYPE: DNA
<213> ORGANISM: Artificial Sequence
<220> FEATURE:
<223> OTHER INFORMATION: Synthetic primer

<400> SEQUENCE: 198
ttaattggcc tgtgcatctg act 23

<210> SEQ ID NO 199
<211> LENGTH: 19
<212> TYPE: DNA
<213> ORGANISM: Artificial Sequence
<220> FEATURE:
<223> OTHER INFORMATION: Synthetic primer

<400> SEQUENCE: 199
tgctgctcta aggtggcat 19

<210> SEQ ID NO 200
<211> LENGTH: 24
<212> TYPE: DNA
<213> ORGANISM: Artificial Sequence
<220> FEATURE:
<223> OTHER INFORMATION: Synthetic primer

<400> SEQUENCE: 200
gcaggtggat tctcttgctt agtt 24

<210> SEQ ID NO 201
<211> LENGTH: 23
<212> TYPE: DNA
<213> ORGANISM: Artificial Sequence
<220> FEATURE:
<223> OTHER INFORMATION: Synthetic primer

<400> SEQUENCE: 201
aaatgccatt aacagtcagg cta 23

<210> SEQ ID NO 202
<211> LENGTH: 25
<212> TYPE: DNA
<213> ORGANISM: Artificial Sequence
<220> FEATURE:
<223> OTHER INFORMATION: Synthetic primer

<400> SEQUENCE: 202
aggtatttag cattgcagct agttt 25

<210> SEQ ID NO 203
<211> LENGTH: 23
<212> TYPE: DNA
<213> ORGANISM: Artificial Sequence
<220> FEATURE:
<223> OTHER INFORMATION: Synthetic primer

<400> SEQUENCE: 203
gctttcaaga acaggagcag aag 23

<210> SEQ ID NO 204
<211> LENGTH: 23
<212> TYPE: DNA
<213> ORGANISM: Artificial Sequence
<220> FEATURE:
<223> OTHER INFORMATION: Synthetic primer

<400> SEQUENCE: 204
cttttgagtg tccttctggg gag 23

<210> SEQ ID NO 205
<211> LENGTH: 27
<212> TYPE: DNA
<213> ORGANISM: Artificial Sequence
<220> FEATURE:
<223> OTHER INFORMATION: Synthetic primer

<400> SEQUENCE: 205
ggaagtgaaa atagagggta aacctga 27

<210> SEQ ID NO 206
<211> LENGTH: 23
<212> TYPE: DNA
<213> ORGANISM: Artificial Sequence
<220> FEATURE:
<223> OTHER INFORMATION: Synthetic primer

<400> SEQUENCE: 206
tgaggtgttc tgacattggt ctt 23

<210> SEQ ID NO 207
<211> LENGTH: 28
<212> TYPE: DNA
<213> ORGANISM: Artificial Sequence
<220> FEATURE:
<223> OTHER INFORMATION: Synthetic primer

<400> SEQUENCE: 207
cacattttaa tttttgtttc catgctct 28

<210> SEQ ID NO 208
<211> LENGTH: 19
<212> TYPE: DNA
<213> ORGANISM: Artificial Sequence
<220> FEATURE:
<223> OTHER INFORMATION: Synthetic primer

<400> SEQUENCE: 208
ggcagtgggc ttccattct 19

<210> SEQ ID NO 209

<211> LENGTH: 23
<212> TYPE: DNA
<213> ORGANISM: Artificial Sequence
<220> FEATURE:
<223> OTHER INFORMATION: Synthetic primer

<400> SEQUENCE: 209
aagaatccca ataggaatca ccc 23

<210> SEQ ID NO 210
<211> LENGTH: 23
<212> TYPE: DNA
<213> ORGANISM: Artificial Sequence
<220> FEATURE:
<223> OTHER INFORMATION: Synthetic primer

<400> SEQUENCE: 210
tgggatttct gaggcacata gtc 23

<210> SEQ ID NO 211
<211> LENGTH: 21
<212> TYPE: DNA
<213> ORGANISM: Artificial Sequence
<220> FEATURE:
<223> OTHER INFORMATION: Synthetic primer

<400> SEQUENCE: 211
acttcatggg agccacctct a 21

<210> SEQ ID NO 212
<211> LENGTH: 23
<212> TYPE: DNA
<213> ORGANISM: Artificial Sequence
<220> FEATURE:
<223> OTHER INFORMATION: Synthetic primer

<400> SEQUENCE: 212
tgggaaagca tgtcattctc ctt 23

<210> SEQ ID NO 213
<211> LENGTH: 23
<212> TYPE: DNA
<213> ORGANISM: Artificial Sequence
<220> FEATURE:
<223> OTHER INFORMATION: Synthetic primer

<400> SEQUENCE: 213
ggttcctatt ctccccagtc tca 23

<210> SEQ ID NO 214
<211> LENGTH: 23
<212> TYPE: DNA
<213> ORGANISM: Artificial Sequence
<220> FEATURE:
<223> OTHER INFORMATION: Synthetic primer

<400> SEQUENCE: 214
tctccctgca tattttggtt tcc 23

<210> SEQ ID NO 215
<211> LENGTH: 29
<212> TYPE: DNA
<213> ORGANISM: Artificial Sequence
<220> FEATURE:
<223> OTHER INFORMATION: Synthetic primer

<400> SEQUENCE: 215
cattcacaca cacttttatt tttcagatt 29

<210> SEQ ID NO 216
<211> LENGTH: 21
<212> TYPE: DNA
<213> ORGANISM: Artificial Sequence
<220> FEATURE:
<223> OTHER INFORMATION: Synthetic primer

<400> SEQUENCE: 216
gctgccattc tgcatgttgt g 21

<210> SEQ ID NO 217
<211> LENGTH: 23
<212> TYPE: DNA
<213> ORGANISM: Artificial Sequence
<220> FEATURE:
<223> OTHER INFORMATION: Synthetic primer

<400> SEQUENCE: 217
cacctcaagc ataacccacc aat 23

<210> SEQ ID NO 218
<211> LENGTH: 22
<212> TYPE: DNA
<213> ORGANISM: Artificial Sequence
<220> FEATURE:
<223> OTHER INFORMATION: Synthetic primer

<400> SEQUENCE: 218
gattccgctt ggtgaaaacg ag 22

<210> SEQ ID NO 219
<211> LENGTH: 23
<212> TYPE: DNA
<213> ORGANISM: Artificial Sequence
<220> FEATURE:
<223> OTHER INFORMATION: Synthetic primer

<400> SEQUENCE: 219
cccaaactga gtcttgccat agt 23

<210> SEQ ID NO 220
<211> LENGTH: 23
<212> TYPE: DNA
<213> ORGANISM: Artificial Sequence
<220> FEATURE:
<223> OTHER INFORMATION: Synthetic primer

<400> SEQUENCE: 220
tggtctcaat gatgctcttt tgc 23

<210> SEQ ID NO 221
<211> LENGTH: 22
<212> TYPE: DNA
<213> ORGANISM: Artificial Sequence
<220> FEATURE:
<223> OTHER INFORMATION: Synthetic primer

<400> SEQUENCE: 221
aaggcaagct tacacccaga aa 22

<210> SEQ ID NO 222
<211> LENGTH: 23
<212> TYPE: DNA

<213> ORGANISM: Artificial Sequence
<220> FEATURE:
<223> OTHER INFORMATION: Synthetic primer

<400> SEQUENCE: 222
tgactgcaca tgagcttttg gta 23

<210> SEQ ID NO 223
<211> LENGTH: 23
<212> TYPE: DNA
<213> ORGANISM: Artificial Sequence
<220> FEATURE:
<223> OTHER INFORMATION: Synthetic primer

<400> SEQUENCE: 223
ctacacatgt atgcagccct tct 23

<210> SEQ ID NO 224
<211> LENGTH: 22
<212> TYPE: DNA
<213> ORGANISM: Artificial Sequence
<220> FEATURE:
<223> OTHER INFORMATION: Synthetic primer

<400> SEQUENCE: 224
agttgtcctg tagctctcca ct 22

<210> SEQ ID NO 225
<211> LENGTH: 23
<212> TYPE: DNA
<213> ORGANISM: Artificial Sequence
<220> FEATURE:
<223> OTHER INFORMATION: Synthetic primer

<400> SEQUENCE: 225
agtcactgtg tggcactaga ttt 23

<210> SEQ ID NO 226
<211> LENGTH: 23
<212> TYPE: DNA
<213> ORGANISM: Artificial Sequence
<220> FEATURE:
<223> OTHER INFORMATION: Synthetic primer

<400> SEQUENCE: 226
gagggagatg tgaactctgg gat 23

<210> SEQ ID NO 227
<211> LENGTH: 23
<212> TYPE: DNA
<213> ORGANISM: Artificial Sequence
<220> FEATURE:
<223> OTHER INFORMATION: Synthetic primer

<400> SEQUENCE: 227
atgctgatga tgctgataat gcc 23

<210> SEQ ID NO 228
<211> LENGTH: 20
<212> TYPE: DNA
<213> ORGANISM: Artificial Sequence
<220> FEATURE:
<223> OTHER INFORMATION: Synthetic primer

<400> SEQUENCE: 228
gcttgcaaat tgctgctgga 20

<210> SEQ ID NO 229
<211> LENGTH: 20
<212> TYPE: DNA
<213> ORGANISM: Artificial Sequence
<220> FEATURE:
<223> OTHER INFORMATION: Synthetic primer

<400> SEQUENCE: 229
agaaacctgt ggtgcctcct 20

<210> SEQ ID NO 230
<211> LENGTH: 28
<212> TYPE: DNA
<213> ORGANISM: Artificial Sequence
<220> FEATURE:
<223> OTHER INFORMATION: Synthetic primer

<400> SEQUENCE: 230
tgtcatattg ttcacttcat ctaagcta 28

<210> SEQ ID NO 231
<211> LENGTH: 23
<212> TYPE: DNA
<213> ORGANISM: Artificial Sequence
<220> FEATURE:
<223> OTHER INFORMATION: Synthetic primer

<400> SEQUENCE: 231
aatccacctg caagctgtga taa 23

<210> SEQ ID NO 232
<211> LENGTH: 23
<212> TYPE: DNA
<213> ORGANISM: Artificial Sequence
<220> FEATURE:
<223> OTHER INFORMATION: Synthetic primer

<400> SEQUENCE: 232
gttctgcagc agtggtttgt cta 23

<210> SEQ ID NO 233
<211> LENGTH: 25
<212> TYPE: DNA
<213> ORGANISM: Artificial Sequence
<220> FEATURE:
<223> OTHER INFORMATION: Synthetic primer

<400> SEQUENCE: 233
tgtcaactct tattctgctt ctgga 25

<210> SEQ ID NO 234
<211> LENGTH: 24
<212> TYPE: DNA
<213> ORGANISM: Artificial Sequence
<220> FEATURE:
<223> OTHER INFORMATION: Synthetic primer

<400> SEQUENCE: 234
gggtaagggt tcatgggatt agaa 24

<210> SEQ ID NO 235
<211> LENGTH: 23
<212> TYPE: DNA
<213> ORGANISM: Artificial Sequence
<220> FEATURE:

<223> OTHER INFORMATION: Synthetic primer

<400> SEQUENCE: 235
tccatacact ttaccagcca agg 23

<210> SEQ ID NO 236
<211> LENGTH: 23
<212> TYPE: DNA
<213> ORGANISM: Artificial Sequence
<220> FEATURE:
<223> OTHER INFORMATION: Synthetic primer

<400> SEQUENCE: 236
taatctagag gtggctccca tga 23

<210> SEQ ID NO 237
<211> LENGTH: 23
<212> TYPE: DNA
<213> ORGANISM: Artificial Sequence
<220> FEATURE:
<223> OTHER INFORMATION: Synthetic primer

<400> SEQUENCE: 237
tatctatgga agcaccagcc cta 23

<210> SEQ ID NO 238
<211> LENGTH: 23
<212> TYPE: DNA
<213> ORGANISM: Artificial Sequence
<220> FEATURE:
<223> OTHER INFORMATION: Synthetic primer

<400> SEQUENCE: 238
ctggggagaa taggaaccca gat 23

<210> SEQ ID NO 239
<211> LENGTH: 26
<212> TYPE: DNA
<213> ORGANISM: Artificial Sequence
<220> FEATURE:
<223> OTHER INFORMATION: Synthetic primer

<400> SEQUENCE: 239
ctcaaatcac agaagcaagt aaaagt 26

<210> SEQ ID NO 240
<211> LENGTH: 28
<212> TYPE: DNA
<213> ORGANISM: Artificial Sequence
<220> FEATURE:
<223> OTHER INFORMATION: Synthetic primer

<400> SEQUENCE: 240
gtatctagta atttggaagg tgactcta 28

<210> SEQ ID NO 241
<211> LENGTH: 24
<212> TYPE: DNA
<213> ORGANISM: Artificial Sequence
<220> FEATURE:
<223> OTHER INFORMATION: Synthetic primer

<400> SEQUENCE: 241
ttgtatgtgt gtgtgtttct gtgg 24

<210> SEQ ID NO 242
<211> LENGTH: 23
<212> TYPE: DNA
<213> ORGANISM: Artificial Sequence
<220> FEATURE:
<223> OTHER INFORMATION: Synthetic primer

<400> SEQUENCE: 242
gcccaagatt taagaccaaa ggc 23

<210> SEQ ID NO 243
<211> LENGTH: 23
<212> TYPE: DNA
<213> ORGANISM: Artificial Sequence
<220> FEATURE:
<223> OTHER INFORMATION: Synthetic primer

<400> SEQUENCE: 243
cgacaaagga aactagaagc caa 23

<210> SEQ ID NO 244
<211> LENGTH: 31
<212> TYPE: DNA
<213> ORGANISM: Artificial Sequence
<220> FEATURE:
<223> OTHER INFORMATION: Synthetic primer

<400> SEQUENCE: 244
tttaatatac cacacaacac atttatctac a 31

<210> SEQ ID NO 245
<211> LENGTH: 23
<212> TYPE: DNA
<213> ORGANISM: Artificial Sequence
<220> FEATURE:
<223> OTHER INFORMATION: Synthetic primer

<400> SEQUENCE: 245
gtacagtgga ccaacatctc cag 23

<210> SEQ ID NO 246
<211> LENGTH: 23
<212> TYPE: DNA
<213> ORGANISM: Artificial Sequence
<220> FEATURE:
<223> OTHER INFORMATION: Synthetic primer

<400> SEQUENCE: 246
gcctgttgat tcaagtgctg ttt 23

<210> SEQ ID NO 247
<211> LENGTH: 24
<212> TYPE: DNA
<213> ORGANISM: Artificial Sequence
<220> FEATURE:
<223> OTHER INFORMATION: Synthetic primer

<400> SEQUENCE: 247
ccaaaaggct aatggagaaa gacg 24

<210> SEQ ID NO 248
<211> LENGTH: 21
<212> TYPE: DNA
<213> ORGANISM: Artificial Sequence
<220> FEATURE:
<223> OTHER INFORMATION: Synthetic primer

<400> SEQUENCE: 248
ctctggattt tcaggcccac t 21

<210> SEQ ID NO 249
<211> LENGTH: 23
<212> TYPE: DNA
<213> ORGANISM: Artificial Sequence
<220> FEATURE:
<223> OTHER INFORMATION: Synthetic primer

<400> SEQUENCE: 249
aaagctagcg tctggtgaag aat 23

<210> SEQ ID NO 250
<211> LENGTH: 23
<212> TYPE: DNA
<213> ORGANISM: Artificial Sequence
<220> FEATURE:
<223> OTHER INFORMATION: Synthetic primer

<400> SEQUENCE: 250
aagaagcaat tgtgatggtg gtg 23

<210> SEQ ID NO 251
<211> LENGTH: 23
<212> TYPE: DNA
<213> ORGANISM: Artificial Sequence
<220> FEATURE:
<223> OTHER INFORMATION: Synthetic primer

<400> SEQUENCE: 251
aaaccagcaa cagcagcaaa aat 23

<210> SEQ ID NO 252
<211> LENGTH: 24
<212> TYPE: DNA
<213> ORGANISM: Artificial Sequence
<220> FEATURE:
<223> OTHER INFORMATION: Synthetic primer

<400> SEQUENCE: 252
ccagtcccat ttggacatta tgag 24

<210> SEQ ID NO 253
<211> LENGTH: 22
<212> TYPE: DNA
<213> ORGANISM: Artificial Sequence
<220> FEATURE:
<223> OTHER INFORMATION: Synthetic primer

<400> SEQUENCE: 253
cagtgggcct gaaaatccag ag 22

<210> SEQ ID NO 254
<211> LENGTH: 31
<212> TYPE: DNA
<213> ORGANISM: Artificial Sequence
<220> FEATURE:
<223> OTHER INFORMATION: Synthetic primer

<400> SEQUENCE: 254
acaatctgga taatattgag acagtgtttt t 31

<210> SEQ ID NO 255
<211> LENGTH: 23

<212> TYPE: DNA
<213> ORGANISM: Artificial Sequence
<220> FEATURE:
<223> OTHER INFORMATION: Synthetic primer

<400> SEQUENCE: 255
tgctaatgcc taatggtgct aca 23

<210> SEQ ID NO 256
<211> LENGTH: 23
<212> TYPE: DNA
<213> ORGANISM: Artificial Sequence
<220> FEATURE:
<223> OTHER INFORMATION: Synthetic primer

<400> SEQUENCE: 256
ggtgagtgat ctcacaggac aac 23

<210> SEQ ID NO 257
<211> LENGTH: 23
<212> TYPE: DNA
<213> ORGANISM: Artificial Sequence
<220> FEATURE:
<223> OTHER INFORMATION: Synthetic primer

<400> SEQUENCE: 257
agccaagaaa gaaatccagg tga 23

<210> SEQ ID NO 258
<211> LENGTH: 22
<212> TYPE: DNA
<213> ORGANISM: Artificial Sequence
<220> FEATURE:
<223> OTHER INFORMATION: Synthetic primer

<400> SEQUENCE: 258
cacttttccc ctcctgctca tt 22

<210> SEQ ID NO 259
<211> LENGTH: 25
<212> TYPE: DNA
<213> ORGANISM: Artificial Sequence
<220> FEATURE:
<223> OTHER INFORMATION: Synthetic primer

<400> SEQUENCE: 259
agactacaca tcctgaactt tttgc 25

<210> SEQ ID NO 260
<211> LENGTH: 22
<212> TYPE: DNA
<213> ORGANISM: Artificial Sequence
<220> FEATURE:
<223> OTHER INFORMATION: Synthetic primer

<400> SEQUENCE: 260
cgcagcttgt tgaccagaca ta 22

<210> SEQ ID NO 261
<211> LENGTH: 25
<212> TYPE: DNA
<213> ORGANISM: Artificial Sequence
<220> FEATURE:
<223> OTHER INFORMATION: Synthetic primer

<400> SEQUENCE: 261
gctcatccag aagtaaatgg agaca 25

<210> SEQ ID NO 262
<211> LENGTH: 23
<212> TYPE: DNA
<213> ORGANISM: Artificial Sequence
<220> FEATURE:
<223> OTHER INFORMATION: Synthetic primer

<400> SEQUENCE: 262
ttgatctgaa ggagcccaga gag 23

<210> SEQ ID NO 263
<211> LENGTH: 23
<212> TYPE: DNA
<213> ORGANISM: Artificial Sequence
<220> FEATURE:
<223> OTHER INFORMATION: Synthetic primer

<400> SEQUENCE: 263
tgagccattt tcaaactcac acc 23

<210> SEQ ID NO 264
<211> LENGTH: 25
<212> TYPE: DNA
<213> ORGANISM: Artificial Sequence
<220> FEATURE:
<223> OTHER INFORMATION: Synthetic primer

<400> SEQUENCE: 264
tccttctctt tgctgatcat tgttg 25

<210> SEQ ID NO 265
<211> LENGTH: 23
<212> TYPE: DNA
<213> ORGANISM: Artificial Sequence
<220> FEATURE:
<223> OTHER INFORMATION: Synthetic primer

<400> SEQUENCE: 265
cacccaatct gagcaatcca aac 23

<210> SEQ ID NO 266
<211> LENGTH: 23
<212> TYPE: DNA
<213> ORGANISM: Artificial Sequence
<220> FEATURE:
<223> OTHER INFORMATION: Synthetic primer

<400> SEQUENCE: 266
atcatggtta agagctggaa gca 23

<210> SEQ ID NO 267
<211> LENGTH: 23
<212> TYPE: DNA
<213> ORGANISM: Artificial Sequence
<220> FEATURE:
<223> OTHER INFORMATION: Synthetic primer

<400> SEQUENCE: 267
tagagggtat tccaagtgtt tgc 23

<210> SEQ ID NO 268
<211> LENGTH: 24
<212> TYPE: DNA
<213> ORGANISM: Artificial Sequence
<220> FEATURE:
<223> OTHER INFORMATION: Synthetic primer

<400> SEQUENCE: 268
agacatttgg ttgactgctt tcac 24

<210> SEQ ID NO 269
<211> LENGTH: 25
<212> TYPE: DNA
<213> ORGANISM: Artificial Sequence
<220> FEATURE:
<223> OTHER INFORMATION: Synthetic primer

<400> SEQUENCE: 269
tgtgtcattc cattttgttt ctgga 25

<210> SEQ ID NO 270
<211> LENGTH: 20
<212> TYPE: DNA
<213> ORGANISM: Artificial Sequence
<220> FEATURE:
<223> OTHER INFORMATION: Synthetic primer

<400> SEQUENCE: 270
ccttccttca gacccagacg 20

<210> SEQ ID NO 271
<211> LENGTH: 24
<212> TYPE: DNA
<213> ORGANISM: Artificial Sequence
<220> FEATURE:
<223> OTHER INFORMATION: Synthetic primer

<400> SEQUENCE: 271
ggccagacta aagtggaaga atgt 24

<210> SEQ ID NO 272
<211> LENGTH: 26
<212> TYPE: DNA
<213> ORGANISM: Artificial Sequence
<220> FEATURE:
<223> OTHER INFORMATION: Synthetic primer

<400> SEQUENCE: 272
tctgaaacta ggtgtgtatt gtttga 26

<210> SEQ ID NO 273
<211> LENGTH: 23
<212> TYPE: DNA
<213> ORGANISM: Artificial Sequence
<220> FEATURE:
<223> OTHER INFORMATION: Synthetic primer

<400> SEQUENCE: 273
tgggattcaa aatgtaaggg gaa 23

<210> SEQ ID NO 274
<211> LENGTH: 23
<212> TYPE: DNA
<213> ORGANISM: Artificial Sequence
<220> FEATURE:
<223> OTHER INFORMATION: Synthetic primer

<400> SEQUENCE: 274
atatgcatca ggtgcaagtt tct 23

<210> SEQ ID NO 275
<211> LENGTH: 23
<212> TYPE: DNA
<213> ORGANISM: Artificial Sequence
<220> FEATURE:
<223> OTHER INFORMATION: Synthetic primer

<400> SEQUENCE: 275
agagcagcaa acaacttctt cag 23

<210> SEQ ID NO 276
<211> LENGTH: 24
<212> TYPE: DNA
<213> ORGANISM: Artificial Sequence
<220> FEATURE:
<223> OTHER INFORMATION: Synthetic primer

<400> SEQUENCE: 276
cgccatgtgt ctcagtacat ttct 24

<210> SEQ ID NO 277
<211> LENGTH: 26
<212> TYPE: DNA
<213> ORGANISM: Artificial Sequence
<220> FEATURE:
<223> OTHER INFORMATION: Synthetic primer

<400> SEQUENCE: 277
atcgtagaaa ttccccttat agtcag 26

<210> SEQ ID NO 278
<211> LENGTH: 23
<212> TYPE: DNA
<213> ORGANISM: Artificial Sequence
<220> FEATURE:
<223> OTHER INFORMATION: Synthetic primer

<400> SEQUENCE: 278
agatcttgct ttgggatcac att 23

<210> SEQ ID NO 279
<211> LENGTH: 23
<212> TYPE: DNA
<213> ORGANISM: Artificial Sequence
<220> FEATURE:
<223> OTHER INFORMATION: Synthetic primer

<400> SEQUENCE: 279
ggttaagctt tgtggatgta gcc 23

<210> SEQ ID NO 280
<211> LENGTH: 22
<212> TYPE: DNA
<213> ORGANISM: Artificial Sequence
<220> FEATURE:
<223> OTHER INFORMATION: Synthetic primer

<400> SEQUENCE: 280
gttaatctgc cctgtgcctt tg 22

<210> SEQ ID NO 281
<211> LENGTH: 19
<212> TYPE: DNA
<213> ORGANISM: Artificial Sequence
<220> FEATURE:
<223> OTHER INFORMATION: Synthetic primer

<400> SEQUENCE: 281
gctgagcccc agcagaaag 19

<210> SEQ ID NO 282
<211> LENGTH: 21
<212> TYPE: DNA
<213> ORGANISM: Artificial Sequence
<220> FEATURE:
<223> OTHER INFORMATION: Synthetic primer

<400> SEQUENCE: 282
gcaaaagcac cacagagaca g 21

<210> SEQ ID NO 283
<211> LENGTH: 24
<212> TYPE: DNA
<213> ORGANISM: Artificial Sequence
<220> FEATURE:
<223> OTHER INFORMATION: Synthetic primer

<400> SEQUENCE: 283
gccagtgatt acatccagtc agta 24

<210> SEQ ID NO 284
<211> LENGTH: 18
<212> TYPE: DNA
<213> ORGANISM: Artificial Sequence
<220> FEATURE:
<223> OTHER INFORMATION: Synthetic primer

<400> SEQUENCE: 284
gcttgtggtg gaggtgct 18

<210> SEQ ID NO 285
<211> LENGTH: 19
<212> TYPE: DNA
<213> ORGANISM: Artificial Sequence
<220> FEATURE:
<223> OTHER INFORMATION: Synthetic primer

<400> SEQUENCE: 285
ccaggaagtg caggctcat 19

<210> SEQ ID NO 286
<211> LENGTH: 18
<212> TYPE: DNA
<213> ORGANISM: Artificial Sequence
<220> FEATURE:
<223> OTHER INFORMATION: Synthetic primer

<400> SEQUENCE: 286
ggaagagggc cagtggag 18

<210> SEQ ID NO 287
<211> LENGTH: 18
<212> TYPE: DNA
<213> ORGANISM: Artificial Sequence
<220> FEATURE:
<223> OTHER INFORMATION: Synthetic primer

<400> SEQUENCE: 287
ctgtgggacc ccttcagc 18

<210> SEQ ID NO 288

<211> LENGTH: 21
<212> TYPE: DNA
<213> ORGANISM: Artificial Sequence
<220> FEATURE:
<223> OTHER INFORMATION: Synthetic primer

<400> SEQUENCE: 288
cacactcgat gaggatggag c 21

<210> SEQ ID NO 289
<211> LENGTH: 21
<212> TYPE: DNA
<213> ORGANISM: Artificial Sequence
<220> FEATURE:
<223> OTHER INFORMATION: Synthetic primer

<400> SEQUENCE: 289
ccccttccca cttcacagat g 21

<210> SEQ ID NO 290
<211> LENGTH: 20
<212> TYPE: DNA
<213> ORGANISM: Artificial Sequence
<220> FEATURE:
<223> OTHER INFORMATION: Synthetic primer

<400> SEQUENCE: 290
cagggccgag ttgaaatccc 20

<210> SEQ ID NO 291
<211> LENGTH: 21
<212> TYPE: DNA
<213> ORGANISM: Artificial Sequence
<220> FEATURE:
<223> OTHER INFORMATION: Synthetic primer

<400> SEQUENCE: 291
caagaacctc aaccagccca a 21

<210> SEQ ID NO 292
<211> LENGTH: 22
<212> TYPE: DNA
<213> ORGANISM: Artificial Sequence
<220> FEATURE:
<223> OTHER INFORMATION: Synthetic primer

<400> SEQUENCE: 292
cgaccccctt cttctctttc tg 22

<210> SEQ ID NO 293
<211> LENGTH: 16
<212> TYPE: DNA
<213> ORGANISM: Artificial Sequence
<220> FEATURE:
<223> OTHER INFORMATION: Synthetic primer

<400> SEQUENCE: 293
cttcccccgc gaggtc 16

<210> SEQ ID NO 294
<211> LENGTH: 16
<212> TYPE: DNA
<213> ORGANISM: Artificial Sequence
<220> FEATURE:
<223> OTHER INFORMATION: Synthetic primer

<400> SEQUENCE: 294
gcaccctccc cccaca 16

<210> SEQ ID NO 295
<211> LENGTH: 19
<212> TYPE: DNA
<213> ORGANISM: Artificial Sequence
<220> FEATURE:
<223> OTHER INFORMATION: Synthetic primer

<400> SEQUENCE: 295
atgcagagga gcacgggta 19

<210> SEQ ID NO 296
<211> LENGTH: 19
<212> TYPE: DNA
<213> ORGANISM: Artificial Sequence
<220> FEATURE:
<223> OTHER INFORMATION: Synthetic primer

<400> SEQUENCE: 296
ctccgaggct acggggaat 19

<210> SEQ ID NO 297
<211> LENGTH: 19
<212> TYPE: DNA
<213> ORGANISM: Artificial Sequence
<220> FEATURE:
<223> OTHER INFORMATION: Synthetic primer

<400> SEQUENCE: 297
cgcttaagaa gcccaaccg 19

<210> SEQ ID NO 298
<211> LENGTH: 21
<212> TYPE: DNA
<213> ORGANISM: Artificial Sequence
<220> FEATURE:
<223> OTHER INFORMATION: Synthetic primer

<400> SEQUENCE: 298
cttcttcccg tagagcttgg c 21

<210> SEQ ID NO 299
<211> LENGTH: 23
<212> TYPE: DNA
<213> ORGANISM: Artificial Sequence
<220> FEATURE:
<223> OTHER INFORMATION: Synthetic primer

<400> SEQUENCE: 299
atgagtttgg tagcgaggag aac 23

<210> SEQ ID NO 300
<211> LENGTH: 24
<212> TYPE: DNA
<213> ORGANISM: Artificial Sequence
<220> FEATURE:
<223> OTHER INFORMATION: Synthetic primer

<400> SEQUENCE: 300
gctcagcttc tccttctgaa tctt 24

<210> SEQ ID NO 301
<211> LENGTH: 22
<212> TYPE: DNA

-continued

<213> ORGANISM: Artificial Sequence
<220> FEATURE:
<223> OTHER INFORMATION: Synthetic primer

<400> SEQUENCE: 301
gtatgaaacc acccaactgc aa 22

<210> SEQ ID NO 302
<211> LENGTH: 20
<212> TYPE: DNA
<213> ORGANISM: Artificial Sequence
<220> FEATURE:
<223> OTHER INFORMATION: Synthetic primer

<400> SEQUENCE: 302
agagatctgg ggcacctctg 20

<210> SEQ ID NO 303
<211> LENGTH: 19
<212> TYPE: DNA
<213> ORGANISM: Artificial Sequence
<220> FEATURE:
<223> OTHER INFORMATION: Synthetic primer

<400> SEQUENCE: 303
ctgacacccc tccagcaac 19

<210> SEQ ID NO 304
<211> LENGTH: 19
<212> TYPE: DNA
<213> ORGANISM: Artificial Sequence
<220> FEATURE:
<223> OTHER INFORMATION: Synthetic primer

<400> SEQUENCE: 304
gaggaagagg gtgcctcca 19

<210> SEQ ID NO 305
<211> LENGTH: 19
<212> TYPE: DNA
<213> ORGANISM: Artificial Sequence
<220> FEATURE:
<223> OTHER INFORMATION: Synthetic primer

<400> SEQUENCE: 305
ctcaggggtg ccggtcaat 19

<210> SEQ ID NO 306
<211> LENGTH: 22
<212> TYPE: DNA
<213> ORGANISM: Artificial Sequence
<220> FEATURE:
<223> OTHER INFORMATION: Synthetic primer

<400> SEQUENCE: 306
ccccataaga ggacacagct tc 22

<210> SEQ ID NO 307
<211> LENGTH: 23
<212> TYPE: DNA
<213> ORGANISM: Artificial Sequence
<220> FEATURE:
<223> OTHER INFORMATION: Synthetic primer

<400> SEQUENCE: 307
gtcggacagt gaacacaact tcc 23

-continued

<210> SEQ ID NO 308
<211> LENGTH: 21
<212> TYPE: DNA
<213> ORGANISM: Artificial Sequence
<220> FEATURE:
<223> OTHER INFORMATION: Synthetic primer

<400> SEQUENCE: 308
ttgggctggt tgaggttctt g 21

<210> SEQ ID NO 309
<211> LENGTH: 19
<212> TYPE: DNA
<213> ORGANISM: Artificial Sequence
<220> FEATURE:
<223> OTHER INFORMATION: Synthetic primer

<400> SEQUENCE: 309
cttccagggt gcagggtct 19

<210> SEQ ID NO 310
<211> LENGTH: 21
<212> TYPE: DNA
<213> ORGANISM: Artificial Sequence
<220> FEATURE:
<223> OTHER INFORMATION: Synthetic primer

<400> SEQUENCE: 310
gtgacatgtg ggcagcaaaa g 21

<210> SEQ ID NO 311
<211> LENGTH: 22
<212> TYPE: DNA
<213> ORGANISM: Artificial Sequence
<220> FEATURE:
<223> OTHER INFORMATION: Synthetic primer

<400> SEQUENCE: 311
catgtccccc aagaggacta ac 22

<210> SEQ ID NO 312
<211> LENGTH: 20
<212> TYPE: DNA
<213> ORGANISM: Artificial Sequence
<220> FEATURE:
<223> OTHER INFORMATION: Synthetic primer

<400> SEQUENCE: 312
ccgtcctcca gagtgggaag 20

<210> SEQ ID NO 313
<211> LENGTH: 19
<212> TYPE: DNA
<213> ORGANISM: Artificial Sequence
<220> FEATURE:
<223> OTHER INFORMATION: Synthetic primer

<400> SEQUENCE: 313
tttggtctgc ccctgggat 19

<210> SEQ ID NO 314
<211> LENGTH: 23
<212> TYPE: DNA
<213> ORGANISM: Artificial Sequence
<220> FEATURE:

-continued

<223> OTHER INFORMATION: Synthetic primer

<400> SEQUENCE: 314
tccaggaagt tgtgttcact gtc 23

<210> SEQ ID NO 315
<211> LENGTH: 19
<212> TYPE: DNA
<213> ORGANISM: Artificial Sequence
<220> FEATURE:
<223> OTHER INFORMATION: Synthetic primer

<400> SEQUENCE: 315
caggcagctt cccactctg 19

<210> SEQ ID NO 316
<211> LENGTH: 22
<212> TYPE: DNA
<213> ORGANISM: Artificial Sequence
<220> FEATURE:
<223> OTHER INFORMATION: Synthetic primer

<400> SEQUENCE: 316
ctttcatggg gttccacagc tt 22

<210> SEQ ID NO 317
<211> LENGTH: 17
<212> TYPE: DNA
<213> ORGANISM: Artificial Sequence
<220> FEATURE:
<223> OTHER INFORMATION: Synthetic primer

<400> SEQUENCE: 317
ccagcaggag gccaagc 17

<210> SEQ ID NO 318
<211> LENGTH: 21
<212> TYPE: DNA
<213> ORGANISM: Artificial Sequence
<220> FEATURE:
<223> OTHER INFORMATION: Synthetic primer

<400> SEQUENCE: 318
ctgtaggggc cagtgacctt c 21

<210> SEQ ID NO 319
<211> LENGTH: 20
<212> TYPE: DNA
<213> ORGANISM: Artificial Sequence
<220> FEATURE:
<223> OTHER INFORMATION: Synthetic primer

<400> SEQUENCE: 319
gcagcagtgg cagttttgag 20

<210> SEQ ID NO 320
<211> LENGTH: 23
<212> TYPE: DNA
<213> ORGANISM: Artificial Sequence
<220> FEATURE:
<223> OTHER INFORMATION: Synthetic primer

<400> SEQUENCE: 320
ttgggaagca gatactcctt ggg 23

<210> SEQ ID NO 321
<211> LENGTH: 23
<212> TYPE: DNA
<213> ORGANISM: Artificial Sequence
<220> FEATURE:
<223> OTHER INFORMATION: Synthetic primer

<400> SEQUENCE: 321
gcccattcag atcaagaagt cca 23

<210> SEQ ID NO 322
<211> LENGTH: 23
<212> TYPE: DNA
<213> ORGANISM: Artificial Sequence
<220> FEATURE:
<223> OTHER INFORMATION: Synthetic primer

<400> SEQUENCE: 322
taggtgcaaa tagcgcaaga gaa 23

<210> SEQ ID NO 323
<211> LENGTH: 21
<212> TYPE: DNA
<213> ORGANISM: Artificial Sequence
<220> FEATURE:
<223> OTHER INFORMATION: Synthetic primer

<400> SEQUENCE: 323
tctgtggtca tggaaggagg g 21

<210> SEQ ID NO 324
<211> LENGTH: 18
<212> TYPE: DNA
<213> ORGANISM: Artificial Sequence
<220> FEATURE:
<223> OTHER INFORMATION: Synthetic primer

<400> SEQUENCE: 324
atggcggtct gcaagctg 18

<210> SEQ ID NO 325
<211> LENGTH: 18
<212> TYPE: DNA
<213> ORGANISM: Artificial Sequence
<220> FEATURE:
<223> OTHER INFORMATION: Synthetic primer

<400> SEQUENCE: 325
ggccaccact gccagaac 18

<210> SEQ ID NO 326
<211> LENGTH: 18
<212> TYPE: DNA
<213> ORGANISM: Artificial Sequence
<220> FEATURE:
<223> OTHER INFORMATION: Synthetic primer

<400> SEQUENCE: 326
ctggccctga agccctct 18

<210> SEQ ID NO 327
<211> LENGTH: 19
<212> TYPE: DNA
<213> ORGANISM: Artificial Sequence
<220> FEATURE:
<223> OTHER INFORMATION: Synthetic primer

<400> SEQUENCE: 327
gggaacaaca gcaggggac 19

<210> SEQ ID NO 328
<211> LENGTH: 19
<212> TYPE: DNA
<213> ORGANISM: Artificial Sequence
<220> FEATURE:
<223> OTHER INFORMATION: Synthetic primer

<400> SEQUENCE: 328
tcccctcctt ccatgacca 19

<210> SEQ ID NO 329
<211> LENGTH: 22
<212> TYPE: DNA
<213> ORGANISM: Artificial Sequence
<220> FEATURE:
<223> OTHER INFORMATION: Synthetic primer

<400> SEQUENCE: 329
ctccttcaga gccttctgct cc 22

<210> SEQ ID NO 330
<211> LENGTH: 23
<212> TYPE: DNA
<213> ORGANISM: Artificial Sequence
<220> FEATURE:
<223> OTHER INFORMATION: Synthetic primer

<400> SEQUENCE: 330
ggcctggact tcttgatctg aat 23

<210> SEQ ID NO 331
<211> LENGTH: 20
<212> TYPE: DNA
<213> ORGANISM: Artificial Sequence
<220> FEATURE:
<223> OTHER INFORMATION: Synthetic primer

<400> SEQUENCE: 331
ccaaggcaaa gaccccaaca 20

<210> SEQ ID NO 332
<211> LENGTH: 20
<212> TYPE: DNA
<213> ORGANISM: Artificial Sequence
<220> FEATURE:
<223> OTHER INFORMATION: Synthetic primer

<400> SEQUENCE: 332
caggcgagaa aggatgggag 20

<210> SEQ ID NO 333
<211> LENGTH: 22
<212> TYPE: DNA
<213> ORGANISM: Artificial Sequence
<220> FEATURE:
<223> OTHER INFORMATION: Synthetic primer

<400> SEQUENCE: 333
aggtcatgtg ttttgggtgc tc 22

<210> SEQ ID NO 334
<211> LENGTH: 22

-continued

<212> TYPE: DNA
<213> ORGANISM: Artificial Sequence
<220> FEATURE:
<223> OTHER INFORMATION: Synthetic primer

<400> SEQUENCE: 334
cgctaccaaa ctcatccgtg tt 22

<210> SEQ ID NO 335
<211> LENGTH: 17
<212> TYPE: DNA
<213> ORGANISM: Artificial Sequence
<220> FEATURE:
<223> OTHER INFORMATION: Synthetic primer

<400> SEQUENCE: 335
atcctcggag cccgaca 17

<210> SEQ ID NO 336
<211> LENGTH: 23
<212> TYPE: DNA
<213> ORGANISM: Artificial Sequence
<220> FEATURE:
<223> OTHER INFORMATION: Synthetic primer

<400> SEQUENCE: 336
cttcttcttc tccttgggtg gtc 23

<210> SEQ ID NO 337
<211> LENGTH: 21
<212> TYPE: DNA
<213> ORGANISM: Artificial Sequence
<220> FEATURE:
<223> OTHER INFORMATION: Synthetic primer

<400> SEQUENCE: 337
ccagatctct ccccaagagg g 21

<210> SEQ ID NO 338
<211> LENGTH: 20
<212> TYPE: DNA
<213> ORGANISM: Artificial Sequence
<220> FEATURE:
<223> OTHER INFORMATION: Synthetic primer

<400> SEQUENCE: 338
ggtgacaagg cctcaggaag 20

<210> SEQ ID NO 339
<211> LENGTH: 21
<212> TYPE: DNA
<213> ORGANISM: Artificial Sequence
<220> FEATURE:
<223> OTHER INFORMATION: Synthetic primer

<400> SEQUENCE: 339
tactccactc agtgtccagg g 21

<210> SEQ ID NO 340
<211> LENGTH: 22
<212> TYPE: DNA
<213> ORGANISM: Artificial Sequence
<220> FEATURE:
<223> OTHER INFORMATION: Synthetic primer

<400> SEQUENCE: 340
tcctgagtac tgtccccaaa gg 22

<210> SEQ ID NO 341
<211> LENGTH: 23
<212> TYPE: DNA
<213> ORGANISM: Artificial Sequence
<220> FEATURE:
<223> OTHER INFORMATION: Synthetic primer

<400> SEQUENCE: 341
caagtacgct ctcccgtctt tta 23

<210> SEQ ID NO 342
<211> LENGTH: 19
<212> TYPE: DNA
<213> ORGANISM: Artificial Sequence
<220> FEATURE:
<223> OTHER INFORMATION: Synthetic primer

<400> SEQUENCE: 342
ctcggcaaac tcagcacca 19

<210> SEQ ID NO 343
<211> LENGTH: 22
<212> TYPE: DNA
<213> ORGANISM: Artificial Sequence
<220> FEATURE:
<223> OTHER INFORMATION: Synthetic primer

<400> SEQUENCE: 343
ctgaaaggta gtcctgggtt cc 22

<210> SEQ ID NO 344
<211> LENGTH: 22
<212> TYPE: DNA
<213> ORGANISM: Artificial Sequence
<220> FEATURE:
<223> OTHER INFORMATION: Synthetic primer

<400> SEQUENCE: 344
ccacagcttc tcctctgact tc 22

<210> SEQ ID NO 345
<211> LENGTH: 23
<212> TYPE: DNA
<213> ORGANISM: Artificial Sequence
<220> FEATURE:
<223> OTHER INFORMATION: Synthetic primer

<400> SEQUENCE: 345
atcaagcaag agccagtaga ccc 23

<210> SEQ ID NO 346
<211> LENGTH: 20
<212> TYPE: DNA
<213> ORGANISM: Artificial Sequence
<220> FEATURE:
<223> OTHER INFORMATION: Synthetic primer

<400> SEQUENCE: 346
cagacgagaa cacaccccag 20

<210> SEQ ID NO 347
<211> LENGTH: 19
<212> TYPE: DNA
<213> ORGANISM: Artificial Sequence
<220> FEATURE:
<223> OTHER INFORMATION: Synthetic primer

<400> SEQUENCE: 347
gagccgcaga accacttca 19

<210> SEQ ID NO 348
<211> LENGTH: 23
<212> TYPE: DNA
<213> ORGANISM: Artificial Sequence
<220> FEATURE:
<223> OTHER INFORMATION: Synthetic primer

<400> SEQUENCE: 348
taaaagacgg gagagcgtac ttg 23

<210> SEQ ID NO 349
<211> LENGTH: 23
<212> TYPE: DNA
<213> ORGANISM: Artificial Sequence
<220> FEATURE:
<223> OTHER INFORMATION: Synthetic primer

<400> SEQUENCE: 349 ttccccttc tctctctctt tag 23

<210> SEQ ID NO 350
<211> LENGTH: 21
<212> TYPE: DNA
<213> ORGANISM: Artificial Sequence
<220> FEATURE:
<223> OTHER INFORMATION: Synthetic primer

<400> SEQUENCE: 350
cttttggtct acccgccaag g 21

<210> SEQ ID NO 351
<211> LENGTH: 19
<212> TYPE: DNA
<213> ORGANISM: Artificial Sequence
<220> FEATURE:
<223> OTHER INFORMATION: Synthetic primer

<400> SEQUENCE: 351
aggctgtggt gttgtctgc 19

<210> SEQ ID NO 352
<211> LENGTH: 20
<212> TYPE: DNA
<213> ORGANISM: Artificial Sequence
<220> FEATURE:
<223> OTHER INFORMATION: Synthetic primer

<400> SEQUENCE: 352
cagcaccgag tagctctcca 20

<210> SEQ ID NO 353
<211> LENGTH: 24
<212> TYPE: DNA
<213> ORGANISM: Artificial Sequence
<220> FEATURE:
<223> OTHER INFORMATION: Synthetic primer

<400> SEQUENCE: 353
ctcatctttt gctcctgata gctc 24

<210> SEQ ID NO 354
<211> LENGTH: 23
<212> TYPE: DNA
<213> ORGANISM: Artificial Sequence
<220> FEATURE:
<223> OTHER INFORMATION: Synthetic primer

<400> SEQUENCE: 354
gccgcttgaa tactgactgg atg 23

<210> SEQ ID NO 355
<211> LENGTH: 21
<212> TYPE: DNA
<213> ORGANISM: Artificial Sequence
<220> FEATURE:
<223> OTHER INFORMATION: Synthetic primer

<400> SEQUENCE: 355
caaggctgag aacccactca c 21

<210> SEQ ID NO 356
<211> LENGTH: 23
<212> TYPE: DNA
<213> ORGANISM: Artificial Sequence
<220> FEATURE:
<223> OTHER INFORMATION: Synthetic primer

<400> SEQUENCE: 356
ctttctctgc ccttccctga tac 23

<210> SEQ ID NO 357
<211> LENGTH: 19
<212> TYPE: DNA
<213> ORGANISM: Artificial Sequence
<220> FEATURE:
<223> OTHER INFORMATION: Synthetic primer

<400> SEQUENCE: 357
caggctgttc ccacagacg 19

<210> SEQ ID NO 358
<211> LENGTH: 23
<212> TYPE: DNA
<213> ORGANISM: Artificial Sequence
<220> FEATURE:
<223> OTHER INFORMATION: Synthetic primer

<400> SEQUENCE: 358
ctactggctc ttgcttgatg gat 23

<210> SEQ ID NO 359
<211> LENGTH: 21
<212> TYPE: DNA
<213> ORGANISM: Artificial Sequence
<220> FEATURE:
<223> OTHER INFORMATION: Synthetic primer

<400> SEQUENCE: 359
atactgctcg cctggaagat g 21

<210> SEQ ID NO 360
<211> LENGTH: 20
<212> TYPE: DNA
<213> ORGANISM: Artificial Sequence
<220> FEATURE:
<223> OTHER INFORMATION: Synthetic primer

<400> SEQUENCE: 360
cagtgtgtca aggtcttcgc 20

<210> SEQ ID NO 361
<211> LENGTH: 23
<212> TYPE: DNA
<213> ORGANISM: Artificial Sequence
<220> FEATURE:
<223> OTHER INFORMATION: Synthetic primer

<400> SEQUENCE: 361
cacaggtgac caacgaggaa ata 23

<210> SEQ ID NO 362
<211> LENGTH: 20
<212> TYPE: DNA
<213> ORGANISM: Artificial Sequence
<220> FEATURE:
<223> OTHER INFORMATION: Synthetic primer

<400> SEQUENCE: 362
acaggtgggg ctatgacagg 20

<210> SEQ ID NO 363
<211> LENGTH: 23
<212> TYPE: DNA
<213> ORGANISM: Artificial Sequence
<220> FEATURE:
<223> OTHER INFORMATION: Synthetic primer

<400> SEQUENCE: 363
aagaagaaga agctcccaac acc 23

<210> SEQ ID NO 364
<211> LENGTH: 20
<212> TYPE: DNA
<213> ORGANISM: Artificial Sequence
<220> FEATURE:
<223> OTHER INFORMATION: Synthetic primer

<400> SEQUENCE: 364
ggatgagcct gcacttcctg 20

<210> SEQ ID NO 365
<211> LENGTH: 23
<212> TYPE: DNA
<213> ORGANISM: Artificial Sequence
<220> FEATURE:
<223> OTHER INFORMATION: Synthetic primer

<400> SEQUENCE: 365
taacatccct ccttccaaga cct 23

<210> SEQ ID NO 366
<211> LENGTH: 20
<212> TYPE: DNA
<213> ORGANISM: Artificial Sequence
<220> FEATURE:
<223> OTHER INFORMATION: Synthetic primer

<400> SEQUENCE: 366
gggcacagaa gtccatgcag 20

<210> SEQ ID NO 367

<211> LENGTH: 21
<212> TYPE: DNA
<213> ORGANISM: Artificial Sequence
<220> FEATURE:
<223> OTHER INFORMATION: Synthetic primer

<400> SEQUENCE: 367
ctgcccccta ctcaggaaat g 21

<210> SEQ ID NO 368
<211> LENGTH: 22
<212> TYPE: DNA
<213> ORGANISM: Artificial Sequence
<220> FEATURE:
<223> OTHER INFORMATION: Synthetic primer

<400> SEQUENCE: 368
gggagacatg tttgctggtt ct 22

<210> SEQ ID NO 369
<211> LENGTH: 23
<212> TYPE: DNA
<213> ORGANISM: Artificial Sequence
<220> FEATURE:
<223> OTHER INFORMATION: Synthetic primer

<400> SEQUENCE: 369
caccctgacc aaggaagaca atc 23

<210> SEQ ID NO 370
<211> LENGTH: 16
<212> TYPE: DNA
<213> ORGANISM: Artificial Sequence
<220> FEATURE:
<223> OTHER INFORMATION: Synthetic primer

<400> SEQUENCE: 370
caggcgtcgg acctcg 16

<210> SEQ ID NO 371
<211> LENGTH: 20
<212> TYPE: DNA
<213> ORGANISM: Artificial Sequence
<220> FEATURE:
<223> OTHER INFORMATION: Synthetic primer

<400> SEQUENCE: 371
cttctcattc caccccccag 20

<210> SEQ ID NO 372
<211> LENGTH: 20
<212> TYPE: DNA
<213> ORGANISM: Artificial Sequence
<220> FEATURE:
<223> OTHER INFORMATION: Synthetic primer

<400> SEQUENCE: 372
cccaggcttc agggaactca 20

<210> SEQ ID NO 373
<211> LENGTH: 21
<212> TYPE: DNA
<213> ORGANISM: Artificial Sequence
<220> FEATURE:
<223> OTHER INFORMATION: Synthetic primer

<400> SEQUENCE: 373
cgttccccca agcaaatcaa g 21

<210> SEQ ID NO 374
<211> LENGTH: 23
<212> TYPE: DNA
<213> ORGANISM: Artificial Sequence
<220> FEATURE:
<223> OTHER INFORMATION: Synthetic primer

<400> SEQUENCE: 374
gggtgtgtcc aggtacttaa gag 23

<210> SEQ ID NO 375
<211> LENGTH: 23
<212> TYPE: DNA
<213> ORGANISM: Artificial Sequence
<220> FEATURE:
<223> OTHER INFORMATION: Synthetic primer

<400> SEQUENCE: 375
ggcagtttga ggctgaattt gga 23

<210> SEQ ID NO 376
<211> LENGTH: 22
<212> TYPE: DNA
<213> ORGANISM: Artificial Sequence
<220> FEATURE:
<223> OTHER INFORMATION: Synthetic primer

<400> SEQUENCE: 376
tccctcctct gaatggaagc ag 22

<210> SEQ ID NO 377
<211> LENGTH: 23
<212> TYPE: DNA
<213> ORGANISM: Artificial Sequence
<220> FEATURE:
<223> OTHER INFORMATION: Synthetic primer

<400> SEQUENCE: 377
actccagaac gaagggatat tgc 23

<210> SEQ ID NO 378
<211> LENGTH: 20
<212> TYPE: DNA
<213> ORGANISM: Artificial Sequence
<220> FEATURE:
<223> OTHER INFORMATION: Synthetic primer

<400> SEQUENCE: 378
cggaacttgc gaggtgtctt 20

<210> SEQ ID NO 379
<211> LENGTH: 23
<212> TYPE: DNA
<213> ORGANISM: Artificial Sequence
<220> FEATURE:
<223> OTHER INFORMATION: Synthetic primer

<400> SEQUENCE: 379
cgtgtactcc taccactcct act 23

<210> SEQ ID NO 380
<211> LENGTH: 23
<212> TYPE: DNA

<213> ORGANISM: Artificial Sequence
<220> FEATURE:
<223> OTHER INFORMATION: Synthetic primer

<400> SEQUENCE: 380
gtctggcttc ttctcaaaac tgc 23

<210> SEQ ID NO 381
<211> LENGTH: 23
<212> TYPE: DNA
<213> ORGANISM: Artificial Sequence
<220> FEATURE:
<223> OTHER INFORMATION: Synthetic primer

<400> SEQUENCE: 381
agttgttctc ctttggggtt ctg 23

<210> SEQ ID NO 382
<211> LENGTH: 20
<212> TYPE: DNA
<213> ORGANISM: Artificial Sequence
<220> FEATURE:
<223> OTHER INFORMATION: Synthetic primer

<400> SEQUENCE: 382
tgagtgggct caacactcac 20

<210> SEQ ID NO 383
<211> LENGTH: 26
<212> TYPE: DNA
<213> ORGANISM: Artificial Sequence
<220> FEATURE:
<223> OTHER INFORMATION: Synthetic primer

<400> SEQUENCE: 383
ttccaaaaat gtttactctc tgtgtt 26

<210> SEQ ID NO 384
<211> LENGTH: 23
<212> TYPE: DNA
<213> ORGANISM: Artificial Sequence
<220> FEATURE:
<223> OTHER INFORMATION: Synthetic primer

<400> SEQUENCE: 384
aatgagaggc gcttaatatc cgt 23

<210> SEQ ID NO 385
<211> LENGTH: 23
<212> TYPE: DNA
<213> ORGANISM: Artificial Sequence
<220> FEATURE:
<223> OTHER INFORMATION: Synthetic primer

<400> SEQUENCE: 385
ccggatcgag aaggtcatct aca 23

<210> SEQ ID NO 386
<211> LENGTH: 16
<212> TYPE: DNA
<213> ORGANISM: Artificial Sequence -continued

```
<220> FEATURE:
<223> OTHER INFORMATION: Synthetic primer

<400> SEQUENCE: 386

acccacctgg ccccac                                                    16
```

RECURRENT MUTATIONS IN EPIGENETIC REGULATORS, *RHOA* AND *FYN* KINASE IN PERIPHERAL T-CELL LYMPHOMAS

CROSS-REFERENCE TO RELATED APPLICATIONS

This application is a 371 national stage application of PCT Application No. PCT/US14/40647, filed Jun. 3, 2014, and claims the benefit of U.S. Provisional Application No. 61/830,631, filed on Jun. 3, 2013; the entire contents of which are hereby incorporated by reference as if fully set forth herein.

STATEMENT REGARDING FEDERALLY SPONSORED RESEARCH

This invention was made with government support under CA121852 awarded by the National Institutes of Health. The government has certain rights in the invention.

BACKGROUND

Lymphoma is the most common blood cancer. The two main forms of lymphoma are Hodgkin lymphoma (HL) and non-Hodgkin lymphoma (NHL). Lymphoma occurs when lymphocytes, a type of white blood cell, grow abnormally. The body has two main types of lymphocytes that can develop into lymphomas: B-lymphocytes (B-cells) and T-lymphocytes (T-cells). Cancerous lymphocytes can travel to many parts of the body, including the lymph nodes, spleen, bone marrow, blood or other organs, and can accumulate to form tumors. Peripheral T-cell lymphomas (PTCLs) are a heterogeneous and poorly understood group of aggressive non-Hodgkin lymphomas that develop from mature-stage white blood cells called T-cells and natural killer cells with dismal prognosis.

PTCLs represent a spectrum of T-cell lymphomas and accounts for approximately 10 percent to 15 percent of all NHL cases in the United States. PTCLs include Peripheral T-cell lymphoma not otherwise specified (PTCL-NOS), Anaplastic Large-Cell Lymphoma (ALCL), Angioimmunoblastic T-Cell Lymphoma (AITL), Enteropathy-Type T-Cell Lymphoma, Nasal NK/T-Cell Lymphoma, Hepatosplenic Gamma-Delta T-Cell Lymphoma Cutaneous T-cell Lymphomas (CTCL) and others.

PTCL-NOS and AITL and are the most common groups of PTCL accounting for 25% and 18% of all PTCLs, respectively. Additional, less frequent pathologic entities include ALK+ and ALK− anaplastic large cell lymphomas (ALCL), hepatosplenic γδ T-cell lymphomas, enteropathy associated T-cell lymphomas (EATL), nasal type NK-/T-cell lymphomas, panniculitis-like T-cell lymphomas and leukemic forms of PTCL such as HTLV1+ adult T-cell leukemia/lymphoma, T-cell chronic large granular lymphocytic leukemia, aggressive NK-cell leukemia and T-cell prolymphocytic leukemia.

For most subtypes of PTCL, the frontline treatment regimen is typically a combination chemotherapy, such as CHOP (cyclophosphamide, doxorubicin, vincristine, and prednisone) or EPOCH (etoposide, vincristine, doxorubicin, cyclophosphamide, and prednisone) or other multi-drug regimens. Because most PTCL patients will relapse, some oncologists recommend giving high-dose chemotherapy followed by an autologous stem cell transplant to some patients who had a good response to their initial chemotherapy program.

Currently a need exists for the early identification of individuals having PTCL in order to offer earlier diagnosis and alternative treatment options. It has been discovered that there is a correlation of certain mutations with the occurrence of PTCL. The identification of these genetic mutations involved in the pathogenesis of and PTCL in screening and diagnostic assays is helpful for early identification and diagnosis of PTCL.

SUMMARY OF THE INVENTION

It has been discovered that certain mutations in PTCL transformation correlate with PTCL. Whole exome sequencing has identified genetic alterations in PTCL transformation including highly recurrent epigenetic factor mutations in TET2, DNMT3A, and IDH2 as well as RHOA, more specifically RHOA p.Gly17Val. Less frequent genetic defects were also identified, including mutations in FYN, ATM, B2M, and CD58 implicating SRC signaling, impaired DNA damage response and escape from immune surveillance mechanisms in the pathogenesis of PTCL. Given these correlations of mutations with the occurrence of PTCL, in various embodiments, a subject who is being screened or diagnosed with PTCL, is tested for the occurrence of one or more of these mutations.

Specifically, in certain embodiments, methods are provided for determining whether a subject has an increased risk of developing PTCL. A biological sample from a subject that does not have lymphoma but may be suspected of having lymphoma is provided. The biological sample is analyzed for the presence of one or more mutations selected from the group consisting of RHOA p.Gly17Val, RHOA p.Cys16Arg, RHOA p.Thr19Ile, RHOA p.Gly17Glu, RHOA p.Asp120Tyr, FYN p.Leu174Arg, FYN p.Arg176Cys, and FYN p.Tyr531His.

If it is determined that the subject has an increased risk of developing PTCL due to the presence of a mutation selected from the group consisting of FYN p.Leu174Arg, FYN p.Arg176Cys, and FYN p.Tyr531His, then it is desirable to prophylactically treat the subject for PTCL by administering a therapeutically effective amount of an SRC kinase inhibitor (e.g., Bosutinib (SKI-606); Saracatinib (AZD0530); Dasatinib (BMS354825); KX2-391; XL-228, JNJ-26483327, A 419259 trihydrochloride; AZM 475271; Damnacanthal, Herbimycin A, Lavendustin A, MNS, 1-Naphthyl PP1 D 166285 dihydrochloride, PP 1, PP 2, SRC I1, KX2-391 (KX01) and NVP-BHG712). In these methods, the biological sample may be lymphoma tumor, bone marrow, serum, blood, cerebrospinal fluid and plasma. Preferably, the subject is human.

In certain embodiments, methods are provided for diagnosing whether a subject has PTCL. A biological sample from a subject having lymphoma is provided. The biological sample is analyzed for the presence of one or more mutations selected from the group consisting of RHOA p.Gly17Val, RHOA p.Cys16Arg, RHOA p.Thr19Ile, RHOA p.Gly17Glu, RHOA p.Asp120Tyr, FYN p.Leu174Arg, FYN p.Arg176Cys, and FYN p.Tyr531His. If it is determined that the subject has PTCL if it is determined that the subject has an increased risk of developing Peripheral T-Cell Lymphoma due to the presence of a mutation selected from the group consisting of FYN p.Leu174Arg, FYN p.Arg176Cys, and FYN p.Tyr531His, then treating the subject for Peripheral T-Cell Lymphoma by administering a therapeutically effective amount of an SRC kinase inhibitor (e.g., Bosutinib (SKI-606); Saracatinib (AZD0530); Dasatinib (BMS354825); KX2-391; XL-228, JNJ-26483327, A 419259 trihydrochloride; AZM 475271; Damnacanthal, Herbimycin A, Lavendustin A, MNS, 1-Naphthyl PP1 D 166285 dihydrochloride, PP 1, PP 2, SRC I1, KX2-391 (KX01) and NVP-BHG712). In these methods, the biological sample may be lymphoma tumor, bone marrow, serum, blood, cerebrospinal fluid and plasma. Preferably, the subject is human.

In certain embodiments, it is possible to determine that the PTCLs have approximately about a 70% probability of being AITL if the RHOA p.Gly17Val mutation is detected.

In other embodiments, methods are provided for treating a subject having PTCL, due to the presence of a mutation selected from the group consisting of FYN p.Leu174Arg, FYN p.Arg176Cys, and FYN p.Tyr531His comprising administering a therapeutically effective amount of an SRC kinase inhibitor (e.g., Bosutinib (SKI-606); Saracatinib (AZD0530); Dasatinib (BMS354825); KX2-391; XL-228, JNJ-26483327, A 419259 trihydrochloride; AZM 475271; Damnacanthal, Herbimycin A, Lavendustin A, MNS, 1-Naphthyl PP1 D 166285 dihydrochloride, PP 1, PP 2, SRC I1, KX2-391 (KX01) and NVP-BHG712). In these methods, the biological sample may be lymphoma tumor, bone marrow, serum, blood, cerebrospinal fluid and plasma. Preferably, the subject is human.

In certain embodiments, microarrays comprise two or more oligonucleotides bound to a support that are complementary to and hybridize to one or more respective target oligonucleotides selected from the group consisting of RHOA p.Gly17Val, RHOA p.Cys16Arg, RHOA p.Thr19Ile, RHOA p.Gly17Glu, RHOA p.Asp120Tyr, FYN p.Leu174Arg, FYN p.Arg176Cys, and FYN p.Tyr531His. Kits comprising these microarrays are provided.

Finally, in other embodiments, kits are provided comprising oligonucleotides that are complementary to and specifically hybridize to a target oligonucleotide SNP selected from the group consisting of RHOA p.Gly17Val, RHOA p.Cys16Arg, RHOA p.Thr19Ile, RHOA p.Gly17Glu, RHOA p.Asp120Tyr, FYN p.Leu174Arg, FYN p.Arg176Cys, and FYN p.Tyr531His. The kit further comprises enzymes suitable for amplifying nucleic acids, primers or probes that are labeled with a radioisotope, a fluorophore, a chromophore, a dye, an enzyme, or TOF carrier.

These and other features, embodiments, and advantages of the present invention will become better understood with regard to the following description, appended claims, and accompanying drawings.

BRIEF DESCRIPTION OF THE DRAWINGS

The following figures form part of the present specification and are included to further demonstrate certain embodiments of the present invention. The invention may be better understood by reference to one or more of these drawings in combination with the detailed description of specific embodiments presented herein.

DETAILED DESCRIPTION

1. Definitions

Figure 1A:
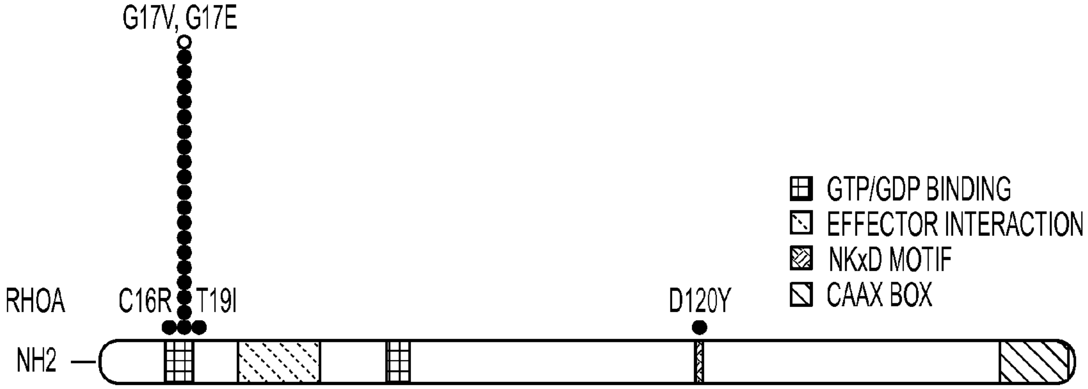
FIG. 1A-1D are schematic representations that show RHOA p.Gly17Val, p.Cys16Arg, p.Thr19Ile, p.Gly17Glu, p.Asp120Tyr, TET2, DNMT3A, IDH2 mutations in PTCLs and AITLs according to an embodiment.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference.

Generally, nomenclatures used in connection with, and techniques of, cell and tissue culture, molecular biology, immunology, microbiology, genetics, protein, and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lan, Antibodies: A Laboratory Manual, Cold Spring Harbor Laboratory Press, Cold Spring Harbor, N.Y. (1990); Principles of Neural Science, 4th ed., Eric R. Kandel, James H. Schwart, Thomas M. Jessell editors. McGraw-Hill/Appleton & Lange: New York, N.Y. (2000). Unless defined otherwise, all technical and scientific terms used herein have the same meaning as commonly understood by one of ordinary skill in the art.

Technical terms are also used according to conventional usage that may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The term "Peripheral T-Cell Lymphoma (PTCL-NOS)," as used herein, means a group of diseases that do not fit into any of the other subtypes of PTCL. PTCL-NOS is the most common subtype, making up about one quarter of all diagnosed PTCLs. It is also the most common of all the T-cell lymphomas. The term PTCL can be confusing as it can refer to the entire spectrum of mature T-cell lymphomas or sometimes to this specific subtype, PTCL-NOS, only. Although most patients with PTCL-NOS present with lymph node involvement, sites outside the lymph nodes, such as the liver, bone marrow, gastrointestinal tract and skin, may also be involved. This group of PTCLs is considered aggressive and requires standard combination chemotherapy upon diagnosis.

The term "Anaplastic Large-Cell Lymphoma (ALCL)," as used herein, means a rare type of aggressive T-cell lymphoma comprising only 3 percent of all lymphomas in adults (about 15 percent to 20 percent of all PTCLs) and between 10 percent and 30 percent of all lymphomas in children. ALCL can appear in the skin or in other organs throughout the body (systemic ALCL). Prognosis and treatment are different for each subtype. For more information, see LRFs ALCL Fact Sheet.

The term "Angioimmunoblastic T-Cell Lymphoma (AITL)," as used herein, means an often fast-growing T-cell lymphoma that accounts for between 1 percent and 2 percent of all NHL cases (about 15 percent to 20 percent of all PTCLs) in the United States. This type of lymphoma often responds to milder therapies, such as steroids, although it often progresses and requires chemotherapy and other medications. In advanced cases, bone marrow transplantation may be used. For more information, see LRF's AITL Fact Sheet.

The term "Enteropathy-Type T-Cell Lymphoma," as used herein, means an extremely rare subtype that appears in the intestines and is strongly associated with celiac disease.

The term "Nasal NK/T-Cell Lymphoma," as used herein, means the involvement of natural killer (NK) cells, which have specific jobs in the normal immune system. NK cells are closely related to T-cells and often have features that overlap with normal T-cells. If they become a cancer, they are called an NK or NK/T-cell lymphoma and are grouped with other forms of PTCL. Although this fast-growing lymphoma is very rare in the United States, it is more common in Asia and parts of Latin America, leading researchers to suspect that some ethnic groups may be more prone to this cancer. This type of lymphoma is associated with the Epstein-Barr virus and most often involves the nasal area, trachea, gastrointestinal tract or skin.

The term "Hepatosplenic Gamma-Delta T-Cell Lymphoma," as used herein, means an extremely rare and aggressive disease that starts in the liver or spleen.

The term "Cutaneous T-cell Lymphomas (CTCL)," as used herein, means a group of lymphomas that originate in the skin. CTCLs are a subset of PTCL as they are lymphomas of mature T-cells. However, these lymphomas are generally less aggressive, have a different prognosis, and have different treatment approaches than the aggressive PTCLs. Mycosis fungoides is the most common type of cutaneous T-cell lymphoma. It is generally a slow-growing cancer that starts in the skin, appearing as a scaly, red rash in areas of the body that are not usually exposed to the sun. Sézary Syndrome is an advanced, variant form of mycosis fungoides, and affects both the skin and the peripheral blood. It can cause widespread itching, reddening and peeling of the skin as well as skin tumors.

The term "allele," as used herein, means a particular form of a genetic locus, distinguished from other forms by its particular nucleotide sequence, or one of the alternative polymorphisms found at a polymorphic site.

The term "biological sample," as used herein, means a sample that may be extracted, untreated, treated, diluted, or concentrated form a patient. Any cell type or tissue may be use for diagnosis to determine the presence of a mutation or the identity of the allelic variant of a polymorphic region of the RHOA and FYN genes. A preferred sample is a lymphoma tumor sample, but samples can also be obtained from bone marrow, serum, blood, plasma and cerebrospinal fluid.

The term "exons," as used herein, mean short, functionally important sequences of DNA which represent the regions in genes that are translated into protein and the untranslated region (UTR) flanking them.

The term "exome sequencing" (also known as targeted exome capture), as used herein, means an efficient strategy to selectively sequence the coding regions of the genome as a cheaper but still effective alternative to whole genome sequencing. UTRs are usually not included in exome studies. In the human genome there are about 180,000 exons: these constitute about 1% of the human genome, which translates to about 30 megabases (Mb) in length. It is estimated that the protein coding regions of the human genome constitute about 85 percent of the disease-causing mutations.

The term "gene," as used herein, means one or more sequence(s) of nucleotides in a genome that together encode one or more expressed molecule, e.g., an RNA, or polypeptide. The gene can include coding sequences that are transcribed into RNA which may then be translated into a polypeptide sequence, and can include associated structural or regulatory sequences that aid in replication or expression of the gene.

The terms "genetic predisposition" and "at risk of developing a disease," as used herein, are used interchangeably herein and mean the susceptibility of a subject to lymphoma by virtue of the subject having one of the mutations described herein. A subject who is "at risk of developing a disease" means that the subject has a statistically higher likelihood or susceptibility to the disease condition than control. If a subject has a genetic predisposition to a disease, they do not necessarily develop the disease, but are at a higher than normal risk for developing the disease.

The terms "individual," "subject," or "patient" are used interchangeably and as used herein, mean any mammalian subject for whom diagnosis, treatment, or therapy is desired, particularly humans. A "subject" as used herein generally refers to any living multicellular organism. Subjects include, but are not limited to animals (e.g., cows, pigs, horses, donkeys, sheep, dogs, and cats), laboratory test animals (e.g., rabbits, mice, rats, guinea pigs, hamsters), and hominoids (e.g., humans, chimpanzees, and monkeys). The term includes transgenic and cloned species. The term "patient" refers to both human and veterinary subjects.

The term "isolated," as used herein, means material is substantially or essentially free from components that normally accompany it in its native state.

The term "kit," as used herein, means any manufacture (e.g. a package or container) comprising at least one reagent, e.g., a medicament for treatment of a disease, or a probe for specifically detecting a gene mutation of the invention. In certain embodiments, the manufacture is promoted, distributed, or sold as a unit for performing the methods of the present invention.

The term "mutation," as used herein, means or may refer to one or more changes to the sequence of a DNA sequence or a protein amino acid sequence relative to a reference sequence, usually a wild-type sequence. A mutation in a DNA sequence may or may not result in a corresponding change to the amino acid sequence of the encoded protein. A mutation may be a point mutation, i.e. an exchange of a single nucleotide and/or amino acid for another. Point mutations that occur within the protein-coding region of a gene's DNA sequence may be classified as a silent mutation (coding for the same amino acid), a missense mutation (coding for a different amino acid), and a nonsense mutation (coding for a stop which can truncate the protein). A mutation may also be an insertion, i.e. an addition of one or more extra nucleotides and/or amino acids into the sequence. Insertions in the coding region of a gene may alter splicing of the mRNA (splice site mutation), or cause a shift in the reading frame (frameshift), both of which can significantly alter the gene product. A mutation may also be a deletion, i.e. removal of one or more nucleotides and/or amino acids from the sequence. Deletions in the coding region of a gene may alter the splicing and/or reading frame of the gene. A mutation may be spontaneous, induced, naturally occurring, or genetically engineered.

The term "detecting a mutation," as used herein, means that in a subject it may be done by any method useful for analyzing the DNA or amino acid sequence of the subject for the presence or absence of a mutation. Such methods for analyzing a DNA or amino acid sequence are well known to those of skill in the art and any suitable means of detecting a mutation are encompassed by the present invention. Such analysis may be done, for example, by isolating a genomic DNA sample from the subject and using nucleic acid hybridization with a detectable probe to test for the presence and/or absence of a mutation. Alternately, such analysis may be done using an mRNA sample from the subject, and optionally producing cDNA from the sample. Such analysis may also be done, for example, using polymerase chain reaction to amplify a nucleic acid sequence and the amplification product may be sequenced and/or used for hybridization with a probe to detect the mutation. Such analysis may also be done, for example, by isolating a protein sample from the subject and using antibodies to test for the presence and/or absence of a mutation in the protein.

The term "obtained from," as used herein, means that a sample such as, for example, a polynucleotide extract or polypeptide extract is isolated form, or derived form, a particular source of the subject. For example, the extract can be obtained from a tissue or a biological fluid isolated directly from the subject.

The term "treating a disease," as used herein, means taking steps to obtain beneficial or desired results, including clinical results, such as mitigating, alleviating or ameliorating one or more symptoms of a disease; diminishing the extent of disease; delaying or slowing disease progression; ameliorating and palliating or stabilizing a metric (statistic) of disease; causing the subject to experience a reduction, delayed progression, regression or remission of the disorder (CAKUT) and/or its symptoms. "Treatment" refers to the steps taken.

The terms "hybridize" or "hybridization," as used herein, mean a process where two complementary nucleic acid strands anneal to each other under appropriately stringent conditions. Oligonucleotides or probes suitable for hybridizations typically contain 10-100 nucleotides in length (e.g., 18-50, 12-70, 10-30, 10-24, 18-36 nucleotides in length). Nucleic acid hybridization techniques are well known in the art. See, e.g., Sambrook, et al., 1989, Molecular Cloning: A Laboratory Manual, Second Edition, Cold Spring Harbor Press, Plainview, N.Y. Those skilled in the art understand how to estimate and adjust the stringency of hybridization conditions such that sequences having at least a desired level of complementary will stably hybridize, while those having lower complementary will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J.

The term "specific," as used herein, and when used in connection with an oligonucleotide primer, means an oligonucleotide or primer or probe (which can be used interchangeably), under appropriate hybridization or washing conditions, is capable of hybridizing to the target gene mutation of interest and not substantially hybridizing to nucleic acids which are not of interest. Higher levels of sequence identity are preferred and include at least 60%, 65%, 70%, 75%, 80%, 85%, 90%, 95%, 98%, 99%, or 100% sequence identity. In some embodiments, a specific oligonucleotide or primer contains at least 4, 6, 8, 10, 12, 14, 16, 18, 20, 22, 24, 26, 28, 30, 35, 40, 45, 50, 55, 60, 65, 70, or more bases of sequence identity with a portion of the nucleic acid to be hybridized or amplified when the oligonucleotide and the nucleic acid are aligned.

The term "hybridizing specifically with" as used herein, means that there is no significant cross-hybridization with DNAs or RNAs encoding other proteins under usual hybridization conditions, preferably under stringent hybridization conditions. Such a DNA doesn't have to be completely complementary to the target sequence but is generally at least 70%, preferably at least 80%, and more preferably at least 90% (for example, 95% or more) identical to the target at the base sequence level.

The term "complementary nucleotide sequence," as used herein, a sequence of nucleotides in a single-stranded molecule or segment of DNA or RNA that is sufficiently complementary to that on another single oligonucleotide strand to specifically hybridize to it with consequent hydrogen bonding. Where single nucleotide polymorphisms are the target for detection, then the complementarity between the analyte and analyte binding arm on the binary probes should be exact, 100%. If less selectivity is required, then routine experimentation will determine the level of complementarity that provides the desired result.

The terms "primer" and "probe," as used herein, mean the function of the oligonucleotide. A primer is typically extended by polymerase or ligation following hybridization to the target but a probe typically is not. A hybridized oligonucleotide may function as a probe if it is used to capture or detect a target sequence, and the same oligonucleotide may function as a primer when it is employed as a target binding sequence in an amplification primer.

The term "wild-type," as used herein, means the typical sequence or sequences of a gene and/or protein in nature, i.e. the most common sequence or sequences in the natural population.

This may, however, over a period of time be replaced by another form and/or vary between populations within the same species.

The term "genotype," as used herein, means the genetic makeup of a cell, an organism, or an individual (i.e. the specific allele makeup of the individual) usually with reference to a specific character under consideration.

The term "polymorphism," as used herein, means a variation in a gene sequence. Polymorphisms can be referred to, for instance, by the nucleotide position at which the variation exists, by the change in amino acid sequence caused by the nucleotide variation, or by a change in some other characteristic of the nucleic acid molecule or protein that is linked to the variation.

The term "sample," as used herein, means a biological sample obtained from a subject including a lymphoma sample, blood, plasma, serum, cerebrospinal fluid and bone marrow aspirates.

The terms "single nucleotide polymorphism" or "SNP," as used herein, mean a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations). A single nucleotide polymorphism usually arises due to substitution of one nucleotide for another at the polymorphic site. Single nucleotide polymorphisms can also arise from a deletion of a nucleotide or an insertion of a nucleotide relative to a reference allele.

The term "subject," as used herein, means any organism including, without limitation, a mammal such as a mouse, a rat, a dog, a guinea pig, a ferret, a rabbit and a primate. In the preferred embodiment, the subject is a human being.

The term "therapeutically effective amount," as used herein, means an amount of a therapeutic agent that alone, or together with one or more additional therapeutic agents, induces the desired response.

The term "dasatinib," as used herein, and previously known as BMS-354825, means a cancer drug produced by Bristol-Myers Squibb and sold under the trade name SPRYCEL®. Dasatinib is an oral multi-BCR/ABL and SRC family tyrosine kinase inhibitor approved for first line use in patients with chronic myelogenous leukemia (CML) and Philadelphia chromosome-positive acute lymphoblastic leukemia (Ph+ ALL). It is being evaluated for use in numerous other cancers, including advanced prostate cancer.

The term "c-SRC tyrosine kinase," also known as protooncogene c-SRC, as used herein, means a non-receptor tyrosine kinase protein that in humans is encoded by the SRC gene. It includes an SH2 domain, an SH3 domain, and a tyrosine kinase domain. This protein phosphorylates a carboxyl-terminus tyrosine residue on human SRC, which acts as a negative regulatory site. An elevated level of activity of c-SRC tyrosine kinase is suggested to be linked to cancer progression by promoting other signals.

2. Overview

Figure 3A:
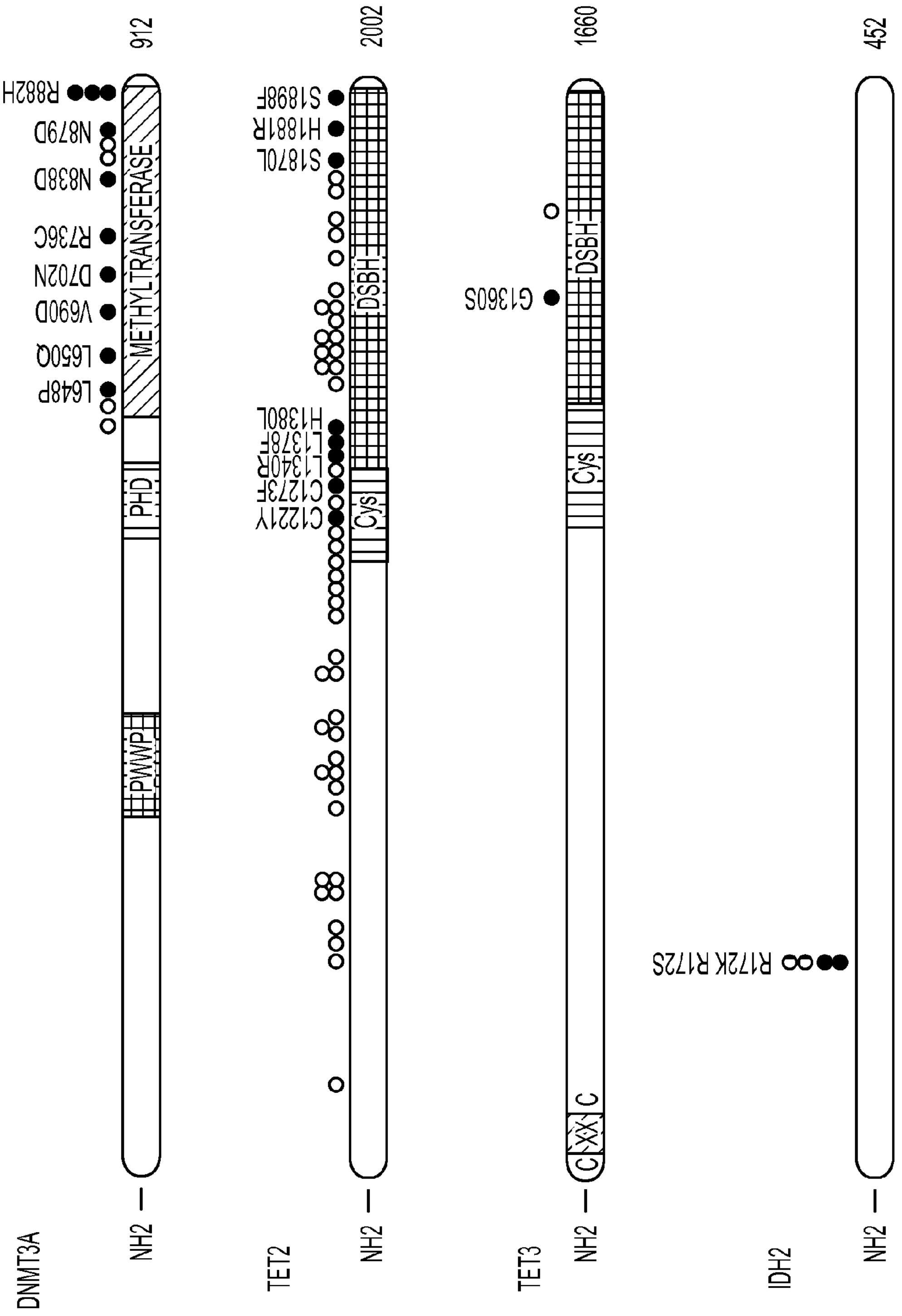
FIG. 3A-3B are schematic representations of DNMT3A, TET2, IDH2, FYN, ATM and TET3 mutations in PTCLs according to an embodiment.
Figure 3B:
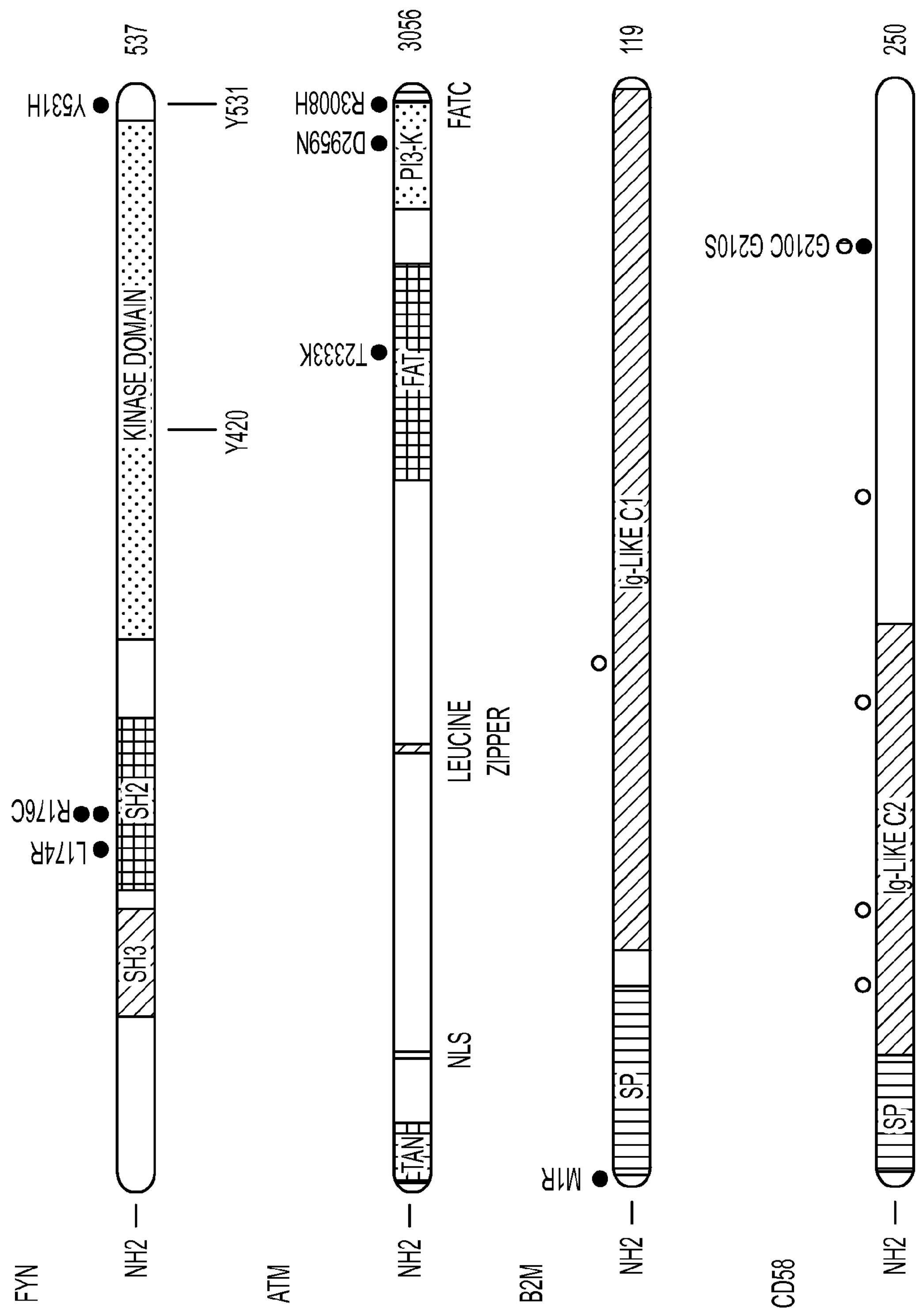

Given these correlations of mutations with occurrence of PTCL, in various embodiments, a subject who is being screened or diagnosed with PTCL, is tested for the occurrence of one or more of these mutations as shown in FIG. 3A-FIG. 3B and in Table 5. For example, a biological sample is drawn from a subject and tested for one or more of these mutations, e.g., using one more kits comprising a microarray or oliogonucleotide furnished for the purpose. If such a mutation is found, then, the subject is diagnosed with having an increased risk of developing PTCL or a diagnosis of PTCL is confirmed. When the diagnosis is made or confirmed based on the presence of one or more of these mutations, treatment is initiated or changed. The treatment is initiated or changed to include administration of a therapeutically effective amount of a SRC kinase inhibitor if the mutation is a FYN mutation as described herein.

3. Summary of Experimental Results and Embodiments

In summary, it has been discovered that PTCLs are associated with mutations in the RHOA, FYN, TET2, TET3, DNMT3A, IDH2, ATM, B2M and CD58 genes. The following is a summary of results of experiments described in the Examples of this application.

- Whole exome sequencing of 12 tumor-normal DNA pairs, RNAseq analysis and targeted deep sequencing were combined to identify new genetic alterations in PTCL transformation.
- Recurrent epigenetic factor mutations in TET2, DNMT3A, and IDH2 as well as a new highly prevalent RHOA p.Gly17Val (NM_001664) mutation present in 22/35 (67%) of AITLs and 8/44 (18%) of not otherwise specified PTCL (PTCL-NOS) samples were identified;
- Mechanistically, the RHOA Gly17Val protein interferes with RHOA signaling in biochemical and cellular assays, an effect potentially mediated by the sequestration of activated Guanine Exchange Factor (GEF) proteins;
- Novel recurrent genetic defects including mutations in FYN, ATM, B2M and CD58 implicating SRC signaling, impaired DNA damage response and escape from immune surveillance mechanisms in the pathogenesis of PTCL are described; and
- Expression of FYN mutant proteins resulted in deregulated kinase signaling which was effectively blocked by dasatinib, a multikinase inhibitor of ABL1 and SRC kinases; and

4. Embodiments

In various embodiments, the identification of these mutations may be used as a screening and diagnostic tool in subjects suspected of having or having PTCL. A subject who is being screened for PTCL or diagnosed with PTCL, is tested for the occurrence of one ore more mutations selected from the group consisting of RHOA p.Gly17Val, RHOA p.Cys16Arg, RHOA p.Thr19Ile, RHOA p.Gly17Glu, RHOA p.Asp120Tyr, FYN p.Leu174Arg, FYN p.Arg176Cys, and FYN p.Tyr531His. If such a mutation is found, then the subject is diagnosed with an increased risk of developing PTCL or having PTCL. When the diagnosis is made or confirmed based on the presence of one or more FYN mutations, treatment with an SRC kinase inhibitor is preferred.

A. RHOA

RHOA belongs to the Rho family of small GTPases, a group of Ras-like proteins responsible for linking a variety of cell-surface receptors to different intracellular signaling proteins[11-13]. As is the case for RAS and most other small GTPases, RHOA cycles between inactive—GDP-bound—and active—GTP-bound—configurations[12,13]. This molecular switch from inactive—GDP-bound—to active—GTP-bound—is strictly controlled by the GTP loading activity of guanosine exchange factors (GEFs). In its active configuration, GTP RHOA interacts with multiple downstream effector proteins that control cell adhesion, polarization, migration and survival[14]. Conversely, GTPase activating proteins (GAPs), responsible for inactivating RHOA signaling, stimulate the intrinsic GTP hydrolytic activity of RHOA turning active GTP RHOA into inactive GDP RHOA. Notably, detailed structure-function analysis has identified specific mutations such as RHOA Q63L, which interfere with the GTPase activity of RHOA resulting in constitutively active RHOA signaling[15-18]. In contrast, other mutants such as RHOA T19N are constitutively bound to GDP and function as dominant negative proteins capable of blocking activation of wild type RHOA[17-19].

B. RHOA Mutations

New mutations in the RHOA gene have been identified as RHOA p.Gly17Val (NM_001664), RHOA p.Cys16Arg, RHOA p.Thr19Ile, and RHOA p.Gly17Glu. The RHOA p.Gly17Val mutation is known to disrupt RHOA activation according to certain embodiments. The RHOA mutations can be found in FIG. 1A and Table 5. RHOA p.Gly17Val was identified in 67% of confirmed AITL samples and in 18% of PTCL-NOS tumors. Therefore certain embodiments of the invention are directed to determining if a subject who does not have lymphoma is at an increased risk of developing PTCL by determining if the nucleic acid in a biological sample from a subject has the RHOA p.Gly17Val, RHOA p.Cys16Arg, RHOA p.Thr19Ile, or RHOA p.Gly17Glu mutation, and determining that the subject has an increased risk of developing PTCL if the RHOA p.Gly17Val, RHOA p.Cys16Arg, RHOA p.Thr19Ile, or RHOA p.Gly17Glu mutation is detected. Biological samples for obtaining DNA include but are not limited to the lymphoma tumor, bone marrow, serum, blood, cerebrospinal fluid and plasma.

The RHOA gene provides one of skill in the art a diagnostic use. Therefore, certain embodiments of the invention are directed to determining if a nucleic acid sample from a subject known to have lymphoma includes the RHOA p.Gly17Val, RHOA p.Cys16Arg, RHOA p.Thr19Ile, or RHOA p.Gly17Glu mutation, and if the mutation is detected, then determining that the subject has PTCL. Moreover, the PTCL thus diagnosed has a 70% chance of being AITL if the RHOA p.Gly17Val mutation is detected. In addition, the presence of the RHOA p.Gly17Val mutation may be used together with other diagnostic markers to make the specific diagnosis of AITL.

C. FYN Mutations

Other mutations correlating with PTCL have been identified as FYN mutations. Fyn is a protein, present in the signaling pathway of integrins, which activates ras. Fyn is a tyrosine-specific phospho-transferase that is a member of the Src family of tyrosine protein kinases. Fyn is primarily localized to the cytoplasmic leaflet of the plasma membrane, where it phosphorylates tyrosine residues on key targets involved in a variety of different signaling pathways. Tyrosine phosphorylation of target proteins by Fyn serves to either regulate target protein activity, and/or to generate a binding site on the target protein that recruits other signaling molecules. Novel recurrent activating mutations in the FYN tyrosine kinase gene were discovered that involve the SH2 domain and a C-terminus phosphosite (P-Y531 or p.Tyr531His) responsible for FYN inactivation by the C-terminal SRC kinase (CSK). Two additional mutations in the FYN kinase gene (in addition to the FYN Y531H or p.Tyr531His allele originally identified in a PTCL-NOS) were identified using exome sequencing. The two new mutations in the FYN gene are FYN R176C or p.Arg176Cys and FYN L174R or p.Leu174Arg. The FYN mutations can be found in FIG. 3B and Table 5. Certain embodiments of the invention are directed to determining if a nucleic acid sample from a subject that does not have lymphoma has either the FYN p.Leu174Arg, FYN p.Arg176Cys or FYN p.Tyr531His mutation and if it does, then determining that the subject has an increased risk of developing PCTL. These genes also have diagnostic use. Certain other embodiments of the invention are directed to determining if a nucleic acid sample from a subject known to have lymphoma has the FYN p.Leu174Arg, FYN p.Arg176Cys or FYN p.Tyr531His, and if the mutation is detected, then determining that the subject has PCTL.

D. SRC Kinase Inhibitors

It was further discovered that dasatinib, a multikinase inhibitor which blocks ABL1 and SRC kinases[(28)], induced dose dependent inhibition of FYN phosphorylation. Therefore, another embodiment is directed to the use of SRC kinase inhibitors, including dasatinib, to prophylactically administer or treat PCTL. Other SRC kinase inhibitors include Bosutinib (SKI-606); Saracatinib (AZD0530); KX2-391; XL-228; JNJ-26483327 as this subtype of lymphoma will respond to the SRCkinase inhibitors. Dasatinib is currently sold as SPRYCEL®, a tablet for oral use for treating certain cancers. It is available as 20-mg, 50-mg, 70-mg, 80-mg, 100-mg, and 140-mg dosages. The recommended starting dosage of SPRYCEL® (dasatinib) for leukemia is 100 mg administered orally once daily. The recommended starting dosage of SPRYCEL® (dasatinib) for certain cancers including accelerated phase CML, myeloid or lymphoid blast phase CML, or Ph+ ALL is 140 mg administered orally once daily, or 180 mg once daily. Dose increase or reduction of 20 mg increments per dose is recommended based on individual safety and tolerability. Routine experimentation will determine the effective dose and route of administration for the individual subject having PTCL using routine criteria known in the art.

Other SRC kinase inhibitors include: XL-228; JNJ-26483327; A 419259 trihydrochloride, inhibitor of SRC family kinases; AZM 475271, SRC tyrosine kinase inhibitor; Bosutinib, Dual SRC-Abl inhibitor; Damnacanthal, Potent, selective inhibitor of p56lck; Herbimycin A, SRC family kinase inhibitor; Lavendustin A, p60c-SRC inhibitor; MNS, Selective inhibitor of SRC; 1-Naphthyl PP1, SRC family kinase inhibitor; PD 166285 dihydrochloride, Potent SRC inhibitor; PP 1, Potent, selective SRC inhibitor; PP 2, Potent, selective SRC inhibitor; SRC I1, Dual site SRC kinase inhibitor; KX2-391 (KX01), a highly selective non ATP-competitive SRC inhibitor; and NVP-BHG712, a specific inhibitor of c-Raf, c-SRC.

E. ATM Mutations

In certain embodiments, genetic defects in ATM have been identified. The ATM gene provides instructions for making a protein that is located primarily in the nucleus of cells, where it helps control the rate at which cells grow and divide. This protein also plays an important role in the normal development and activity of several body systems, including the nervous system and the immune system. Additionally, the ATM protein assists cells in recognizing damaged or broken DNA strands. DNA can be damaged by agents such as toxic chemicals or radiation. Breaks in DNA strands also occur naturally when chromosomes exchange genetic material during cell division. The ATM protein coordinates DNA repair by activating enzymes that fix the broken strands. Efficient repair of damaged DNA strands helps maintain the stability of the cell's genetic information. Because of its central role in cell division and DNA repair, the ATM protein is of great interest in cancer research. Research suggests that people who carry one mutated copy of the ATM gene in each cell may have an increased risk of developing several other types of cancer. In particular, some studies have shown that cancers of the stomach, bladder, pancreas, lung, and ovaries occur more frequently in ATM mutation carriers than in people who do not carry these mutations. In certain embodiments, genetic defects in ATM (e.g., T2333K, D2959N, and R3008H) can be found in FIG. 3B and are implicated in impaired DNA damage response.

F. B2M Mutations

In other embodiments, genetic defects in B2M have been identified. $\beta_2$ microglobulin also known as B2M is a component of MHC class I molecules, which are present on all nucleated cells (excludes red blood cells). In humans, the B2M protein is encoded by the B2M gene. Mice models deficient for the B2M gene have been engineered and are known in the art. These mice demonstrate that B2M is necessary for cell surface expression of MHC class I and stability of the peptide binding groove. In fact, in the absence of B2M, very limited amounts of MHC class I (classical and non-classical) molecules can be detected on the surface. In the absence of MHC class I, CD8 T cells cannot develop. (CD8 T cells are a subset of T cells involved in the development of acquired immunity.) In certain embodiments, genetic defects in B2M (e.g., M1R) can be found in FIG. 3B and are implicated in escape from immune surveillance mechanisms.

G. CD58 Mutations

CD58, or lymphocyte function-associated antigen 3 (LFA-3), is a cell adhesion molecule expressed on Antigen Presenting Cells (APC), particularly macrophages. In certain embodiments, mutations in CD58 have been identified. CD58 binds to CD2 (LFA-2) on T cells and is important in strengthening the adhesion between the T cells and Professional Antigen Presenting Cells. This adhesion occurs as part of the transitory initial encounters between T cells and Antigen Presenting Cells before T cell activation, when T cells are roaming the lymph nodes looking at the surface of APCs for peptide: MHC complexes the T-cell receptors are reactive to. In certain embodiments, genetic defects in CD58 (e.g., G210C, G210S) can be found in FIG. 3B and are implicated escape from immune surveillance mechanisms.

H. DNMT3A Mutations

In yet other embodiments, mutations in DNA (cytosine-5)-methyltransferase 3A, or DNMT3A are highly recurrent DNMT3A is an enzyme that catalyzes the transfer of methyl groups to specific CpG structures in DNA, a process called DNA methylation. The enzyme is encoded in humans by the DNMT3A gene. In certain embodiments, genetic defects in DNMT3A (e.g., AG642, L648P, L650Q, V690D, D702N, R736C, N838D, N879D, P871, R736C, R882C, V622+, V690D, W860, and R882H) can be found in FIG. 3A and Table 5 and are implicated in epigenetic deregulation of gene expression.

I. TET2 and TET3 Mutations

It has also been discovered that the Tet methylcytosine dioxygenase 2 (TET2) mutation is a highly recurrent epigenetic factor. TET2 is a human gene that encodes a protein that catalyzes the conversion of the modified DNA base methylcytosine to 5-hydroxymethylcytosine. Mutations in this gene were first identified in myeloid neoplasms with deletion or uniparental disomy at 4q24. TET2 may also be a candidate for active DNA demethylation, the catalytic removal of the methyl group added to the fifth carbon on the cytosine base. TET2 resides at chromosome 4q24, in a region showing recurrent microdeletions and copy-neutral loss of heterozygosity (CN-LOH) in patients with diverse myeloid malignancies. Somatic TET2 mutations are frequently observed in myelodysplastic syndromes (MDS), myeloproliferative neoplasms (MPN), MDS/MPN overlap syndromes including chronic myelomonocytic leukaemia (CMML), acute myeloid leukaemias (AML) and secondary AML (sAML). TET2 mutations have prognostic value in cytogenetically normal acute myeloid leukemia (CN-AML). “Nonsense” and “frameshift” mutations in this gene are associated with poor outcome on standard therapies in this otherwise favorable-risk patient subset. In certain embodiments, genetic defects in TET2 (e.g. C1221Y, C1273F, L1340R, L1378F, H1380L, S1870L, H1881R, and S1898F,) can be found in FIG. 3A and Table 5 and are highly recurrent epigenetic factor mutations.

In other embodiments, TET3 (tet methylcytosine dioxygenase 3) is a protein-coding gene. Diseases associated with TET3 include acute myeloid leukemia, and myeloid leukemia. GO annotations related to this gene include methylcytosine dioxygenase activity and oxidoreductase activity, acting on single donors with incorporation of molecular oxygen, incorporation of two atoms of oxygen. An important paralog of this gene is TET2. In certain embodiments, genetic defects in TET3 (e.g. G1360S, and D1469) can be found in FIG. 3A and Table 5 and are highly recurrent epigenetic factor mutations.

J. IDH2 Mutations

In certain embodiments, mutations in IDH2 are identified and are highly recurrent. IDH2 (isocitrate dehydrogenase 2 (NADP+), mitochondrial) is a protein-coding gene. Diseases associated with IDH2 include d-2-hydroxyglutaric aciduria 2, and d-2-hydrosyglutaric aciduria 2, and among its related super-pathways are Citric acid cycle (TCA cycle) and Metabolic pathways. GO annotations related to this gene include isocitrate dehydrogenase (NADP+) activity and magnesium ion binding. An important paralog of this gene is IDH1. Neomorphic mutations in IDH1 and IDH2 resulting in the synthesis of 2-hydroxyglutarate (2HG) have been described in myeloid tumors (acute myeloid leukemia, myelodisplasia), glioblastoma and chondrosarcomas. 2HG is an inhibitor of enzymes dependent on alpha ketoglutarate including the TET2 family of proteins involved in epigenetic regulation of gene expression. In certain embodiments, genetic defects in IDH2 (e.g. R172K and R172S) can be found in FIG. 3A and Table 5 and are highly recurrent epigenetic factor mutations.

Other embodiments are directed to microarrays on which are immobilized oligonucleotides that selectively hybridize with RHOA p.Cys16Arg, RHOA p.Thr19Ile, and RHOA p.Gly17Glu, FYN p.Leu174Arg, FYN p.Arg176Cys, and FYN p.Tyr531His. Kits for detecting these mutations comprising microarrays or oligonucleotides are also provided.

K. Methods for Detecting Nucleic Acid Mutations

Methods are provided in certain embodiments for detecting the RHOA, FYN, DNMT3A, TET2, TET3, IDH2, ATM, B2M, and CD58 mutations. Methods of isolating and analyzing nucleic acid molecules from a biological sample are routine, for example using PCR to amplify the molecules from the sample, or by using a commercially available kit to isolate DNA. Nucleic acid molecules isolated from a biological sample can be amplified using routine methods to form nucleic acid amplification products.

1. Amplification of Nucleic Acid Molecules

Nucleic acid molecules can be prepared for analysis using any technique known to those skilled in the art. Generally, such techniques result in the production of a nucleic acid molecule sufficiently pure to determine the presence or absence of one or more variations at one or more locations in the nucleic acid molecule. Such techniques are described for example, in Sambrook, et al., Molecular Cloning: A Laboratory Manual (Cold Spring Harbor Laboratory, New York) (1989), and Ausubel, et al., Current Protocols in Molecular Biology (John Wiley and Sons, New York) (1997), incorporated herein by reference.

Optionally, the nucleic acid samples obtained from the subject are amplified prior to detection. Target nucleic acids are amplified to obtain amplification products, including sequences from a tag SNP, can be amplified from the sample prior to detection. Typically, DNA sequences are amplified by PCR, although in some instances RNA sequences can be amplified or converted into cDNA, such as by using RT PCR. PCR is one of the most widely used enrichment strategies for over 20 years. PCR is technology to amplify specific DNA sequences. It uses a single stranded piece of DNA as a start for DNA amplification. Uniplex PCR uses only one starting point (primer) for amplification and multiplex PCR uses multiple primers. This way multiple genes can be targeted simultaneously. This approach is known to be useful in classical Sanger sequencing because a uniplex PCR used to generate a single DNA sequence is comparable in read length to a typical amplicon. Multiplex PCR reactions which require several primers are challenging although strategies to get around this have been developed. A limitation to this method is the size of the genomic target due to workload and quantity of DNA required. The PCR based approach is highly effective, yet it is not feasible to target genomic regions that are several megabases in size due to quantity of DNA required and cost.

Methods for labeling nucleic acid molecules so they can be detected are well known. Examples of such labels include non-radiolabels and radiolabels. Non-radiolabels include, but are not limited to an enzyme, chemiluminescent compound, fluorescent compound (such as FITC, Cy3, and Cy5), metal complex, hapten, enzyme, colorimetric agent, a dye, or combinations thereof. Radiolabels include, but are not limited to, $^{125}I$, $^{32}P$ and $^{35}S$. For example, radioactive and fluorescent labeling methods, as well as other methods known in the art, are suitable for use with the present disclosure. In one example, primers used to amplify the subject's nucleic acids are labeled (such as with biotin, a radiolabel, or a fluorophore). In another example, amplified target nucleic acid samples are end-labeled to form labeled amplified material. For example, amplified nucleic acid molecules can be labeled by including labeled nucleotides in the amplification reactions.

Nucleic acid molecules corresponding to one or more SNPs can also be detected by hybridization procedures using a labeled nucleic acid probe, such as a probe that detects only one alternative allele at a marker locus. Most commonly, the target nucleic acid (or amplified target nucleic acid) is separated based on size or charge and transferred to a solid support. The solid support (such as membrane made of nylon or nitrocellulose) is contacted with a labeled nucleic acid probe, which hybridizes to it complementary target under suitable hybridization conditions to form a hybridization complex.

Detection techniques for evaluating nucleic acids for the presence of a SNP involve procedures well known in the field of molecular genetics. Further, many of the methods involve amplification of nucleic acids. Ample guidance for performing is provided in the art. Exemplary references include manuals such as PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Current Protocols in Molecular Biology, Ausubel, 1994-1999, including supplemental updates through April 2004; Sambrook & Russell, Molecular Cloning, A Laboratory Manual (3rd Ed, 2001).

Although the methods typically employ PCR steps, other amplification or non-amplification-based protocols may also be used. Suitable amplification methods include ligase chain reaction (see, e.g., Wu & Wallace, Genomics 4:560-569, 1988); strand displacement assay (see, e.g., Walker et al., Proc. Natl. Acad. Sci. USA 89:392-396, 1992; U.S. Pat. No. 5,455,166); and several transcription-based amplification systems, including the methods described in U.S. Pat. Nos. 5,437,990; 5,409,818; and 5,399,491; the transcription amplification system (TAS) (Kwoh et al., Proc. Natl. Acad. Sci. USA 86:1173-1177, 1989); and self-sustained sequence replication (3SR) (Guatelli et al., Proc. Natl. Acad. Sci. USA 87:1874-1878, 1990; WO 92/08800). Alternatively, methods that amplify the probe to detectable levels can be used, such as Qβ-replicase amplification (Kramer & Lizardi, Nature 339:401-402, 1989; Lomeli et al., Clin. Chem. 35:1826-1831, 1989). A review of known amplification methods is provided, for example, by Abramson and Myers in *Current Opinion in Biotechnology* 4:41-47, 1993. The amount and/or presence of an allele of a SNP of the invention in a sample from an individual can be determined using many detection methods that are well known in the art. A number of SNP assay formats entail one of several general protocols: hybridization using allele-specific oligonucleotides, primer extension, allele-specific ligation, sequencing, or electrophoretic separation techniques, e.g., singled-stranded conformational polymorphism (SSCP) and heteroduplex analysis. Exemplary assays include 5' nuclease assays, template-directed dye-terminator incorporation, molecular beacon allele-specific oligonucleotide assays, single-base extension assays, and SNP scoring by real-time pyrophosphate sequences. Analysis of amplified sequences can be performed using various technologies such as microchips, fluorescence polarization assays, and matrix-assisted laser desorption ionization (MALDI) mass spectrometry. Two methods that can also be used are assays based on invasive cleavage with Flap nucleases and methodologies employing padlock probes.

Determining the presence or absence of a particular SNP allele is generally performed by analyzing a nucleic acid sample that is obtained from a biological sample from the individual to be analyzed. While the amount and/or presence of a SNP allele can be directly measured using RNA from the sample, often times the RNA in a sample will be reverse transcribed, optionally amplified, and then the SNP allele will be detected in the resulting cDNA.

Frequently used methodologies for analysis of nucleic acid samples to measure the amount and/or presence of an allele of a SNP are briefly described. However, any method known in the art can be used in the invention to measure the amount and/or presence of single nucleotide polymorphisms.

Hybridization conditions for a given combination of array and target material can be optimized using methods known to one of skill in the art (see U.S. Pat. No. 5,981,185). Once the target nucleic acid molecules have been hybridized with the labeled probes, the presence of the hybridization complex can be analyzed, for example by detecting the complexes. Methods for detecting hybridized nucleic acid complexes are well known in the art.

2. Allele Specific PCR

Allele-specific PCR differentiates between target regions differing in the presence of absence of a variation or polymorphism. PCR amplification primers are chosen based upon their complementarity to the target sequence, such as nucleic acid sequence in a haplotype block including a tag SNP, a specified region of an allele including a tag SNP, or to the tag SNP itself. The primers bind only to certain alleles of the target sequence. This method is described by Gibbs, Nucleic Acid Res. 17:12427 2448, 1989, herein incorporated by reference.

3. Allele Specific Oligonucleotide Screening Methods

Further screening methods employ the allele-specific oligonucleotide (ASO) screening methods (e.g. see Saiki et al., Nature 324:163-166, 1986). Oligonucleotides with one or more base pair mismatches are generated for any particular allele or haplotype block. ASO screening methods detect mismatches between one allele (or haplotype block) in the target genomic or PCR amplified DNA and the other allele (or haplotype block), showing decreased binding of the oligonucleotide relative to the second allele (i.e. the other allele) oligonucleotide. Oligonucleotide probes can be designed that under low stringency will bind to both polymorphic forms of the allele, but which at high stringency, only bind to the allele to which they correspond. Alternatively, stringency conditions can be devised in which an essentially binary response is obtained, i.e., an ASO corresponding to a variant form of the target gene will hybridize to that allele (haplotype block), and not to the reference allele (haplotype block).

4. Ligase Mediated Allele Detection Method

Ligase can also be used to detect point mutations, such as the tag SNPs disclosed herein, in a ligation amplification reaction (e.g. as described in Wu et al., Genomics 4:560-569, 1989). The ligation amplification reaction (LAR) utilizes amplification of specific DNA sequence using sequential rounds of template dependent ligation (e.g. as described in Wu, supra, and Barany, Proc. Nat. Acad. Sci. 88:189-193, 1990).

5. Denaturing Gradient Gel Electrophoresis

Amplification products generated using the polymerase chain reaction can be analyzed by the use of denaturing gradient gel electrophoresis. Different alleles (haplotype blocks) can be identified based on the different sequence-dependent melting properties and electrophoretic migration of DNA in solution. DNA molecules melt in segments, termed melting domains, under conditions of increased temperature or denaturation. Each melting domain melts cooperatively at a distinct, base-specific melting temperature ($T_M$). Melting domains are at least 20 base pairs in length, and can be up to several hundred base pairs in length.

6. Non-Gel Systems

Other possible techniques include non-gel systems such as TaqMan™ (Perkin Elmer). In this system oligonucleotide PCR primers are designed that flank the mutation in question and allow PCR amplification of the region. A third oligonucleotide probe is then designed to hybridize to the region containing the base subject to change between different alleles of the gene. This probe is labeled with fluorescent dyes at both the 5' and 3' ends. These dyes are chosen such that while in this proximity to each other the fluorescence of one of them is quenched by the other and cannot be detected. Extension by Taq DNA polymerase from the PCR primer positioned 5' on the template relative to the probe leads to the cleavage of the dye attached to the 5' end of the annealed probe through the 5' nuclease activity of the Taq DNA polymerase. This removes the quenching effect allowing detection of the fluorescence from the dye at the 3' end of the probe. The discrimination between different DNA sequences arises through the fact that if the hybridization of the probe to the template molecule is not complete (there is a mismatch of some form) the cleavage of the dye does not take place. Thus only if the nucleotide sequence of the oligonucleotide probe is completely complimentary to the template molecule to which it is bound will quenching be removed. A reaction mix can contain two different probe sequences each designed against different alleles that might be present thus allowing the detection of both alleles in one reaction.

7. Non-PCR Based Allele Detection

The identification of a DNA sequence can be made without an amplification step, based on polymorphisms including restriction fragment length polymorphisms in a subject and a control, such as a family member. Hybridization probes are generally oligonucleotides which bind through complementary base pairing to all or part of a target nucleic acid. Probes typically bind target sequences lacking complete complementarity with the probe sequence depending on the stringency of the hybridization conditions. The probes can be labeled directly or indirectly, such that by assaying for the presence or absence of the probe, one can detect the presence or absence of the target sequence. Direct labeling methods include radioisotope labeling, such as with $^{32}P$ or $^{35}S$. Indirect labeling methods include fluorescent tags, biotin complexes which can be bound to avidin or streptavidin, or peptide or protein tags. Visual detection methods include photoluminescents, Texas red, rhodamine and its derivatives, red leuco dye and 3,3',5,5'-tetramethylbenzidine (TMB), fluorescein, and its derivatives, dansyl, umbelliferone and the like or with horseradish peroxidase, alkaline phosphatase and the like.

8. Whole Exome Sequencing

Whole exome sequencing (also known as targeted exome capture) is an efficient strategy to selectively sequence the coding regions of the genome as a cheaper but still effective alternative to whole genome sequencing. Exons are short, functionally important sequences of DNA which, together, represent only slightly more than the portion of the genome that is actually translated into protein. Exons are flanked by untranslated regions (UTR) that are usually not included in exome studies. In the human genome there are about 180,000 exons. These constitute about 1% of the human genome or about 30 megabases. The robust approach to sequencing the complete coding region (exome) has the potential to be clinically relevant in genetic diagnosis due to current understanding of functional consequences in sequence variation. Although exome sequencing is an expensive method relative to other technologies (e.g., hybridization-based technologies) currently available, it is an efficient strategy to identify the genetic bases that underlie rare mendelian disorders. This approach has become increasingly practical with the falling cost and increased throughput of whole genome sequencing. Even by only sequencing the exomes of individuals, a large quantity of data and sequence information is generated which requires a significant amount of data analysis.

9. Deep Sequencing and RNAseq Analysis

In certain embodiments, whole exome sequencing was combined with RNAseq analysis and targeted deep sequencing to identify genetic alterations in PCTCL transformation. Depth (coverage) in DNA sequencing refers to the number of times a nucleotide is read during the sequencing process. Deep sequencing indicates that the total number of reads is many times larger than the length of the sequence under study. Coverage is the average number of reads representing a given nucleotide in the reconstructed sequence. Depth can be calculated from the length of the original genome (G), the number of reads (N), and the average read length (L) as $N \times L/G$. For example, a hypothetical genome with 2,000 base pairs reconstructed from 8 reads with an average length of 500 nucleotides will have 2× redundancy. This parameter also enables one to estimate other quantities, such as the percentage of the genome covered by reads (sometimes also called coverage). A high coverage in shotgun sequencing is desired because it can overcome errors in base calling and assembly. The subject of DNA sequencing theory addresses the relationships of such quantities. Sometimes a distinction is made between sequence coverage and physical coverage. Sequence coverage is the average number of times a base is read (as described above). Physical coverage is the average number of times a base is read or spanned by mate paired reads. The term "deep" has been used for a wide range of depths (>7×), and the newer term "ultra-deep" has appeared in the scientific literature to refer to even higher coverage (>100×). Even though the sequencing accuracy for each individual nucleotide is very high, the very large number of nucleotides in the genome means that if an individual genome is only sequenced once, there will be a significant number of sequencing errors. Furthermore rare single-nucleotide polymorphisms (SNPs) are common. Hence to distinguish between sequencing errors and true SNPs, it is necessary to increase the sequencing accuracy even further by sequencing individual genomes a large number of times.

Deep sequencing of transcriptome, also known as RNA-Seq, provides both the sequence and frequency of RNA molecules that are present at any particular time in a specific cell type, tissue or organ. Counting the number of mRNAs that are encoded by individual genes provides an indicator of protein-coding potential, a major contributor to phenotype.

L. Nucleic Acid Arrays

Certain embodiments are directed to a microarrays for detecting one or more gene mutations. A microarray is a multiplex lab-on-a-chip. It is a 2D array on a solid substrate (usually a glass slide or silicon thin-film cell) that assays large amounts of biological material using high-throughput screening miniaturized, multiplexed and parallel processing and detection methods. Microarrays are known in the art and available commercially from companies such as Affymetrix, Agilent, Applied Microarrays, Arrayit, Illumina, and others. The array contains probes complementary to at least one single nucleotide polymorphism identified herein, preferably probes are included for hybridization to the target mutations.

It will be readily apparent to one skilled in the art that the exact formulation of probes on an array is not critical as long as the user is able to select probes for inclusion on the array that fulfill the function of hybridizing to the targeted SNPs. The array can be modified to suit the needs of the user. Thus, analysis of the array can provide the user with information regarding the number and/or presence of protective alleles in a given sample. The hybridization of a probe complementary to an SNP mutation in an array can indicate that the subject from whom the sample was derived is at an elevated risk for developing a lymphoma s is described herein.

A wide variety of array formats can be employed in accordance with the present disclosure. One example includes a linear array of oligonucleotide bands, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (see U.S. Pat. No. 5,981,185). In one example, the array is formed on a polymer medium, which is a thread, membrane or film. An example of an organic polymer medium is a polypropylene sheet having a thickness on the order of about 1 mm (0.001 inch) to about 20 mm although the thickness of the film is not critical and can be varied over a fairly broad range. Biaxially oriented polypropylene (BOPP) films are also suitable in this regard; in addition to their durability, BOPP films exhibit a low background fluorescence. In a particular example, the array is a solid phase, Allele-Specific Oligonucleotides (ASO) based nucleic acid array.

The array formats of the present disclosure can be included in a variety of different types of formats. A "format" includes any format to which the solid support can be affixed, such as microtiter plates, test tubes, inorganic sheets, dipsticks, and the like. For example, when the solid support is a polypropylene thread, one or more polypropylene threads can be affixed to a plastic dipstick-type device; polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (such as the dipstick or slide) is stable to any materials into which the device is introduced (such as clinical samples and hybridization solutions).

The arrays of the present disclosure can be prepared by a variety of approaches. In one example, oligonucleotide or protein sequences are synthesized separately and then attached to a solid support (see U.S. Pat. No. 6,013,789). In another example, sequences are synthesized directly onto the support to provide the desired array (see U.S. Pat. No. 5,554,501). Suitable methods for covalently coupling oligonucleotides and proteins to a solid support and for directly synthesizing the oligonucleotides or proteins onto the support are known to those working in the field; a summary of suitable methods can be found in Matson et al., Anal. Biochem. 217:306-10, 1994. In one example, the oligonucleotides are synthesized onto the support using conventional chemical techniques for preparing oligonucleotides on solid supports (see PCT Publication No. WO 85/01051 and PCT Publication No. WO 89/10977, or U.S. Pat. No. 5,554,501).

A suitable array can be produced using automated means to synthesize oligonucleotides in the cells of the array by laying down the precursors for the four bases in a predetermined pattern. Briefly, a multiple-channel automated chemical delivery system is employed to create oligonucleotide probe populations in parallel rows (corresponding in number to the number of channels in the delivery system) across the substrate. Following completion of oligonucleotide synthesis in a first direction, the substrate can then be rotated by 90 degrees to permit synthesis to proceed within a second (2 degrees) set of rows that are now perpendicular to the first set. This process creates a multiple-channel array whose intersection generates a plurality of discrete cells. In particular examples, the oligonucleotide probes on the array include one or more labels, which permit detection of oligonucleotide probe: target sequence hybridization complexes.

M. Kits

Certain embodiments are directed to kits. The disclosed kits may include a microarray or include a binding molecule, such as an oligonucleotide probe that selectively hybridizes the particular known SNP. Alternatively or additionally, the kits can include one or more isolated primers or primer pairs for amplifying the target nucleic acid comprising the SNP.

The kit can further include one or more of a buffer solution, a conjugating solution for developing the signal of interest, or a detection reagent for detecting the signal of interest, each in separate packaging, such as a container. In another example, the kit includes a plurality of size-associated marker target nucleic acid sequences for hybridization with a detection array. The kit can also include instructions in a tangible form, such as written instructions or in a computer-readable format.

Kits comprising a primer or probe that is complementary to and specifically hybridizes to or binds to a target SNP mutation in a nucleic acid sample and enzymes suitable for amplifying nucleic acid are provided in certain embodiments of the invention. The primer or probe may be labeled with a radioisotope, a fluorophore, a chromophore, a dye, an enzyme, or TOF carrier. In these kits, binding may be detected by in situ hybridization, PCR RT-PCR, fluorescence resonance energy transfer, chemiluminescence enzymatic signal amplification, electron dense particles magnetic particles and capacitance coupling. The probe is selected to allow the DNA to be sequenced to identify changes (SNP) as compared to the wild-type sequence. One or more reagents that differentiate a normal RHOA or FYN gene from a mutant gene comprising an SNP are present in the kit. These reagents in certain embodiments may comprise one or more nucleic acid probes, may be in the form of a microarray, are suitable for primer extension and can comprise controls indicative of a healthy individual.

5. Examples

The invention is illustrated herein by the experiments described by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

Example 1

Methods and Materials

Patient Samples.

DNAs from PTCLs were provided by tumor banks at Columbia University Medical Center in New York, USA; Hospital Central de Asturias in Oviedo, Spain, Centro Nacional de Investigaciones Oncologicas in Madrid, Spain; Institut Gustave Roussy, Villejuif, France; Centre Henri Becquerel, Rouen, France, and Hospital Clinic in Barcelona, Spain. Studies presented here were approved and supervised by the Columbia University Institutional Review Board. We collected and analyzed samples under the supervision of Institutional Review Boards of the different participating institutions. Samples were selected for Whole Exome Sequencing based on the availability of sufficient DNA from diagnosis, and normal (blood, buccal swab or non tumor infiltrated biopsy material) matched samples.

Whole Exome Capture and Nextgen Sequence Analysis.

Matched tumor and normal DNA samples from 12 PTCL patients were used (Table 1) for exome capture with the SureSelect 50 Mb All Exon kit (Agilent Technologies) following standard protocols. Paired-end sequencing (2×100 bp) was performed using HiSeq2000 sequencing instruments at Centrillion Biosciences (Palo Alto, Calif.). Illumina HiSeq analysis was performed and produced between 67.5 and 136.8 million paired-end reads per sample (Table 2). Reads to the reference genome hg19 were mapped using the Burrows-Wheeler Aligner (BWA) alignment tool version 0.5.9. Mean depth (defined as mean number of reads covering the captured coding sequence of a haploid reference) and was 45× with 84% of the genome covered more than 10× and 58% covered more than 30×. Sites were identified that differ from reference (called here variants) in each sample independently.

Empirical priors were constructed for the distribution of variant frequencies for each sample. High-credibility intervals (posterior probability$\geq 1\text{-}10^{-5}$) were obtained for the corresponding change in frequency between tumor and normal samples, using the SAVI algorithm (Statistical Algorithm for Variant Identification) developed at Columbia University[32,33]. The number of germline SNPs in the coding region were 18,000 comparable with previous reports[32]. Most of the candidate germline SNPs (16,000, or ~90% of germline variants) were reported in dbSNP database. Candidate somatic variants were identified using the following criteria: variant total depth in tumor and normal larger than 10× and smaller than 300×, variant frequency larger than 15% in tumor and less than 3% in normal, and at least 1% change in frequency from the normal with high posterior probability ($\geq 1\text{-}10^{-5}$). Also to remove systematic errors, all variants that were found present in any of the normal cases were excluded. In addition, to eliminate ambiguous mapping from captured pseudogenes, and regions of low complexity, each variant with a flanking 20-base context sequence around its genomic position was mapped to the hg19 reference using the BLAST algorithm. The list provides only those with unique mappability, i.e. it was required that the 41-base sequence uniquely map to the reference genome, with only one mismatch.

Mutation Validation

Primers were designed flanking exons containing candidate somatic variants using Primer3, and using Whole-Genome-Amplified (WGA) DNA from tumor and matched normal DNAs for PCR amplification. The resulting amplicons were analyzed by direct bidirectional dideoxynucleotide sequencing.

RNA Sequencing, Mapping, and Identification of Variants

After the exome sequence analysis of 12 tumor and normal PTCL samples (Table 1); 35 additional PTCL samples were analyzed by RNA-Seq using paired-end Illumina Hiseq sequencing. (Table 3). On average over 67.6 million reads were obtained, 51.5 million (75.7%) mapped to the human NCBI reference sequence (RefSeq) using BWA alignment algorithms[20]. Reads mapping on the same starting position were discarded. Sites were identified that differed from the reference in each sample and constructed empirical priors for the distribution of variant frequencies for each sample independently. In order to reduce the false positive rate in variants detection and remove mapping artifacts and systematic errors, samples' paired-end reads were mapped to human RefSeq with Bowtie2 alignment algorithm[21], which mapped a total of 1.83 billion reads of reads (76%) properly to the reference. Sites were then identified that differed from the reference in each sample and intersected the set of variants identified with both BWA and Bowtie2 alignments as previously described[22]. In all samples, variants were selected with total depth>10× and frequency>20%, and excluded variants identified in dbSNP135 database, as well as those which did not pass the Multiplicity filter. In addition, variants corresponding to poorly expressed (RPKM<3) genes were removed to reduce the effects of spurious PCR amplification during the library preparation. In order to reduce the presence of germline mutations, variants identified also present in 65 DNA-Seq samples from unaffected individuals were excluded and variants were removed common to those present in 11 RNA-Seq samples from normal B and T cells. In detail, the normal RNA-Seq sample reads were mapped with BWA and Bowtie to human RefSeq and identified the variants, creating an internal normal variant database (INVD) composed by the union of all the variants identified in normal B and T cells. Those variants were filtered occurring in PTCL samples overlapping the INVD. Finally, we limited the list of variants to those identified in genes found somatically mutated in PTCL by exome sequencing.

Targeted Deep Resequencing

Mutational analysis of selected genes of interest was performed by targeted resequencing using microfluidics PCR (Access Array system; Fluidigm) followed by sequencing of the amplicon libraries in a MiSeq instrument (Illumina). Primers listed in Table 10 targeting the regions of interest were designed at Fluidigm to produce amplicons of 200 bp±20 bp. Multiplex PCR amplification of up to 10 amplicons per well was performed in the Fluidigm Access Array chip according to the manufacturer's instructions using 30 ng of DNA per sample. After multiplex PCR amplification the resulting DNA products were barcoded so that all amplicons corresponding to the one sample carry the same index. Indexed libraries were pooled and the resulting library was quantified by quantitative PCR using the Kapa Library Quantification Kit (Kapa Biosystems) in a 7500 PCR instrument (Applied Biosystems). Amplicon libraries were spiked with ~25% PhiX genomic library to increase amplicon diversity and sequenced in a MiSeq instrument to generate 2×251 bp paired reads following an amplicon sequencing protocol for custom primers. Each pair of the paired end reads produced by MiSeq were stitched together using FLASH version 1.2.6 (Fast Length Adjustment of Short reads), given that the amplicon sequences (up to 200 bp) were shorter than the read length (251 bp). This step increases the quality of the reads correcting for mismatches in the overlap by selecting the base with higher quality. Then, 5' and 3' adaptors and PCR primer sequences, were trimmed using cutadapt. Merged and trimmed reads were aligned to the UCSC hg19 reference genome using BWA-MEM as single-end reads. Aligned reads were analyzed for variants using the SAVI (Statistical Algorithm for Variant Identification) algorithm and variants were selected based on coverage depth and frequency. Given the presence of significant normal cells in most PTCL samples, variants around 50% frequency were flagged as candidate private germline SNPs. Candidate variants identified by this first round of amplicon resequencing were independently validated in a second round of targeted deep sequencing. Briefly, the amplicons were selectively amplified covering the positions of candidate mutations in their corresponding positive samples. The PCR products were barcoded, pooled, and the resulting library sequenced in a MiSeq instrument as detailed before.

RNAseq Gene Fusion Analysis

Gene fusion analysis was performed in RNAseq data using ChimeraScan[23] and deFuse[24] algorithms, which identify gene fusion candidates by detecting read pairs discordantly mapping to two different genes. From this analysis the candidate list was reduced by applying homology-based filters and by detecting reads spanning across the junction breakpoint (Split Reads). Candidate fusions were annotated on the base of the breakpoint coordinates, predicted amino acid sequence, open reading frame conservation and UniProt database proteomic information.

Quantitative RHOA G17V Allele Specific qPCR Assay

Analysis and quantitation of RHOA p.Gly17Val was performed using a Mutation Detection Assay Competitive Allele-Specific TaqMan® PCR (Life Technologies) following the manufacturer's instructions with slight modifications. All analyses were conducted on a 7500 real-time PCR system run with 7500 software (v.2.0.6 Applied Biosystems). The assay was run in 96-well plates in a reaction volume of 20 μL, using 50 ng of genomic DNA, 10 μL of Taqman Universal PCR Master Mix 2×, and 2 μL of specific Taqman assay 10× (RHOA wild type or RHOA p.Gly17Val). A thermal profile of 10 min at 95° C. was used for Hot Gold Start activation followed by 40 cycles of amplification (95° C. for 15 s and 55° C. for 60 s). The threshold detection was set at 0.05. Standard curves of CT vs. log template amount for each specific assay were linear over the range of 25 to 250,000 copies of plasmid DNA. A sensitivity of detection was determined for the RHOA p.Gly17Val mutant allele assay of <0.1% by analyzing samples consisting of 10, 25, $10^2$ and $10^3$ copies of RHOA p.Gly17Val mutant allele plasmid DNA spiked into 30 ng (104 copies) of wild type genomic DNA, which corresponds to samples containing 0.1%, 0.25%, 1% or 10% mutation load, respectively. Data analysis was performed with the Mutation Detector™ Software (Life Technologies). Briefly, in mutation analysis calculations, the difference between the CT value of the mutant allele assay and the CT value of the wild type allele assay is calculated for all mutant allele assays run on the sample. This ΔCT value represents the quantity of the specific mutant allele detected within the sample and is used to determine the sample mutation status by comparison to a predetermined detection ΔCT cutoff value.

Structural Depiction and Analysis

Structural coverage of the FYN protein was identified through use of the PSI-Blast and SKAN algorithms. The structures 2DQ7, 2DLY, 3UA7, 2LP5, and 1G83 were structurally aligned into composite structures to assess for conformational flexibilities, and subsequently analyzed through use of the Chimera Suite[(25,26)]. In silico modeling of identified mutations was performed using the I-TASSER software suite and Modeller program; structures were refined and analyzed in Chimera[(25,27)]. Protein stability changes were predicted upon mutation through use of the SDM potential energy statistical algorithm and associated software[(37)]. We created all structural images using UCSF Chimera[(25)].

Plasmids and Vectors pcDNA3 EGFP-RHOA WT (plasmid#12965) containing the full length human RHOA construct fused to EGFP as well as pcDNA3 EGFP-RHOA Thr19Asn dominant negative (plasmid #12967) and pcDNA3 EGFP-RHOA Gln63Leu constitutively active mutants (plasmid #12968) were obtained from Addgene, Inc.[(28)] The RHOA p.Gly17Val allele was generated by site directed mutagenesis on the mammalian expression pcDNA3 EGFP-RHOA WT using the QuickChange II XL Site-Directed Mutagenesis Kit (Stratagene) according to the manufacturer's instructions. PCR products were cloned encompassing wild type RHOA, RHOA p.Gly17Val, RHOA p.Thr19Asn and RHOA p.Gln63Leu with an N-terminal HA tag as BglII-XhoI fragments into the pMSCV vector for retroviral expression. A pRK5 c-FYN plasmid was obtained containing a full length FYN open reading frame[(29)] from Addgene, Inc. (Plasmid #16032) and introduced FYN p.Leu174Arg, FYN p.Arg176Cys and FYN p.Tyr531His FYN p.Thr342Ile and FYN Tyr 531His mutations using the QuickChange II XL Site-Directed Mutagenesis Kit (Stratagene). All constructs were verified by sequencing. Wild type and mutant FYN cDNAs containing an N-terminal HA tag were subcloned into pcDNA3.1 (−) and into the MSCV240-puromycine-IRES-GFP retroviral vector. The CSK-pcDNA3.1 (+) hygro plasmid expressing a full length CSK cDNA open reading frame was a gift from Dr Xin-Yun Huang (Cornell University, New York, N.Y.). FYN SH2 domain complementary DNA constructs were cloned encoding wild type FYN SH2 domain (codons 148-231) with a N-terminal GST tag in the pGEX4-T1 expression vector between the EcoRI and XhoI restriction sites. The FYN SH2 domain mutations Leu174Arg and Arg176Cys were generated by site-directed mutagenesis on the *E. coli* expression pGEX4-T1 FYN SH2 domain vector using the QuikChange II XL Site-Directed Mutagenesis Kit (Stratagene) according to the manufacturer's instructions.

Cell Lines

HEK293T (Thermo Scientific), HeLa (ATCC), and Rat1A cells (a gift from Dr. Ana Lasorella, Columbia University) were cultured in DMEM media supplemented with 10% fetal bovine serum, 100 U $ml^{-1}$ penicillin G and 100 μg $ml^{-1}$ streptomycin at 37° C. in a humidified atmosphere under 5% $CO_2$. Jurkat cells (ATCC) were maintained under similar conditions in RPMI 1640 media supplemented with 10% fetal bovine serum. Cell lines were regularly tested for *mycoplasma* contamination.

Retroviral Production and Infection

The retroviral constructs pMSCV-HA-RHOA, pMSCV-HA-RHOA Gly17Val, pMSCV-HA-RHOA Gln63Leu, pMSCV-HA-RHOA Thr19Asn, pMSCV-FYN, pMSCV-FYN Tyr531His, pMSCV-FYN Arg176Cys, pMSCV-FYN Leu174Arg and the pMSCV control plasmid were transfected with gag-pol and V-SVG expressing vectors into HEK293T cells using JetPEI transfection reagent (Polyplus). Viral supernatants were collected after 48 h and used them for infection of Rat1A and Jurkat cells by spinoculation. After infection, cells were selected for 4 days in media containing 1 ug/ml of puromycin.

Western Blot

Western blot analyses were performed using standard procedures with the following antibodies: RHOA (67B9) rabbit monoclonal antibody against RHOA (#2117, Cell Signaling Technology)(30); FYN rabbit polyclonal antibody (#4023, Cell Signaling Technology)(31); Phospho-SRC Family (Tyr416) polyclonal antibody (#2101, Cell Signaling Technology)(32); CSK (CSK-04) mouse monoclonal antibody (sc-51580, Santa Cruz Biotechnology); GST mouse monoclonal antibody (clone DG122-2A7, Millipore, 1DB-001-0000851588)(33); GAPDH goat polyclonal antibody (sc-20357, Santa Cruz Biotechnology)(34); ARGHEF1 goat polyclonal antibody (sc-8492, Santa Cruz Biotechnology) (35); and a rat monoclonal antibody specific for HA tag (11867423001, Roche Diagnostics, 1DB-001-0000868977).

Protein Expression in *Escherichia coli*, Purification, and Peptide Binding Assays The site-directed mutagenesis method was used to prepare mutant FYN SH2 domain constructs used for the binding assay. Wild type or a mutant FYN SH2 domain were expressed as GST-tagged protein in *E. coli* Rosetta 2(DE3) cells. Expression of the fusion protein was induced by addition of 0.1 mM isopropyl-β-D-thiogalactopyranoside (IPTG) for 3 h at 28° C. Cells were harvested and lysed in lysis buffer (50 mM Tris, pH 7.4, 150 mM NaCl, 5% glycerol, 5 mM β-mercaptoethanol, 0.5% Triton X-100, 0.5 mg/ml lysozyme) supplemented with complete EDTA-free protease inhibitor (Roche). GST-tagged FYN SH2 domain proteins were purified by binding them to immobilized glutathione Sepharose beads (Thermo scientific) and eluting them with 50 mM reduced Glutathione, 50 mM Tris, pH 7.4, 150 mM NaCl, 5% glycerol, 5 mM β-mercaptoethanol. Protein expression and purity were assessed by Coomassie staining. Binding assay was performed with Pull-Down Biotinylated Protein-protein Interaction Kit (Thermo scientific) according to the manufacturer's instructions using an amino acid 527-537 FYN biotinylated peptide (biotin-TEPQYQPGENL)(SEQ ID NO: 1); an amino acid 527-537 pY531 FYN biotinylated peptide (biotin-TEPQpYQPGENL)(SEQ ID NO: 2) and an amino acid 527-537 Y51H FYN biotinylated peptide (biotin-TEPQHQPGENL)(SEQ ID NO: 3) (Anaspec Inc). Synthetic biotinylated peptides were incubated with purified GST-FYN SH2 domain, mutant FYN SH2 domain or GST alone for 1 h at 4° C. Interacting proteins were resolved on 10% SDS-polyacrylamide gel electrophoresis (SDS-PAGE) and transferred to a PVDF membrane and subjected to Western blot with an anti-GST antibody.

Immunofluorescence

F-actin was analyzed in Hela cells transfected with plasmids expressing GFP, GFP-RHOA, GFP-RHOA Gln63Leu, GFP-RHOA Thr19Asn and GFP-RHOA Gly17Val by Phalloidin Texas Red staining (1:100; Life Technologies), followed by DAPI (4',6-Diamidino-2-Phenylindole, Dihydrochloride) staining and confocal microscopy on a Zeiss LSM510-NL) microscope.

RHOA Protein Expression in *Escherichia coli*, Purification, and GEF Exchange Assay Wild type RHOA, RHOA Gly17Ala and RHOA Gly17Val proteins were expressed as GST-tagged proteins in *E. coli* Rosetta 2(DE3) cells. Expression of the fusion proteins was induced in bacteria cells with 0.1 mM isopropyl-β-D-thiogalactopyranoside (IPTG) for 16 h at 18° C. Cells were harvested and lysed in lysis buffer (20 mM Hepes, pH 7.5, 150 mM NaCl, 5 mM MgCl2, 1 mM DTT, 1% Triton X-100, 0.5 mg/ml lysozyme) supplemented with complete EDTA-free protease inhibitor (Roche). GST-tagged RHOA proteins were purified by binding them to immobilized glutathione Sepharose beads (Thermo scientific) and eluting them with 50 mM reduced Glutathione, 50 mM HEPES, pH 7.4, 150 mM NaCl, 5 mM $MgCl_2$, 5% glycerol, 1 mM DTT. Protein expression and purity were assessed by Coomassie staining. Next, the capacity of purified recombinant GST-RHOA, GST-RHOA Gly17Ala and GST-RHOA Gly17Val proteins to incorporate GTP in response to recombinant MCF2L/DBS-His (Cytoskeleton, Inc.) with the RhoGEF exchange assay kit (Cytoskeleton, Inc.) was assessed following the manufacturer's instructions. Briefly, this assay analyzes the uptake of the fluorescent nucleotide analog N-methylanthraniloyl-GTP (mant-GTP) into RHOA by measuring the spectroscopic difference between free and RHOA-bound mant-GTP. As mant-GTP gets bound in the nucleotide binding pocket of RHOA in response to a GEF protein, its fluorescence (ex: 360 nm, em: 440 nm) increases dramatically. Thus, enhancement of mant-GTP fluorescent intensity in the presence of RHOA indicates nucleotide uptake by the GTPase.

RHOA Activation Assay

Jurkat cells expressing wild type HA-RHOA, HA-RHOA Gly17Val, HA-RHOA Thr19Asn and HA-RHOA Gln63Leu and plated them at $10^6$ cells/ml in RPMI 0.5% FBS were used. After 24 hours the cells were spun down and resuspended in serum-free RPMI 1640 media. For serum stimulation cells were treated with media containing 10% FBS for 10 min. Serum starved and serum stimulated cells were washed once with ice cold PBS and lysed in Lysis buffer (50 mM Tris pH 7.5, 10 mM $MgCl_2$, 0.3 M NaCl and 2% IGEPAL). After spinning down to remove debris and membranes lysate protein content was quantified using the Precision Red Advanced Protein Assay (Cytoskeleton, Inc.). Next 100 μg of total cleared protein lysate was incubated with 20 μl Rhotekin-RBD beads (Cystoskeleton, Inc.) for 1 h at 4° C. with rotation. After incubation the Rhotekin-RBD beads were washed with 500 μl wash buffer (25 mM Tris pH 7.5, 30 mM $MgCl_2$ and 40 mM NaCl), and resuspended in 15 μl SDS-PAGE loading buffer. Rhotekin bead samples were loaded into a Bis-Tris gel and proteins were resolved by electrophoresis in MES buffer and transferred to a PVDF membrane. The presence of HA-tagged activated RHOA associated with the Rhotekin-RBD beads was determined by immunoblotting using an HA antibody following standard procedures.

Example 2

Identification of p.Gly17Val Mutation

To investigate the genetics and pathogenic mechanisms of aggressive PTCLs whole exome sequencing of matched tumor and normal DNA from 12 PTCL patients including 6 PTCL-NOS cases, 3 AITLs and 2 nasal type NK-/T-cell lymphomas and 1 enteropathy associated T-cell lymphoma was performed (Tables 1 and 2). This analysis identified a mean of 24 non synonymous somatic mutations per sample (range 4-57) (Table 1). A total of 288 candidate coding somatic mutations in 268 genes were identified. These included five mutant alleles in the TET2 tumor suppressor, three alleles in the SETD2 and DNAH5 and two in the TACC2, RYR3, PTPRD and MGAT4C genes (Tables 3 and 4). In addition a recurrent heterozygous mutation in the RHOA small GTPase gene (p.Gly17Val) present in two independent AITLs and one PTCL NOS sample was identified. (See FIG. 1A, Table 3 and Table 4 where FIG. 1A is a schematic representation of the structure of the RHOA protein. RHOA mutations identified by targeted amplicon resequencing in PTCL samples are shown (n=64). Multiple circles in the same amino acid position account for multiple patients with the same variant).

Figure 5A:
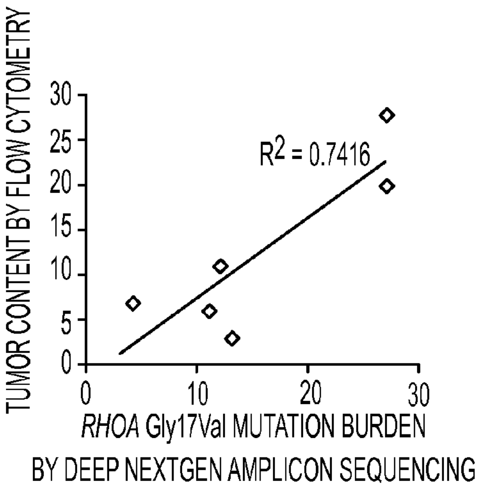
FIG. 5A-5B are graphs that illustrate analysis of tumor content and RHOA p.Gly17Val allele burden in PTCLs according to an embodiment.
Figure 5B:
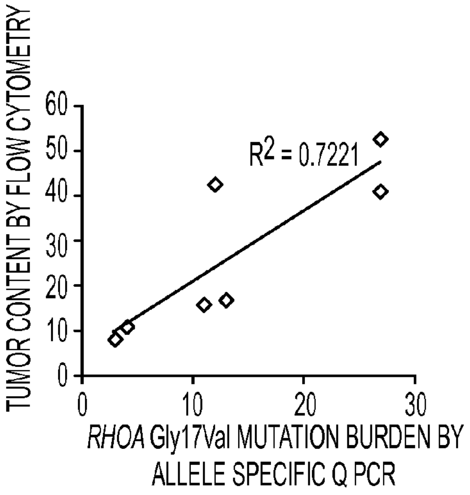

These results were confirmed and extended by deep sequencing analysis of 125 PTCL DNAs, which showed the presence of the recurrent RHOA p.Gly17Val mutation and detection of several additional RHOA mutations (p.Cys16Arg, p.Thr19Ile, p.Gly17Glu and p.Asp120Tyr) present in a single case each. See FIG. 1A and Table 5. Notably the frequency of the allele encoding the Gly17Val alteration correlated with the proportion of tumor cells in PTCL biopsies as evaluated by multicolor flow cytometry, supporting that the variable and frequently low proportion of reads harboring this mutation in many PTCLs may be primarily the result of the low tumor content in these samples. (See FIG. 5A which is a dot plot representation on (100) vertical y-axis the percentage tumor content evaluated by multicolor flow cytometry and on (200) horizontal x-axis the corresponding percentage RHOA Gly17Val mutation content as evaluated by deep amplicon resequencing and FIG. 5B which is a dot plot representation on (100) vertical y-axis of percentage tumor content evaluated by multicolor flow cytometry and on (200) horizontal x-axis corresponding percentage of RHOA p.Gly17Val mutation content as evaluated by allele specific quantitative PCR analysis. Regression lines and coefficient of determinations ($R^2$) are indicated.)

Figure 1B:
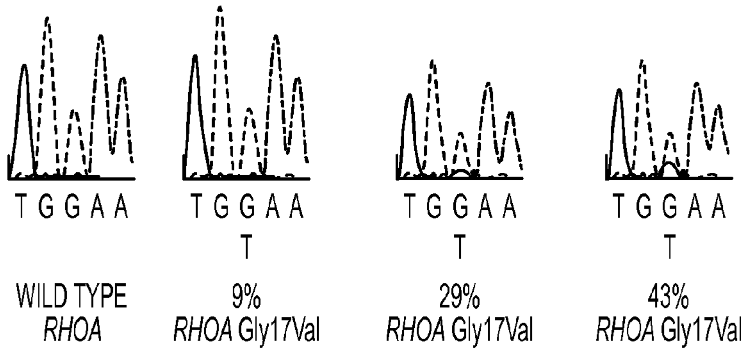
Figure 1C:
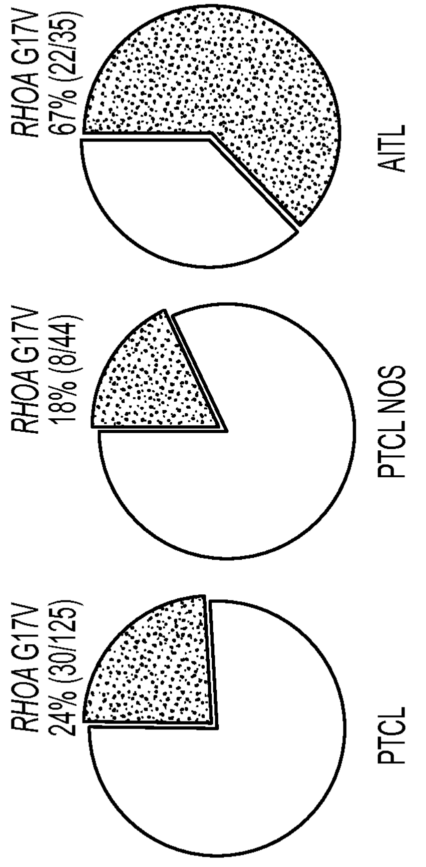
Figure 1D:
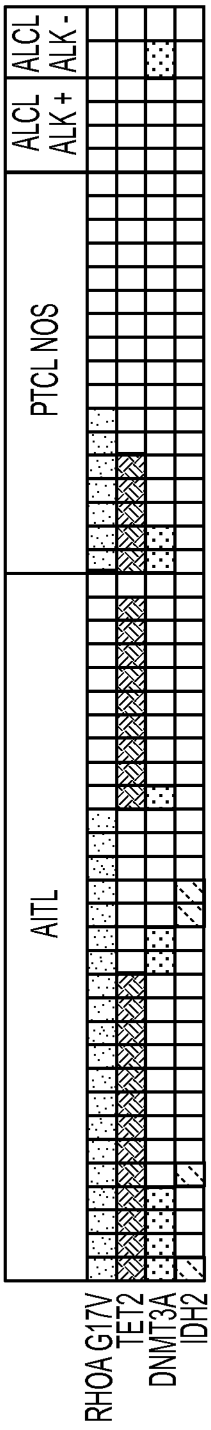

Thus, and to best assess the actual prevalence of RHOA p.Gly17Val alteration in the series this panel was reanalyzed using a highly sensitive (1:1,000) allele specific PCR mutation assay. Using this approach the presence of the allele encoding the pGly17Val mutant RHOA was detected 30 samples including 22/35 (67%) AITLs and 8/44 (18%) PTCL NOS tumors analyzed (AITL vs. all other PTCLs: $P<0.001$; PTCL NOS vs. non-AITL non-PTCL NOS: $P<0.002$; AITL vs. PTCLs NOS: $P<0.001$). (See FIG. 1B which is a schematic representation of DNA sequencing chromatograms of PTCL genomic DNA samples showing representative examples of RHOA p.Gly17Val mutant samples with the mutant allele sequence highlighted in red. The percentage of RHOA p.Gly17Val mutant allele detected by quantitative allele specific PCR is indicated; see FIG. 1C which is a schematic representation of differential distribution of RHOA mutations in all PTCL categories, PTCL NOS and AITLs, FIG. 1D which is a table that illustrates the distribution of RHOA p.Gly17Val, TET2, DNMT3A and IDH2 mutations in major PTCL groups (AITL, n=30; PTCL NOS, n=17; ALCL ALK+, n=4; and ALCL ALKL-, n=2). Colored boxes indicate the presence of mutations in the indicated genes (rows) in each patient sample (columns), and Table 6).

Example 3

An Inhibitory Role for RHOA Gly17Val in RHO Signaling

In order to explore the functional effects of RHOA Gly17Val, the changes in fibroblast cell morphology induced by expression of GFP-RHOA wild type, constitutively active GFP-RHOA Gln63Leu[8-11], dominant negative GFP-RHOA Thr19Asn[10-12] and GFP-RHOA Gly17Val fusions were analyzed. Activation of RHOA signaling triggered by GFP-RHOA overexpression and most prominently by the constitutively active GFP-RHOA Gln63Leu induced loss of adhesion and round cell morphology in HEK293T cells. (See FIG. 2A that illustrates GFP fluorescence micrographs of HEK293T cells expressing GFP, GFP-RHOA, constitutively active GFP-RHOA Q63L, dominant negative GFP-RHOA Thr19Asn and GFP-RHOA Gly17Val protein. Scale bar=10 μm).

Figure 2A:
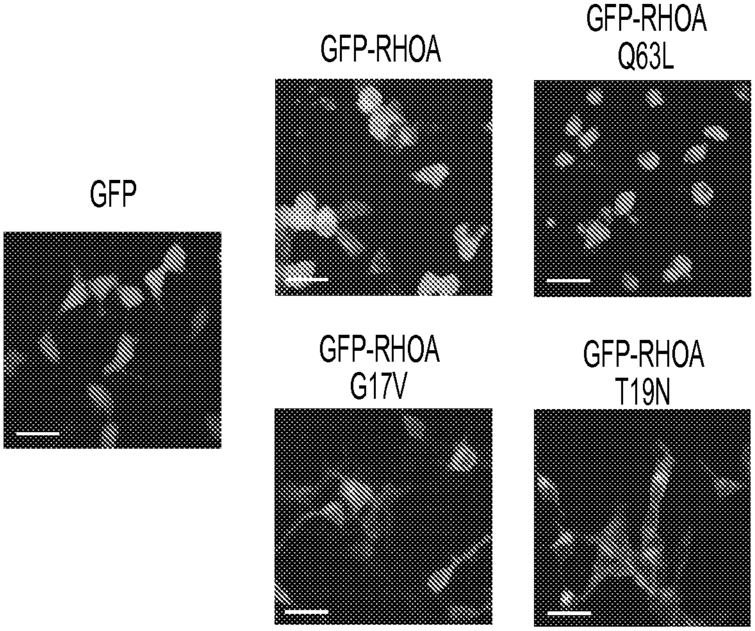
FIG. 2A-2E are graphs that illustrate the functional characterization of the RHOA p.Gly17Val allele according to an embodiment.

In contrast, cells expressing GFP-RHOA Gly17Val mimicked the phenotype of fibroblasts expressing dominant negative GFP-RHOA Thr19Asn, which showed increased elongated morphology and cellular protrusions. FIG. 2A. Similarly, immunofluorescence analysis of F-actin in HeLa cells showed increased stress fiber formation in cells expressing GFP-RHOA, which was markedly accentuated upon constitutive activation of RHOA signaling triggered by the GFP-RHOA Gln63Leu mutant. On the other hand, cells expressing GFP-RHOA Gly17Val or GFP-RHOA Thr19Asn showed decreased F-actin stress fibers, which is consistent with an inhibitory role of these mutations in RHO signaling. (See FIG. 2B that illustrates immunofluorescence analysis of stress fiber formation in HeLa cells expressing GFP, GFP-RHOA, GFP-RHOA Gln63Leu, GFP-RHOA Thr19Asn and GFP-RHOA Gly17Val protein shown in green. Actin fibers stained with phalloidin are shown in red and cell nuclei stained with DAPI are shown in blue. Scale bar=20 μm).

Following on these results, HA-tagged forms of wild type RHOA and RHOA Gly17Val in Jurkat T-cells were expressed and their capacity to interact with rhotekin tested, an effector protein that specifically recognizes the active GTP-bound form of RHOA[13] tested. Rhotekin pull down analysis showed significant activation of HA-RHOA in Jurkat cells in basal conditions, which was further increased upon serum stimulation. In contrast, rhotekin failed to interact with HA-RHOA Gly17Val. (See FIG. 2C that illustrates Western blot analysis of GTP-bound HA-RHOA in rhotekin pull downs from Jurkat cells expressing wild type HA-RHOA, constitutively active HA-RHOA Gln63Leu, dominant negative HA-RHOA Thr19Asn and the PTCL associated HA-RHOA Gly17Val protein. Similarly, rhotekin did not interact with dominant negative HA-RHOA Thr19Asn, while the constitutively active HA-RHOA Gln63Leu protein showed marked increased rhotekin binding.)

Given that rhotekin selectively binds to the GTP-bound form of RHOA, without being bound by theory, RHOA Gly17Val is locked in an inactive configuration devoid of GTP. A highly related RHOA Gly17Ala mutant protein capable of interacting with GEF proteins with high affinity, but resistant to GEF-induced GTP loading and activation has been described[14]. The capacity of GST-RHOA, GST-RHOA Gly17Val and GST-RHOA Gly17Ala recombinant proteins to bind to GTP was analyzed in response to MCF2L/DBS GEF stimulation in vitro using a fluorescence polarization assay. As expected, MCF2L/DBS triggered the loading of a fluorescent GTP analog (mant-GTP) into GST-RHOA. However, GST-RHOA Gly17Ala and GST-RHOA Gly17Val were resistant to the activity of this GEF factor. (See FIG. 2D that illustrates fluorescence polarization analysis of mant-GTP loading on vertical y-axis (100) to GST-RHOA, GST-RHOA Gly17Ala and GST-RHOA Gly17Val on horizontal x-axis (200) in time (min) in response to MCF2L/DBS stimulation.)

Figure 2B:
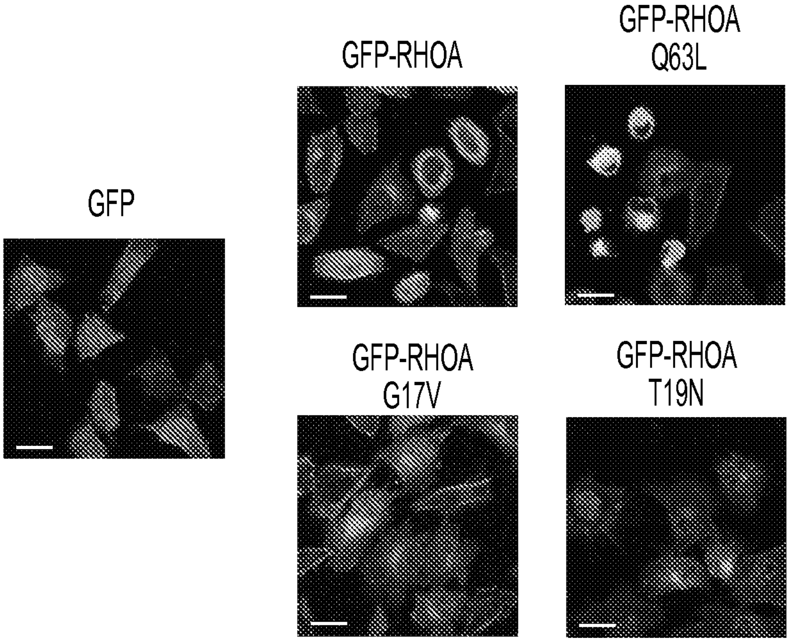
Figure 2C:
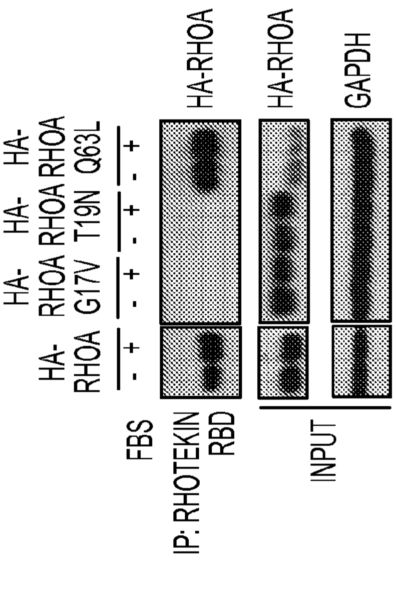
Figure 2D:
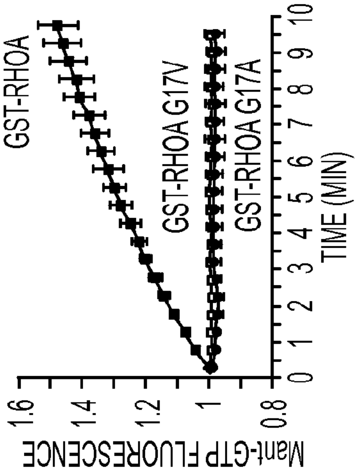
Figure 2E:
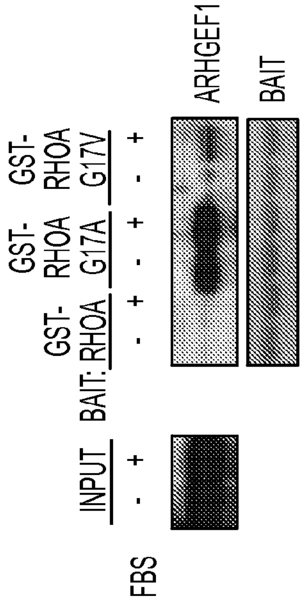

Finally, it was tested whether if RHOA Gly17Val could function as a high affinity GEF trap analogous to RHOA Gly17Ala sequestering activated GEF proteins in T-cells. GST pull down assays against ARHGEF1, a GEF factor highly expressed in T-cells, showed increased affinity of GST RHOA Gly17Val and most markedly GST-RHOA Gly17Ala compared to GST-RHOA wild type. (See FIG. 2E that illustrates Western blot analysis of ARHGEF1 GEF protein pulled down with GST-RHOA, GST-RHOA Gly17Ala and GST-RHOA Gly17Val from Jurkat cell lysates in basal conditions and upon serum (FBS) stimulation. Pounceau S staining of bait protein loading is shown at the bottom. Representative images from at least two independent experiments are shown in FIG. 2A and FIG. 2B. Data in FIG. 2D shows average±s.d. from triplicate samples.) Overall, these results are consistent with an inhibitory role for RHOA Gly17Val in RHO signaling potentially mediated by the sequestration of GEF factors and support a role for disruption of RHOA signaling in the pathogenesis of PTCLs.

Example 4

Identification of Recurrent Genetic Alterations and Fusion Oncogenes in PTCL To more broadly assess the presence of recurrent genetic alterations and fusion oncogenes in PTCL a cohort of 34 lymphoma samples by RNAseq was analyzed (Table 7). This analysis identified 4 samples harboring ALK fusion transcripts (3 NPM-ALK and 1 TFG-ALK), all corresponding to ALCL cases (Table 8). In addition the presence of candidate recurrent mutations in TET2, DNMT3A and IDH2 were detected and additional potential drivers of PTCL transformation were identified. (Table 9). Deep sequencing analysis of these and additional selected candidate genes including FYN, TET3, CDKN2A, PRKD2, RHOT2, SMARCAL1, ATM, B2M and CD58 in an extended panel of 125 PTCL DNAs including those analyzed by RNAseq showed a prominent role of mutations targeting DNA methylation and hydroxymethylation (TET2, DNMT3A, IDH2 and TET3) as shown before[15-17] and highlighted the role of defective DNA damage response (ATM) and escape from T-cell and NK cell immune surveillance (B2M and CD58) in the pathogenesis of PTCL. (See FIG. 3B and Table 5). In addition, the presence of new recurrent FYN kinase (NM_002037) mutations including a recurrent allele encoding a p.Arg176Cys substitution present in two PTCL NOS cases was detected, a mutation encoding a p.Leu174Arg alteration found in one AITL patient sample, in addition to the p.Tyr531His encoding allele identified via exome analysis in a PTCL NOS sample for an overall frequency of 3% (4/137) FYN mutations in our series. (See FIG. 3B that is a schematic representation of DNMT3A, TET2, TET3 and IDH2 proteins showing DNA methylation and hydroxymethylation related mutations in PTCL patients via exome sequencing (n=12) and amplicon resequencing (n=64). Solid circles indicate predicted amino acid substitutions. The position of truncating mutations is indicated with red open circles. Multiple circles in the same amino acid position account for multiple patients with the same variant. See also Table 5).

Example 5

Figure 4A:
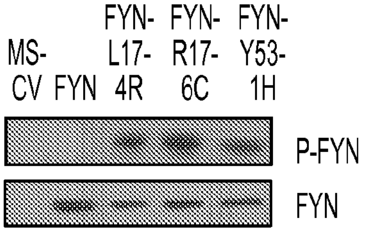
FIG. 4A-4J are graphs that illustrate structure modeling and functional characterization of FYN p.Leu174Arg, p.ARg176Cys, and p.Tyr531His mutations identified in PTCLs according to an embodiment.
Figure 4B:
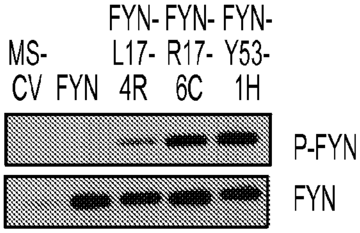

SRC Kinase Inhibition with Dasatinib Confers a Therapeutic Benefit in Selected PTCL Cases Harboring Activating Mutations in the FYN Kinase Gene The FYN tyrosine kinase is, with LCK, the predominant SRC family kinase found in T lymphocytes and plays an important role in T-cell activation upon T-cell receptor (TCR) stimulation[18]. Strikingly, FYN mutations found in PTCL are predicted to specifically disrupt the intramolecular inhibitory interaction of the FYN SH2 domain with C-terminal SRC kinase (CSK) phosphorylated FYN Tyr531. Consistently, expression of FYN Leu174Arg, FYN Arg176Cys and FYN Tyr531His in Rat1A cells resulted in increased levels of FYN activation compared with control cells expressing wild type FYN. (See FIG. 4A which illustrates an analysis of FYN activation via phospho-SRC immunoblotting in Rat1A cells infected wild type and PTCL associated FYN mutants expressing retroviruses.) (See FIG. 4B which illustrates an analysis of FYN activation via phosphor-SRC immunoblotting of FYN immunoprecipitates from Rat1A cells infected with wild type and PTCL associated FYN mutants expressing retroviruses.)

Figure 4C:
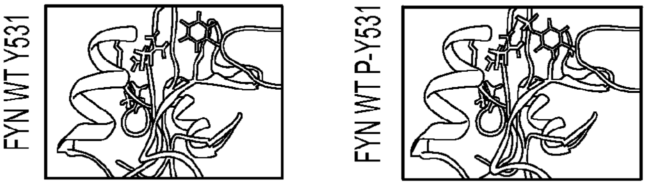
Figure 4D:
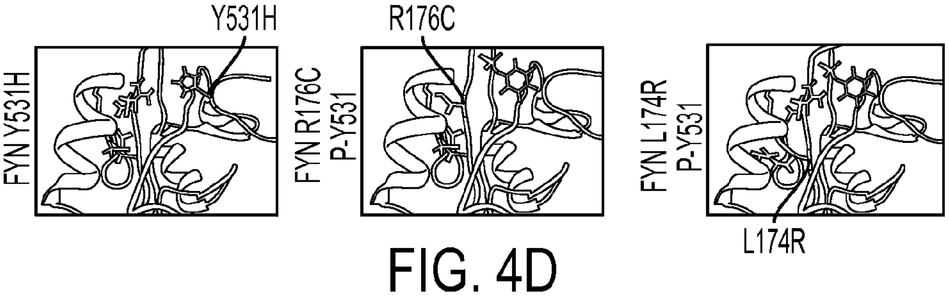
Figure 4E:
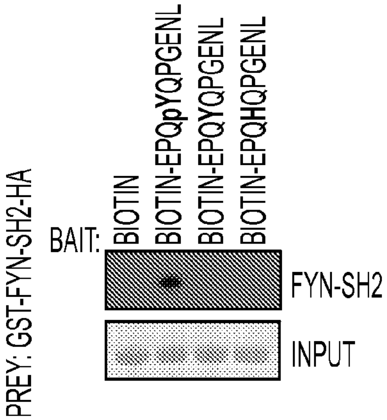

In addition, structure model analysis of FYN and FYN mutant proteins further supported this hypothesis. (See FIG. 4C which is a molecular ribbon representation of wild type FYN protein structure showing the positioning of the FYN SH2 domain and the C terminal Tyr531 phosphosite and FIG. 4D which illustrates structure modeling of FYN Tyr531His, FYN Arg176Cys and FYN Leu174Arg mutant proteins.) The interaction between GST-FYN-SH2 recombinant proteins and biotinylated C-terminal FYN peptides encompassing the position Tyr531 was analyzed. In these assays, wild type GST-FYN-SH2 was effectively pulled down with a Tyr531 phosphopeptide, but not with the corresponding unphosphorylated sequence or with a peptide containing a Tyr531His substitution. (See FIG. 4E which illustrates an analysis of wild type GST-SH2-FYN interaction with C-terminal FYN peptides corresponding to wild type Tyr531 FYN, wild type P-Tyr531 FYN and mutant Tyr531His FYN via Western blot analysis of GST-SH2-FYN proteins in streptavidin-biotin C-terminal FYN peptide pull downs. Experiment was replicated twice).

Figure 4F:
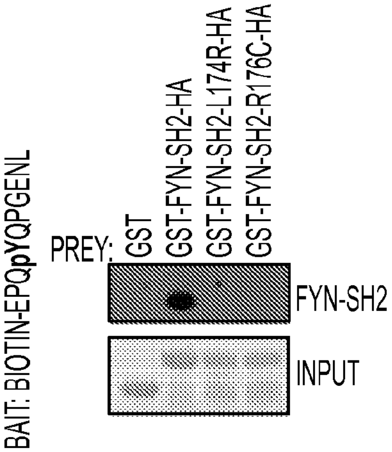
Figure 4G:
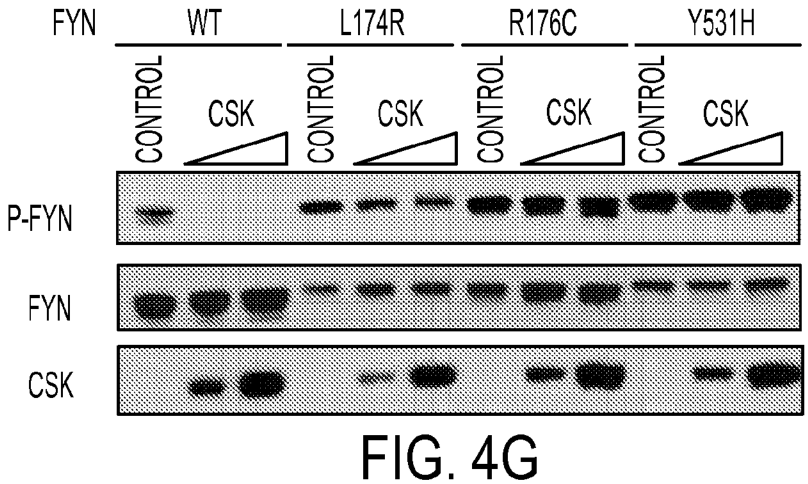

Similarly, the introduction of a Leu174Arg or a Arg176Cys substitution abrogated the interaction of GST-FYN-SH2 with the phospho-Y531 FYN C-terminal peptide. (See FIG. 4F which is an analysis of P-Tyr531 FYN C-terminal FYN peptide interaction with wild type GST-SH2-FYN and GST-SH2-FYN Leu174Arg and GST-SH2-FYN Arg176Cys mutant proteins via Western blot analysis of GST-SH2-FYN proteins in streptavidin-biotin P-Tyr531 C-terminal FYN peptide pull downs). Consistently, CSK effectively inhibited wild type FYN, but failed to abrogate the activity of the FYN mutant proteins. See FIG. 4G which is a Western blot analysis of CSK inhibition of FYN activity in HeLa cells expressing wild type and PTCL associated FYN mutant proteins).

Figure 4H:
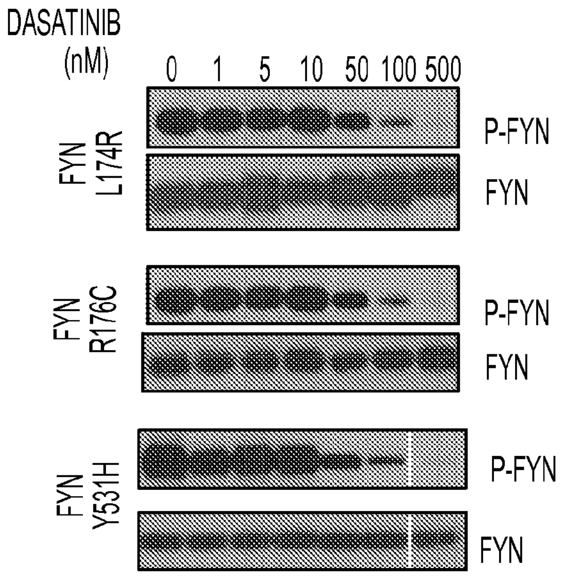
Figure 4I:
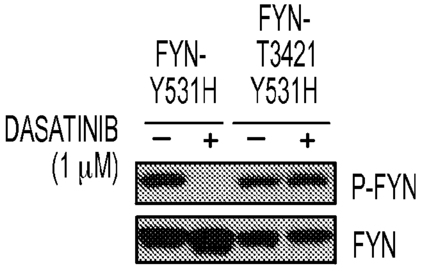
Figure 4J:
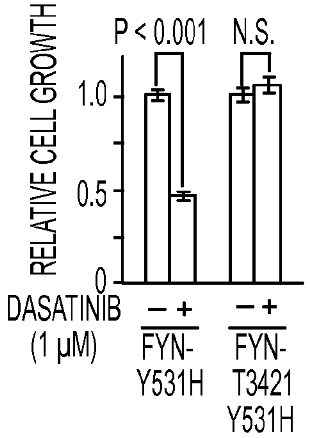

Finally, given the prominent role of kinase inhibitors as targeted therapies for tumors driven by constitutively active kinase oncogenes, the capacity of dasatinib, a multikinase inhibitor which blocks ABL1 and SRC kinases[19], to inhibit the activity of FYN Leu174Arg, FYN Arg176Cys and FYN Tyr531His mutant proteins was tested. Notably, in each case, dasatinib treatment induced dose dependent inhibition of FYN phosphorylation. See FIG. 4H which is a Western blot analysis of dasatinib inhibition of FYN activity in HEK293T cells expressing PTCL associated FYN mutant proteins). Moreover, dasatinib treatment impaired the growth of transformed Rat1A cells expressing the FYN Tyr531His mutant protein, but not that of cells expressing a drug-resistant gatekeeper mutant form of this kinase (FYN Thr342Ile Tyr531His) (See FIG. 4I and FIG. 4J which illustrate an analysis of dasatinib effects on FYN phosphorylation FIG. 4I and relative cell growth FIG. 4J in transformed Rat1A cells expressing the constitutively active FYN Tyr531His or the dasatinib-resistant FYN Thr342Ile Tyr531His double mutant protein. Data in FIG. 4J shows average±s.d. from triplicate samples. P values were calculated using the two-tailed Student's t test). Based on these results SRC kinase inhibition with dasatinib may confer a therapeutic benefit in selected PTCL cases harboring activating mutations in the FYN kinase gene.

TABLE 1

Exome sequencing samples, mutations and validation rates

| Sample | Diagnosis | Total Variants | Variants tested | Validated | Validation Rate |
|---|---|---|---|---|---|
| 1 | NK T-cell lymphoma | 25 | 16 | 15 | 93.8 |
| 2 | Enteropathy associated T-cell lymphoma | 46 | 25 | 23 | 92.0 |
| 4 | PTCL NOS | 9 | 8 | 8 | 100.0 |
| 5 | NK T-cell lymphoma | 19 | 13 | 13 | 100.0 |
| 11 | AITL | 16 | 13 | 12 | 92.3 |
| 24 | PTCL NOS | 22 | 7 | 6 | 85.7 |
| 26 | PTCL NOS | 4 | 4 | 2 | 50.0 |
| 28 | AITL | 6 | 6 | 4 | 66.7 |
| 29 | PTCL NOS | 57 | 12 | 12 | 100.0 |
| 31 | PTCL NOS | 15 | 5 | 5 | 100.0 |
| 33 | PTCL NOS | 22 | 6 | 3 | 50.0 |
| 35 | AITL | 47 | 6 | 6 | 100.0 |
| | Total: | 288 | 121 | 109 | 90% |

TABLE 2

Exome sequencing report

| Sample | Mean Depth | Capture Coverage | Coverage at Depth 10 | Coverage at Depth 20 | Coverage at Depth 30 | Number Reads | Number Reads Mapped | Percentage of Reads Mapped |
|---|---|---|---|---|---|---|---|---|
| 26N | 37.43 | 95.86 | 85.49 | 70.31 | 53.07 | 67569378 | 66107766 | 97.84 |
| 28N | 37.42 | 95.75 | 84.46 | 68.76 | 52.39 | 67682004 | 66296912 | 97.95 |
| 33N | 37.59 | 95.8 | 84.65 | 69.28 | 52.59 | 69114758 | 67778009 | 98.07 |
| 31T | 39.32 | 95.76 | 85.93 | 71.44 | 54.91 | 70311794 | 68788922 | 97.83 |
| 35T | 38.47 | 95.54 | 84.92 | 70.21 | 54.03 | 70427028 | 68527052 | 97.3 |
| 29N | 40.87 | 95.81 | 86.22 | 72.66 | 57.2 | 74232958 | 72803851 | 98.07 |
| 24N | 42.08 | 95.96 | 86.21 | 72.92 | 58.13 | 77177652 | 75463683 | 97.78 |
| 1T | 36.2 | 93.02 | 74.56 | 59.2 | 46.55 | 77517916 | 74482377 | 96.08 |
| 2T | 36.65 | 93.29 | 75.83 | 60.53 | 47.61 | 77893124 | 74896685 | 96.15 |
| 28T | 43.49 | 95.87 | 86.15 | 73.17 | 58.81 | 78250198 | 76578661 | 97.86 |
| 33T | 43 | 95.91 | 85.89 | 72.54 | 57.96 | 78300416 | 76688374 | 97.94 |
| 4N | 38.68 | 93.36 | 76.88 | 62.43 | 50.05 | 79154020 | 76455150 | 96.59 |
| 1N | 35.34 | 93.49 | 76.64 | 60.76 | 46.95 | 80677580 | 77655438 | 96.25 |
| 2N | 35.41 | 93.23 | 74.99 | 58.86 | 45.35 | 81765870 | 78428329 | 95.92 |
| 4T | 36.78 | 93.54 | 76.89 | 61.69 | 48.48 | 85568960 | 82404699 | 96.3 |
| 31N | 49.18 | 96.17 | 88.25 | 77.69 | 64.99 | 89169080 | 87289220 | 97.89 |
| 29T | 48.9 | 96.45 | 90.03 | 77.44 | 62.77 | 89992738 | 87965433 | 97.75 |
| 24T | 50.5 | 96.15 | 88.09 | 77.57 | 65.38 | 90103818 | 88242501 | 97.93 |
| 11T | 50.47 | 95.85 | 87.91 | 77.27 | 64.9 | 91738206 | 91001723 | 99.2 |
| 11N | 51.01 | 95.87 | 87.87 | 77.37 | 65.29 | 93093848 | 91349596 | 98.13 |
| 26T | 60.64 | 96.06 | 88.99 | 80.58 | 70.76 | 101349714 | 99284802 | 97.96 |
| 5N | 57.76 | 95.82 | 88.43 | 79.23 | 68.87 | 105793724 | 104280376 | 98.57 |
| 5T | 62.54 | 96.07 | 89.5 | 81.45 | 72.02 | 113384290 | 112515352 | 99.23 |
| 35N | 73.71 | 96.36 | 90.51 | 84.17 | 76.66 | 136858398 | 131900228 | 96.38 |

TABLE 3

Somatic variants identified by exome sequencing

| Sample | Chromosome | Position | Reference Sequence | Variant Sequence | Gene | Predicted Protein Change | Normal Variant Depth | Normal Total Depth | Normal Variant Frequency | Tumor Variant Depth | Tumor Total Depth | Tumor Variant Frequency |
|---|---|---|---|---|---|---|---|---|---|---|---|---|
| 1 | 5 | 112128200 | T | G | APC | p.L235V | 0 | 38 | 0 | 14 | 39 | 36 |
| 1 | 16 | 55853491 | G | A | CES1 | p.R288X | 0 | 115 | 0 | 36 | 140 | 26 |
| 1 | 8 | 75924750 | C | A | CRISPLD1 | p.P114Q | 0 | 60 | 0 | 26 | 60 | 43 |
| 1 | X | 41205629 | G | A | DDX3X | p.R488H | 0 | 20 | 0 | 16 | 24 | 67 |
| 1 | 15 | 51766626-51766637 | TGGGTGGGCTGC (SEQ ID NO: 4) | - | DMXL2 | p.del2372_2375 | 0 | 18 | 0 | 9 | 34 | 27 |
| 1 | 5 | 13883156 | G | A | DNAH5 | p.R1011W | 0 | 44 | 0 | 11 | 49 | 22 |
| 1 | 4 | 126389972 | A | G | FAT4 | p.M4069V | 0 | 59 | 0 | 18 | 56 | 32 |
| 1 | 5 | 170236610 | G | A | GABRP | p.G291R | 0 | 86 | 0 | 24 | 64 | 38 |
| 1 | 5 | 125801201 | C | T | GRAMD3 | p.A56V | 0 | 57 | 0 | 18 | 52 | 35 |
| 1 | 1 | 24663127 | C | T | GRHL3 | p.T141I | 0 | 56 | 0 | 24 | 61 | 39 |
| 1 | 4 | 175416703 | G | A | HPGD | p.A165V | 0 | 21 | 0 | 11 | 23 | 48 |
| 1 | 5 | 36110057 | T | A | LMBRD2 | p.N5941 | 0 | 85 | 0 | 13 | 59 | 22 |
| 1 | 14 | 47770738 | C | T | MDGA2 | p.R30H | 0 | 36 | 0 | 15 | 47 | 32 |
| 1 | 12 | 86377381 | G | A | MGAT4C | p.T72I | 0 | 83 | 0 | 25 | 74 | 34 |
| 1 | 5 | 7895847 | A | G | MTRR | p.I547V | 2 | 150 | 1 | 45 | 124 | 36 |
| 1 | 5 | 65084178 | C | T | NLN | p.Q398X | 0 | 93 | 0 | 41 | 118 | 35 |
| 1 | 2 | 27658094 | G | A | NRBP1 | p.V221M | 0 | 43 | 0 | 13 | 49 | 27 |
| 1 | 19 | 50411780 | C | A | NUP62 | p.E429X | 0 | 36 | 0 | 25 | 58 | 43 |
| 1 | 9 | 8518099 | G | A | PTPRD | p.S431L | 0 | 67 | 0 | 23 | 69 | 33 |
| 1 | 20 | 37150172 | C | T | RALGAPB | p.R484W | 0 | 106 | 0 | 30 | 96 | 31 |
| 1 | 3 | 78649432 | G | T | ROBO1 | p.T1552N | 0 | 179 | 0 | 52 | 160 | 32 |
| 1 | 1 | 231344748 | T | A | TRIM67 | p.N625K | 0 | 46 | 0 | 11 | 49 | 22 |

TABLE 3-continued

Somatic variants identified by exome sequencing

| Sample | Chromosome | Position | Reference Sequence | Variant Sequence | Gene | Predicted Protein Change | Normal Variant Depth | Normal Total Depth | Normal Variant Frequency | Tumor Variant Depth | Tumor Total Depth | Tumor Variant Frequency |
|---|---|---|---|---|---|---|---|---|---|---|---|---|
| 1 | 1 | 55194093-55194094 | CC | — | TTC4 | p.Q224fs | 0 | 32 | 0 | 8 | 19 | 42 |
| 1 | 1 | 215853636 | C | G | USH2A | p.G4050A | 0 | 69 | 0 | 27 | 71 | 38 |
| 1 | 5 | 167855753 | C | T | WWC1 | p.S654L | 0 | 13 | 0 | 8 | 21 | 38 |
| 2 | 17 | 66982305 | C | T | ABCA9 | p.R1403Q | 0 | 67 | 0 | 28 | 91 | 31 |
| 2 | X | 74273285 | T | C | ABCB7 | p.I728V | 0 | 42 | 0 | 21 | 26 | 81 |
| 2 | 22 | 41918879 | G | A | ACO2 | p.R395H | 0 | 39 | 0 | 17 | 49 | 35 |
| 2 | 17 | 48539898 | C | A | ACSF2 | p.N248K | 0 | 15 | 0 | 7 | 18 | 39 |
| 2 | X | 152815122 | C | A | ATP2B3 | p.S502R | 0 | 28 | 0 | 25 | 30 | 83 |
| 2 | 2 | 32738167 | A | G | BIRC6 | p.Y3505C | 0 | 99 | 0 | 31 | 75 | 41 |
| 2 | 16 | 65016030 | C | T | CDH11 | p.V392I | 1 | 66 | 2 | 25 | 48 | 52 |
| 2 | 2 | 189871078 | G | A | COL3A1 | p.R1034H | 0 | 27 | 0 | 16 | 30 | 53 |
| 2 | 2 | 189943820 | G | A | COL5A2 | p.P325L | 0 | 41 | 0 | 20 | 42 | 48 |
| 2 | 3 | 99513601 | C | A | COL8A1 | p.L286M | 0 | 20 | 0 | 7 | 16 | 44 |
| 2 | 1 | 110466772 | T | A | CSF1 | p.L510Q | 0 | 21 | 0 | 7 | 14 | 50 |
| 2 | 12 | 51115171 | A | G | DIP2B | p.Y1053C | 0 | 45 | 0 | 17 | 48 | 35 |
| 2 | 15 | 51766626-51766637 | TGGGTGGGCTGC (SEQ ID NO: 4) | — | DMXL2 | p.del2372_2375 | 0 | 19 | 0 | 7 | 19 | 38 |
| 2 | 5 | 13845086 | G | A | DNAH5 | p.R1711X | 0 | 52 | 0 | 20 | 55 | 36 |
| 2 | 13 | 99534159 | C | A | DOCK9 | p.V888F | 0 | 69 | 0 | 27 | 59 | 46 |
| 2 | 13 | 99534176 | G | T | DOCK9 | p.T882K | 0 | 83 | 0 | 25 | 52 | 48 |
| 2 | 20 | 35384120 | T | A | DSN1 | p.N280Y | 0 | 51 | 0 | 23 | 54 | 43 |
| 2 | 17 | 29632233 | C | T | EVI2B | p.R132H | 0 | 122 | 0 | 38 | 82 | 46 |
| 2 | 10 | 118441314 | C | T | HSPA12A | p.E304K | 0 | 32 | 0 | 8 | 24 | 33 |
| 2 | 19 | 55285052 | C | A | KIR2DL1 | p.A113D | 0 | 220 | 0 | 104 | 213 | 49 |

TABLE 3-continued

| Somatic variants identified by exome sequencing | | | | | | | | | | | | |
|---|---|---|---|---|---|---|---|---|---|---|---|---|
| Sample | Chromosome | Position | Reference Sequence | Variant Sequence | Gene | Predicted Protein Change | Normal Variant Depth | Normal Total Depth | Normal Variant Frequency | Tumor Variant Depth | Tumor Total Depth | Tumor Variant Frequency |
| 2 | 1 | 201351422 | C | A | LAD1 | p.R502S | 0 | 51 | 0 | 17 | 65 | 26 |
| 2 | 13 | 21565462 | G | T | LATS2 | p.L142M | 0 | 19 | 0 | 9 | 24 | 38 |
| 2 | 1 | 39800693 | T | G | MACF1 | p.S1251R | 0 | 58 | 0 | 16 | 45 | 36 |
| 2 | 7 | 2257638 | C | T | MAD1L1 | p.A213T | 0 | 22 | 0 | 7 | 13 | 54 |
| 2 | 12 | 86373596 | C | T | MGAT4C | p.R303H | 0 | 83 | 0 | 24 | 57 | 42 |
| 2 | 22 | 18374317 | A | C | MICAL3 | p.L543R | 0 | 74 | 0 | 22 | 37 | 59 |
| 2 | 17 | 41960308 | C | T | MPP2 | p.R139H | 0 | 90 | 0 | 34 | 99 | 34 |
| 2 | 1 | 203144496-2031445 | AGCCT | — | MYBPH | p.L102fs | 0 | 42 | 0 | 13 | 65 | 20 |
| 2 | 2 | 18745235 | G | C | NT5C1B | p.R494G | 0 | 35 | 0 | 21 | 41 | 51 |
| 2 | 9 | 107367248 | T | C | OR13C2 | p.I221V | 0 | 110 | 0 | 44 | 164 | 27 |
| 2 | 18 | 21912928 | G | T | OSBPL1A | p.D201E | 1 | 63 | 2 | 19 | 61 | 31 |
| 2 | 20 | 47248825 | G | A | PREX1 | p.R1506C | 0 | 65 | 0 | 20 | 48 | 42 |
| 2 | 5 | 120021906 | G | T | PRR16 | p.R116S | 1 | 68 | 1 | 24 | 55 | 44 |
| 2 | 8 | 18490167 | C | G | PSD3 | p.G789A | 0 | 76 | 0 | 22 | 57 | 39 |
| 2 | 9 | 8389314 | G | A | PTPRD | p.T1435I | 0 | 112 | 0 | 39 | 92 | 42 |
| 2 | 3 | 47058660 | T | G | SETD2 | p.T2540P | 0 | 62 | 0 | 16 | 57 | 28 |
| 2 | 3 | 47125211 | T | — | SETD2 | p.K2020fs | 0 | 92 | 0 | 36 | 90 | 40 |
| 2 | 12 | 100813653 | A | G | SLC17A8 | p.I496V | 0 | 43 | 0 | 9 | 19 | 47 |
| 2 | 2 | 217281008 | C | G | SMARCAL1 | p.S280R | 0 | 61 | 0 | 25 | 60 | 42 |
| 2 | 13 | 36909499 | C | G | SPG20 | p.A157P | 0 | 36 | 0 | 8 | 24 | 33 |
| 2 | 3 | 9034665 | T | C | SRGAP3 | p.K828R | 0 | 36 | 0 | 19 | 35 | 54 |
| 2 | 9 | 131083891 | G | C | TRUB2 | p.I76M | 0 | 18 | 0 | 14 | 34 | 41 |
| 2 | 9 | 12698469 | T | A | TYRP1 | p.S243T | 0 | 26 | 0 | 8 | 32 | 25 |

TABLE 3-continued

Somatic variants identified by exome sequencing

| Sample | Chromosome | Position | Reference Sequence | Variant Sequence | Gene | Predicted Protein Change | Normal Variant Depth | Normal Total Depth | Normal Variant Frequency | Tumor Variant Depth | Tumor Total Depth | Tumor Variant Frequency |
|---|---|---|---|---|---|---|---|---|---|---|---|---|
| 2 | 8 | 124113203 | C | G | WDR67 | p.L330V | 0 | 48 | 0 | 17 | 35 | 49 |
| 2 | 2 | 168107101 | A | G | XIRP2 | p.S3067G | 0 | 129 | 0 | 38 | 113 | 34 |
| 2 | 22 | 29383125-29383126 | TA | — | ZNRF3 | p.V21fs | 0 | 22 | 0 | 9 | 22 | 41 |
| 4 | 11 | 44297175 | G | T | ALX4 | p.P167H | 0 | 59 | 0 | 12 | 53 | 23 |
| 4 | 12 | 28605505 | G | A | CCDC91 | p.W340X | 0 | 89 | 0 | 16 | 83 | 19 |
| 4 | 7 | 107580491 | G | A | LAMB1 | p.A1235V | 0 | 92 | 0 | 23 | 72 | 32 |
| 4 | 2 | 133489544 | G | A | NCKAP5 | p.R418C | 0 | 36 | 0 | 11 | 28 | 39 |
| 4 | 20 | 49196373 | G | A | PTPN1 | p.W333X | 0 | 74 | 0 | 15 | 85 | 18 |
| 4 | 12 | 130897205 | C | T | RIMBP2 | p.R927K | 0 | 53 | 0 | 10 | 49 | 20 |
| 4 | 15 | 33893746 | G | A | RYR3 | p.V639I | 0 | 126 | 0 | 12 | 75 | 16 |
| 4 | 2 | 74328727 | C | — | TET3 | p.D1469fs | 0 | 12 | 0 | 12 | 18 | 67 |
| 4 | 3 | 9406768 | G | A | THUMPD3 | p.E6K | 1 | 54 | 2 | 14 | 84 | 17 |
| 5 | 20 | 49509941 | G | — | ADNP | p.P437fs | 0 | 126 | 0 | 25 | 116 | 22 |
| 5 | X | 77244158 | A | G | ATP7A | p.T181A | 0 | 254 | 0 | 58 | 211 | 27 |
| 5 | 16 | 1245957 | G | A | CACNA1H | p.V193M | 0 | 53 | 0 | 23 | 70 | 33 |
| 5 | 1 | 179983188 | G | A | CEP350 | p.D534N | 0 | 131 | 0 | 31 | 117 | 26 |
| 5 | 4 | 155157176 | A | C | DCHS2 | p.F2421L | 0 | 128 | 0 | 27 | 135 | 20 |
| 5 | 1 | 212798499 | G | A | FAM71A | p.G94S | 0 | 62 | 0 | 20 | 99 | 20 |
| 5 | 11 | 6458681 | C | A | HPX | p.C231F | 0 | 46 | 0 | 12 | 50 | 24 |
| 5 | 6 | 46801161 | T | C | MEP1A | p.W499R | 0 | 142 | 0 | 35 | 148 | 24 |
| 5 | 6 | 108370457 | G | A | OSTM1 | p.P317S | 0 | 73 | 0 | 18 | 58 | 31 |
| 5 | 10 | 74803661 | A | C | P4HA1 | p.Y378D | 0 | 208 | 0 | 43 | 216 | 20 |
| 5 | 1 | 100154588 | C | G | PALMD | p.H258D | 0 | 159 | 0 | 30 | 162 | 19 |

TABLE 3-continued

Somatic variants identified by exome sequencing

| Sample | Chromosome | Position | Reference Sequence | Variant Sequence | Gene | Predicted Protein Change | Normal Variant Depth | Normal Total Depth | Normal Variant Frequency | Tumor Variant Depth | Tumor Total Depth | Tumor Variant Frequency |
|---|---|---|---|---|---|---|---|---|---|---|---|---|
| 5 | 2 | 242046797 | C | T | PASK | p.W1262X | 0 | 64 | 0 | 23 | 97 | 24 |
| 5 | 5 | 140209034 | C | T | PCDHA6 | p.P453L | 0 | 133 | 0 | 23 | 123 | 19 |
| 5 | 19 | 55708532 | T | — | PTPRH | p.E648fs | 0 | 47 | 0 | 11 | 51 | 22 |
| 5 | 3 | 47163958 | T | A | SETD2 | p.N723I | 0 | 169 | 0 | 44 | 180 | 24 |
| 5 | 7 | 103061826 | G | T | SLC26A5 | p.L46M | 0 | 58 | 0 | 12 | 48 | 25 |
| 5 | 12 | 32906939 | C | T | YARS2 | p.G287D | 0 | 113 | 0 | 32 | 145 | 22 |
| 5 | 19 | 53667765 | C | T | ZNF665 | p.G660S | 0 | 149 | 0 | 38 | 206 | 18 |
| 5 | 19 | 13915868 | C | G | ZSWIM4 | p.Y206X | 0 | 60 | 0 | 14 | 42 | 33 |
| 11 | 9 | 100070397 | C | A | C9orf174 | p.Q201K | 0 | 44 | 0 | 15 | 60 | 25 |
| 11 | 22 | 29083962 | G | C | CHEK2 | p.R519G | 0 | 12 | 0 | 11 | 20 | 55 |
| 11 | 5 | 173317362 | A | T | CPEB4 | p.N209I | 0 | 161 | 0 | 23 | 120 | 19 |
| 11 | 7 | 99364005 | T | C | CYP3A4 | p.H287R | 0 | 71 | 0 | 23 | 58 | 40 |
| 11 | 14 | 76948373 | C | T | ESRRB | p.R177X | 0 | 20 | 0 | 17 | 44 | 39 |
| 11 | 1 | 21106912 | C | A | HP1BP3 | p.G8C | 0 | 27 | 0 | 13 | 30 | 43 |
| 11 | 19 | 49573994 | T | G | KCNA7 | p.S233R | 0 | 54 | 0 | 12 | 59 | 20 |
| 11 | 1 | 46745164 | C | T | LRRC41 | p.G715R | 0 | 142 | 0 | 21 | 133 | 16 |
| 11 | 7 | 143748383 | G | A | OR2A5 | p.V297I | 0 | 138 | 0 | 24 | 126 | 19 |
| 11 | 5 | 140865561 | G | A | PCDHGC4 | p.S274N | 0 | 75 | 0 | 20 | 89 | 22 |
| 11 | 17 | 2866725 | A | C | RAP1GAP2 | p.D83A | 0 | 148 | 0 | 33 | 160 | 21 |
| 11 | 3 | 49412973 | C | A | RHOA | p.G17V | 0 | 104 | 0 | 19 | 103 | 18 |
| 11 | 19 | 51215204 | C | A | SHANK1 | p.Q320H | 0 | 92 | 0 | 18 | 83 | 22 |
| 11 | 8 | 38646250 | C | G | TACC1 | p.P64A | 0 | 85 | 0 | 19 | 103 | 18 |
| 11 | 10 | 123970755 | A | G | TACC2 | p.D418G | 0 | 48 | 0 | 14 | 71 | 20 |

TABLE 3-continued

Somatic variants identified by exome sequencing

| Sample | Chromosome | Position | Reference Sequence | Variant Sequence | Gene | Predicted Protein Change | Normal Variant Depth | Normal Total Depth | Normal Variant Frequency | Tumor Variant Depth | Tumor Total Depth | Tumor Variant Frequency |
|---|---|---|---|---|---|---|---|---|---|---|---|---|
| 11 | 2 | 217724657 | C | T | TNP1 | p.R34H | 0 | 116 | 0 | 30 | 130 | 23 |
| 24 | 4 | 57220268 | C | G | AASDH | p.L440F | 0 | 34 | 0 | 29 | 74 | 39 |
| 24 | 5 | 33534970 | T | C | ADAMTS12 | p.K1525R | 0 | 49 | 0 | 31 | 96 | 32 |
| 24 | 7 | 134133762 | G | A | AKR1B1 | p.P180L | 2 | 168 | 1 | 73 | 202 | 36 |
| 24 | 7 | 34118720-34118730 | CGCATCGCGCT (SEQ ID NO: 5) | — | BMPER | p.L447fs | 0 | 44 | 0 | 12 | 67 | 18 |
| 24 | 12 | 2743521 | T | C | CACNA1C | p.V1296A | 0 | 35 | 0 | 8 | 41 | 20 |
| 24 | 2 | 56570065 | A | T | CCDC85A | p.E431V | 0 | 33 | 0 | 13 | 35 | 37 |
| 24 | 18 | 50683813 | G | A | DCC | p.R450H | 0 | 61 | 0 | 24 | 102 | 24 |
| 24 | 1 | 22923963 | G | A | EPHA8 | p.G642S | 0 | 82 | 0 | 27 | 92 | 29 |
| 24 | 6 | 54804836 | A | G | FAM83B | p.H356R | 0 | 45 | 0 | 25 | 70 | 36 |
| 24 | 6 | 111982965 | A | G | FYN | p.Y531H | 0 | 73 | 0 | 51 | 129 | 40 |
| 24 | 6 | 27860929 | G | A | HIST1H2AM | | 1 | 49 | 2 | 17 | 52 | 33 |
| 24 | 4 | 88226420 | G | C | HSD17B13 | p.Q285E | 0 | 34 | 0 | 12 | 33 | 36 |
| 24 | 3 | 49163236 | C | T | LAMB2 | p.R811H | 0 | 44 | 0 | 14 | 39 | 36 |
| 24 | 1 | 86820377 | T | G | ODF2L | p.535_splice | 0 | 116 | 0 | 22 | 115 | 19 |
| 24 | 4 | 183652137 | G | A | ODZ3 | p.V938M | 0 | 148 | 0 | 61 | 209 | 29 |
| 24 | 17 | 74286162 | T | C | QRICH2 | p.V1072fs | 0 | 37 | 0 | 18 | 50 | 36 |
| 24 | 20 | 19701645 | T | C | SLC24A3 | p.V599A | 0 | 35 | 0 | 13 | 44 | 30 |
| 24 | 22 | 24135786 | A | | SMARCB1 | p.L82fs | 0 | 127 | 0 | 105 | 147 | 71 |
| 24 | 6 | 43144376 | A | G | SRF | p.D378G | 0 | 61 | 0 | 22 | 66 | 33 |
| 24 | 6 | 152655318 | C | T | SYNE1 | p.E4136K | 0 | 106 | 0 | 43 | 123 | 35 |
| 24 | 14 | 104460719 | A | | TDRD9 | p.K411fs | 3 | 267 | 1 | 105 | 278 | 38 |
| 24 | 3 | 126219656 | G | T | UROC1 | p.Q343K | 0 | 53 | 0 | 19 | 73 | 26 |

TABLE 3-continued

Somatic variants identified by exome sequencing

| Sample | Chromosome | Position | Reference Sequence | Variant Sequence | Gene | Predicted Protein Change | Normal Variant Depth | Normal Total Depth | Normal Variant Frequency | Tumor Variant Depth | Tumor Total Depth | Tumor Variant Frequency |
|---|---|---|---|---|---|---|---|---|---|---|---|---|
| 26 | 17 | 8110558 | G | A | AURKB | p.Q112X | 0 | 28 | 0 | 9 | 55 | 16 |
| 26 | X | 107977174 | A | G | IRS4 | p.S801P | 1 | 91 | 1 | 23 | 134 | 17 |
| 26 | 11 | 48328658 | C | T | OR4S1 | p.A295V | 0 | 31 | 0 | 7 | 35 | 20 |
| 26 | 4 | 106156729 | C | T | TET2 | p.R544X | 0 | 68 | 0 | 16 | 99 | 16 |
| 28 | 6 | 36178013 | C | A | BRPF3 | p.F629L | 0 | 36 | 0 | 7 | 31 | 23 |
| 28 | 4 | 107845707 | A | T | DKK2 | p.I175K | 0 | 81 | 0 | 21 | 119 | 18 |
| 28 | 11 | 12225829-12225839 | GCGCACTGCCA (SEQ ID NO: 6) | — | MICAL2 | p.L99fs | 0 | 23 | 0 | 12 | 29 | 42 |
| 28 | 14 | 79181122 | C | T | NRXN3 | p.R189C | 2 | 151 | 1 | 37 | 229 | 16 |
| 28 | 4 | 106157329 | C | T | TET2 | p.Q744X | 0 | 58 | 0 | 12 | 63 | 19 |
| 28 | 4 | 106196920.5 | — | A | TET2 | p.Y1751fs | 1 | 95 | 1 | 12 | 64 | 19 |
| 29 | 8 | 39604117 | T | G | ADAM2 | p.K683T | 1 | 88 | 1 | 21 | 62 | 34 |
| 29 | 22 | 26118329 | G | A | ADRBK2 | p.R660H | 0 | 68 | 0 | 24 | 101 | 24 |
| 29 | 2 | 60688212 | G | A | BCL11A | p.S612L | 0 | 20 | 0 | 25 | 68 | 37 |
| 29 | 5 | 41154007 | C | A | C6 | p.C732F | 0 | 54 | 0 | 11 | 19 | 58 |
| 29 | 6 | 74073369 | G | A | C6orf221 | p.R147H | 0 | 28 | 0 | 19 | 62 | 31 |
| 29 | 5 | 19473609 | C | A | CDH18 | p.R700I | 0 | 59 | 0 | 7 | 21 | 33 |
| 29 | 9 | 21971120 | G | A | CDKN2A | p.R80X | 0 | 23 | 0 | 27 | 42 | 64 |
| 29 | 8 | 139606338 | G | A | COL22A1 | p.R1513W | 0 | 27 | 0 | 31 | 69 | 45 |
| 29 | 9 | 135527863 | T | C | DDX31 | p.Y307C | 0 | 27 | 0 | 10 | 31 | 32 |
| 29 | 1 | 46976163 | C | T | DMBX1 | p.A57V | 0 | 24 | 0 | 17 | 68 | 25 |
| 29 | 19 | 36002389 | C | T | DMKN | p.S281N | 0 | 11 | 0 | 6 | 13 | 46 |
| 29 | 17 | 11522927 | A | C | DNAH9 | p.K393N | 2 | 159 | 1 | 86 | 238 | 36 |
| 29 | 8 | 16974058 | T | A | EFHA2 | p.S491R | 0 | 99 | 0 | 28 | 88 | 32 |

TABLE 3-continued

| Somatic variants identified by exome sequencing | | | | | | | | | | | | |
|---|---|---|---|---|---|---|---|---|---|---|---|---|
| Sample | Chromosome | Position | Reference Sequence | Variant Sequence | Gene | Predicted Protein Change | Normal Variant Depth | Normal Total Depth | Normal Variant Frequency | Tumor Variant Depth | Tumor Total Depth | Tumor Variant Frequency |
| 29 | 3 | 184298857 | G | A | EPHB3 | p.R879Q | 0 | 70 | 0 | 51 | 142 | 36 |
| 29 | 7 | 100410753 | C | T | EPHB4 | p.V612I | 0 | 52 | 0 | 32 | 99 | 32 |
| 29 | 1 | 152328782 | G | T | FLG2 | p.Q494K | 3 | 290 | 1 | 51 | 159 | 32 |
| 29 | 19 | 46375477 | G | — | FOXA3 | p.A72fs | 0 | 33 | 0 | 31 | 81 | 38 |
| 29 | 19 | 46375478 | C | A | FOXA3 | p.A72D | 0 | 32 | 0 | 31 | 79 | 39 |
| 29 | 17 | 63049705 | A | G | GNA13 | p.F142S | 0 | 125 | 0 | 85 | 120 | 71 |
| 29 | 12 | 13102565 | C | G | GPRC5D | p.V252L | 0 | 64 | 0 | 35 | 112 | 31 |
| 29 | 6 | 126075618 | C | A | HEY2 | p.A85E | 0 | 23 | 0 | 6 | 22 | 27 |
| 29 | 5 | 75923301 | G | A | IQGAP2 | p.V530M | 0 | 123 | 0 | 44 | 133 | 33 |
| 29 | 15 | 69709810 | C | T | KIF23 | p.P57L | 0 | 75 | 0 | 24 | 63 | 38 |
| 29 | 2 | 136575474 | A | G | LCT | p.F382L | 0 | 80 | 0 | 65 | 199 | 33 |
| 29 | 6 | 160953643 | G | A | LPA | p.L1961F | 0 | 42 | 0 | 7 | 21 | 33 |
| 29 | X | 26157169 | C | T | MAGEB18 | p.Q23X | 0 | 36 | 0 | 21 | 33 | 64 |
| 29 | 3 | 152164538 | T | G | MBNL1 | p.F285V | 1 | 63 | 2 | 19 | 51 | 37 |
| 29 | 1 | 3432010 | C | T | MEGF6 | p.C229Y | 0 | 19 | 0 | 8 | 27 | 30 |
| 29 | 11 | 74716804 | C | T | NEU3 | p.S218F | 2 | 157 | 1 | 71 | 203 | 35 |
| 29 | 16 | 50642235 | C | T | NKD1 | p.L75F | 0 | 51 | 0 | 31 | 99 | 31 |
| 29 | 19 | 54313017 | G | — | NLRP12 | p.H632fs | 0 | 30 | 0 | 36 | 98 | 37 |
| 29 | 19 | 54313019 | G | T | NLRP12 | p.H632N | 0 | 34 | 0 | 33 | 98 | 34 |
| 29 | 18 | 31537339 | C | T | NOL4 | p.R460H | 0 | 38 | 0 | 6 | 11 | 55 |
| 29 | 11 | 57947703 | T | G | OR9Q1 | p.S263A | 1 | 80 | 1 | 26 | 65 | 40 |
| 29 | 10 | 118365033 | G | T | PNLIPRP1 | p.K436N | 0 | 52 | 0 | 9 | 48 | 19 |
| 29 | 19 | 47184939 | C | T | PRKD2 | p.V680M | 0 | 24 | 0 | 9 | 36 | 25 |
| 29 | 8 | 74209432 | G | A | RDH10 | p.G98E | 0 | 23 | 0 | 6 | 21 | 29 |

TABLE 3-continued

Somatic variants identified by exome sequencing

| Sample | Chromosome | Position | Reference Sequence | Variant Sequence | Gene | Predicted Protein Change | Normal Variant Depth | Normal Total Depth | Normal Variant Frequency | Tumor Variant Depth | Tumor Total Depth | Tumor Variant Frequency |
|---|---|---|---|---|---|---|---|---|---|---|---|---|
| 29 | 6 | 7229345 | A | G | RREB1 | p.H338R | 0 | 21 | 0 | 24 | 65 | 37 |
| 29 | 15 | 34103203 | G | A | RYR3 | p.E3408K | 0 | 52 | 0 | 16 | 53 | 30 |
| 29 | 1 | 153536274 | T | G | S100A2 | p.K26T | 0 | 25 | 0 | 20 | 52 | 38 |
| 29 | 18 | 76754215 | C | T | SALL3 | p.P742S | 0 | 21 | 0 | 17 | 51 | 33 |
| 29 | 4 | 119686039 | A | G | SEC24D | p.I405T | 1 | 110 | 1 | 11 | 33 | 33 |
| 29 | X | 135092656 | G | A | SLC9A6 | p.A287T | 0 | 68 | 0 | 18 | 55 | 33 |
| 29 | 17 | 76354965 | C | T | SOCS3 | p.R71H | 0 | 11 | 0 | 13 | 18 | 72 |
| 29 | 1 | 204092264 | C | T | SOX13 | p.P387S | 0 | 46 | 0 | 51 | 155 | 33 |
| 29 | 2 | 220346376 | G | A | SPEG | p.E1847K | 0 | 25 | 0 | 12 | 35 | 34 |
| 29 | 2 | 191844538 | C | T | STAT1 | p.E563K | 0 | 35 | 0 | 26 | 72 | 36 |
| 29 | 6 | 159183207 | A | C | SYTL3 | p.K437T | 0 | 17 | 0 | 18 | 57 | 32 |
| 29 | 10 | 123970184 | A | G | TACC2 | p.T228A | 0 | 55 | 0 | 35 | 103 | 34 |
| 29 | 4 | 106193931 | C | T | TET2 | p.R1465X | 0 | 28 | 0 | 10 | 22 | 45 |
| 29 | 4 | 106197360 | C | T | TET2 | p.S1898F | 0 | 55 | 0 | 27 | 60 | 45 |
| 29 | 6 | 75994131 | A | T | TMEM30A | p.175N | 0 | 40 | 0 | 27 | 75 | 36 |
| 29 | 19 | 6853957-6853961 | GTGGG | — | VAV1 | p.778_splice | 1 | 78 | 1 | 40 | 85 | 47 |
| 29 | X | 48546807 | G | A | WAS | p.G299E | 0 | 17 | 0 | 12 | 18 | 67 |
| 29 | 1 | 29069007 | G | A | YTHDF2 | p.W75X | 0 | 91 | 0 | 54 | 185 | 29 |
| 29 | 3 | 147113643 | G | T | ZIC4 | p.H228Q | 0 | 69 | 0 | 52 | 137 | 38 |
| 29 | 19 | 21991695 | A | T | ZNF43 | p.S382T | 0 | 116 | 0 | 29 | 83 | 35 |
| 31 | 15 | 50273399 | T | A | ATP8B4 | p.spl | 1 | 42 | 2 | 13 | 38 | 34 |
| 31 | 5 | 24537624 | C | A | CDH10 | p.A131S | 1 | 85 | 1 | 20 | 75 | 27 |
| 31 | 19 | 10886538 | C | A | DNM2 | p.A182D | 1 | 90 | 1 | 16 | 68 | 24 |

TABLE 3-continued

Somatic variants identified by exome sequencing

| Sample | Chromosome | Position | Reference Sequence | Variant Sequence | Gene | Predicted Protein Change | Normal Variant Depth | Normal Total Depth | Normal Variant Frequency | Tumor Variant Depth | Tumor Total Depth | Tumor Variant Frequency |
|---|---|---|---|---|---|---|---|---|---|---|---|---|
| 31 | 12 | 15777248 | C | A | EPS8 | p.R713L | 0 | 87 | 0 | 9 | 50 | 18 |
| 31 | 2 | 153504391 | C | T | FMNL2 | p.S1084F | 0 | 171 | 0 | 41 | 147 | 28 |
| 31 | 6 | 146673505 | G | A | GRM1 | p.V436M | 0 | 128 | 0 | 34 | 127 | 27 |
| 31 | 14 | 63269157 | C | G | KCNH5 | p.C571S | 2 | 94 | 2 | 13 | 61 | 21 |
| 31 | 11 | 56128510 | G | A | OR8.11 | p.R263Q | 1 | 141 | 1 | 23 | 92 | 25 |
| 31 | 1 | 176708873 | G | A | PAPPA2 | p.V1304I | 0 | 39 | 0 | 11 | 33 | 33 |
| 31 | 3 | 49412973 | C | A | RHOA | p.G17V | 1 | 110 | 1 | 17 | 90 | 19 |
| 31 | 6 | 72960072 | G | T | RIMS1 | p.V761L | 0 | 117 | 0 | 23 | 80 | 29 |
| 31 | 9 | 35555303 | C | T | RUSC2 | p.T754I | 0 | 68 | 0 | 9 | 48 | 19 |
| 31 | 5 | 476373 | G | T | SLC9A3 | p.L671I | 0 | 60 | 0 | 8 | 37 | 22 |
| 31 | X | 54956981 | C | T | TRO | p.T1275I | 0 | 28 | 0 | 7 | 22 | 32 |
| 31 | 19 | 38090531 | T | A | ZNF540 | p.L5X | 1 | 88 | 1 | 12 | 71 | 17 |
| 33 | 16 | 89178496-89178529 | GTAGGTTTGGGAAAGTTCTTAAGTTCTGAAACG (SEQ ID NO: 7) | — | ACSF3 | p.85_splice | 0 | 116 | 0 | 28 | 151 | 19 |
| 33 | 8 | 39044429 | A | G | ADAM32 | p.Y306C | 0 | 88 | 0 | 108 | 178 | 61 |
| 33 | 11 | 108236087 | G | A | ATM | p.R3008H | 0 | 67 | 0 | 24 | 26 | 92 |
| 33 | 15 | 83932492 | G | A | BNC1 | p.T504M | 0 | 41 | 0 | 28 | 47 | 60 |
| 33 | 1 | 170934373 | A | G | C1orf129 | p.T153A | 0 | 53 | 0 | 27 | 67 | 40 |
| 33 | 9 | 111909356 | A | G | C9orf4 | p.V197A | 0 | 73 | 0 | 30 | 76 | 39 |
| 33 | 16 | 66949138 | C | T | CDH16 | p.A190T | 0 | 36 | 0 | 8 | 22 | 36 |
| 33 | 16 | 58579389 | G | C | CNOT1 | p.S1338C | 0 | 49 | 0 | 17 | 42 | 40 |
| 33 | 8 | 113318352 | G | A | CSMD3 | p.T2652M | 0 | 59 | 0 | 29 | 99 | 29 |
| 33 | 5 | 13841805 | G | C | DNAH5 | p.A1827G | 0 | 39 | 0 | 23 | 48 | 48 |

TABLE 3-continued

| Somatic variants identified by exome sequencing | | | | | | | | | | | | |
|---|---|---|---|---|---|---|---|---|---|---|---|---|
| Sample | Chromosome | Position | Reference Sequence | Variant Sequence | Gene | Predicted Protein Change | Normal Variant Depth | Normal Total Depth | Normal Variant Frequency | Tumor Variant Depth | Tumor Total Depth | Tumor Variant Frequency |
| 33 | 10 | 97583090 | C | T | ENTPD1 | p.T38I | 0 | 53 | 0 | 21 | 48 | 44 |
| 33 | 16 | 10911993 | T | A | FAM18A | p.E19V | 0 | 17 | 0 | 7 | 17 | 41 |
| 33 | 4 | 41621228 | G | A | LIMCH1 | p.D82N | 0 | 281 | 0 | 154 | 292 | 53 |
| 33 | 19 | 36341959 | C | T | NPHS1 | p.A144T | 0 | 24 | 0 | 12 | 34 | 35 |
| 33 | 9 | 102590388 | T | G | NR4A3 | p.Y33D | 0 | 47 | 0 | 25 | 47 | 53 |
| 33 | 6 | 24145869 | G | A | NRSN1 | p.E95K | 0 | 64 | 0 | 29 | 65 | 45 |
| 33 | 9 | 125437890 | T | C | OR1L3 | p.L161P | 0 | 141 | 0 | 67 | 145 | 46 |
| 33 | 18 | 8378362 | A | G | PTPRM | p.N1175D | 0 | 47 | 0 | 22 | 53 | 42 |
| 33 | 16 | 720287 | G | A | RHOT2 | p.R123Q | 0 | 53 | 0 | 26 | 53 | 49 |
| 33 | 17 | 33591281-33591284 | AATA | — | SLFN5 | p.L406fs | 0 | 46 | 0 | 28 | 63 | 44 |
| 33 | 1 | 16264330-16264332 | CCT | — | SPEN | p.G3511fs | 0 | 48 | 0 | 14 | 67 | 21 |
| 33 | 19 | 13941670 | A | C | ZSWIM4 | p.T926P | 0 | 33 | 0 | 10 | 42 | 24 |
| 35 | 2 | 29917811 | T | C | ALK | p.Q286R | 0 | 124 | 0 | 12 | 51 | 24 |
| 35 | 22 | 18095633 | T | C | ATP6V1E1 | p.N52S | 1 | 68 | 1 | 11 | 34 | 32 |
| 35 | 12 | 54651431 | C | T | CBX5 | p.G2R | 0 | 119 | 0 | 8 | 45 | 18 |
| 35 | 3 | 126142456 | A | G | CCDC37 | p.S419G | 0 | 101 | 0 | 12 | 44 | 27 |
| 35 | 2 | 204591454 | T | G | CD28 | p.F51V | 0 | 110 | 0 | 18 | 81 | 22 |
| 35 | 2 | 208432266 | T | G | CREB1 | p.L114R | 0 | 76 | 0 | 6 | 26 | 23 |
| 35 | 5 | 159656585 | C | A | FABP6 | p.F56L | 0 | 290 | 0 | 45 | 133 | 34 |
| 35 | 4 | 77189838 | G | A | FAM47E | p.A196T | 0 | 126 | 0 | 11 | 47 | 23 |
| 35 | 18 | 29848157 | T | C | FAM59A | p.K769E | 0 | 77 | 0 | 10 | 47 | 21 |
| 35 | 1 | 149858181 | G | A | HIST2H2BE | p.P4S | 0 | 38 | 0 | 13 | 67 | 19 |

TABLE 3-continued

| Somatic variants identified by exome sequencing | | | | | | | | | | | | |
|---|---|---|---|---|---|---|---|---|---|---|---|---|
| Sample | Chromosome | Position | Reference Sequence | Variant Sequence | Gene | Predicted Protein Change | Normal Variant Depth | Normal Total Depth | Normal Variant Frequency | Tumor Variant Depth | Tumor Total Depth | Tumor Variant Frequency |
| 35 | 21 | 41137738 | A | C | IGSF5 | p.Q126P | 0 | 21 | 0 | 5 | 14 | 36 |
| 35 | 12 | 26733042 | T | G | ITPR2 | p.E1476A | 0 | 117 | 0 | 9 | 55 | 16 |
| 35 | 3 | 124374477 | A | G | KALRN | p.E244G | 1 | 131 | 1 | 11 | 62 | 18 |
| 35 | 21 | 31709524 | C | A | KRTAP27-1 | p.E155X | 0 | 213 | 0 | 16 | 93 | 17 |
| 35 | 6 | 129722467 | A | C | LAMA2 | p.E1848D | 0 | 176 | 0 | 17 | 90 | 19 |
| 35 | 2 | 48915495 | T | C | LHCGR | p.R481G | 0 | 95 | 0 | 9 | 44 | 20 |
| 35 | 17 | 35297807 | C | T | LHX1 | p.H131Y | 0 | 46 | 0 | 7 | 28 | 25 |
| 35 | 12 | 59271500 | T | G | LRIG3 | p.T680P | 1 | 90 | 1 | 11 | 53 | 21 |
| 35 | 15 | 75656502 | A | G | MAN2C1 | p.F210L | 0 | 44 | 0 | 5 | 12 | 42 |
| 35 | 10 | 54530546 | C | A | MBL2 | p.G63V | 0 | 203 | 0 | 14 | 87 | 16 |
| 35 | 6 | 54095689 | C | A | MLIP | p.L431I | 0 | 188 | 0 | 19 | 94 | 20 |
| 35 | 21 | 26965121 | T | C | MRPL39 | p.308_splice | 0 | 62 | 0 | 7 | 40 | 18 |
| 35 | 11 | 1269640 | A | C | MUC5B | p.T3847P | 2 | 248 | 1 | 20 | 122 | 16 |
| 35 | 10 | 95072924 | T | G | MYOF | p.K1901N | 0 | 295 | 0 | 33 | 160 | 21 |
| 35 | 1 | 236205314 | C | T | NID1 | p.G344E | 0 | 48 | 0 | 18 | 56 | 32 |
| 35 | 1 | 200143338 | A | C | NR5A2 | p.X496Y | 0 | 20 | 0 | 16 | 37 | 43 |
| 35 | 1 | 205275372 | T | C | NUAK2 | p.S212G | 0 | 46 | 0 | 11 | 52 | 21 |
| 35 | 19 | 9965295 | T | G | OLFM2 | p.N311T | 0 | 42 | 0 | 8 | 35 | 23 |
| 35 | 11 | 58170764 | T | G | OR5B3 | p.N40T | 0 | 182 | 0 | 19 | 73 | 26 |
| 35 | 5 | 140307847 | A | C | PCDHAC1 | p.N457T | 0 | 189 | 0 | 30 | 93 | 32 |
| 35 | 6 | 144093402 | A | G | PHACTR2 | p.T323A | 0 | 61 | 0 | 7 | 37 | 19 |
| 35 | 4 | 129789105 | T | G | PHF17 | p.L533R | 0 | 78 | 0 | 11 | 33 | 33 |
| 35 | 10 | 95987122 | A | C | PLCE1 | p.E623D | 2 | 86 | 2 | 13 | 49 | 27 |
| 35 | 7 | 66262494 | G | A | RABGEF1 | p.461_splice | 0 | 96 | 0 | 13 | 37 | 35 |

TABLE 3-continued

| Somatic variants identified by exome sequencing | | | | | | | | | | | | |
|---|---|---|---|---|---|---|---|---|---|---|---|---|
| Sample | Chromosome | Position | Reference Sequence | Variant Sequence | Gene | Predicted Protein Change | Normal Variant Depth | Normal Total Depth | Normal Variant Frequency | Tumor Variant Depth | Tumor Total Depth | Tumor Variant Frequency |
| 35 | 2 | 238730415 | A | C | RBM44 | p.N718T | 2 | 186 | 1 | 18 | 79 | 23 |
| 35 | 3 | 49412973 | C | A | RHOA | p.G17V | 0 | 127 | 0 | 20 | 82 | 24 |
| 35 | 6 | 146264298 | G | A | SHPRH | p.S740L | 0 | 99 | 0 | 10 | 53 | 19 |
| 35 | 2 | 103310931 | A | C | SLC9A2 | p.Q495P | 0 | 54 | 0 | 8 | 33 | 24 |
| 35 | 10 | 45430560 | T | A | TMEM72 | p.L269H | 0 | 81 | 0 | 13 | 36 | 36 |
| 35 | 9 | 77370317 | C | T | TRPM6 | p.E1620K | 0 | 152 | 0 | 8 | 40 | 20 |
| 35 | 22 | 28503210 | C | T | TTC28 | p.D875N | 0 | 186 | 0 | 17 | 89 | 19 |
| 35 | 21 | 38529196 | T | G | TTC3 | p.F994V | 0 | 54 | 0 | 9 | 53 | 17 |
| 35 | 6 | 139563957 | T | A | TXLNB | p.E587D | 0 | 105 | 0 | 9 | 54 | 17 |
| 35 | 6 | 83667129 | G | T | UBE2CBP | p.L351I | 0 | 65 | 0 | 7 | 36 | 19 |
| 35 | 3 | 33454225 | A | C | UBP1 | p.L146R | 0 | 212 | 0 | 26 | 153 | 17 |
| 35 | 1 | 55595233 | T | G | USP24 | p.K1024N | 0 | 75 | 0 | 16 | 97 | 16 |
| 35 | 18 | 56587557 | T | G | ZNF532 | p.L680V | 0 | 114 | 0 | 10 | 59 | 17 |

TABLE 4

Recurrent variants identified by exome sequencing

| Sample | Chromosome | Position | Reference Sequence | Variant Sequence | Gene | Predicted Protein Change | Normal Variant Depth | Normal Total Depth | Normal Variant Frequency | Tumor Variant Depth | Tumor Total Depth | Tumor Variant Frequency |
|---|---|---|---|---|---|---|---|---|---|---|---|---|
| 1 | 5 | 13883156 | G | A | DNAH5 | p.R1011W | 0 | 44 | 0 | 11 | 49 | 22 |
| 2 | 5 | 13845086 | G | A | DNAH5 | p.R1711X | 0 | 52 | 0 | 20 | 55 | 36 |
| 33 | 5 | 13841805 | G | C | DNAH5 | p.A1827G | 0 | 39 | 0 | 23 | 48 | 48 |
| 1 | 12 | 86377381 | G | A | MGAT4C | p.T72I | 0 | 83 | 0 | 25 | 74 | 34 |
| 2 | 12 | 86373596 | C | T | MGAT4C | p.R303H | 0 | 83 | 0 | 24 | 57 | 42 |
| 1 | 9 | 8518099 | G | A | PTPRD | p.S431L | 0 | 67 | 0 | 23 | 69 | 33 |
| 2 | 9 | 8389314 | G | A | PTPRD | p.T1435I | 0 | 112 | 0 | 39 | 92 | 42 |
| 11 | 3 | 49412973 | C | A | RHOA | p.G17V | 0 | 104 | 0 | 19 | 103 | 18 |
| 31 | 3 | 49412973 | C | A | RHOA | p.G17V | 1 | 110 | 1 | 17 | 90 | 19 |
| 35 | 3 | 49412973 | C | A | RHOA | p.G17V | 0 | 127 | 0 | 20 | 82 | 24 |
| 4 | 15 | 33893746 | G | A | RYR3 | p.V639I | 0 | 126 | 0 | 12 | 75 | 16 |
| 29 | 15 | 34103203 | G | A | RYR3 | p.E3408K | 0 | 52 | 0 | 16 | 53 | 30 |
| 2 | 3 | 47058660 | T | G | SETD2 | p.T2540P | 0 | 62 | 0 | 16 | 57 | 28 |
| 2 | 3 | 47125211 | T | — | SETD2 | p.K2020fs | 0 | 92 | 0 | 36 | 90 | 40 |
| 5 | 3 | 47163958 | T | A | SETD2 | p.N723I | 0 | 169 | 0 | 44 | 180 | 24 |
| 11 | 10 | 123970755 | A | G | TACC2 | p.D418G | 0 | 48 | 0 | 14 | 71 | 20 |
| 29 | 10 | 123970184 | A | G | TACC2 | p.T228A | 0 | 55 | 0 | 35 | 103 | 34 |
| 26 | 4 | 106156729 | C | T | TET2 | p.R544X | 0 | 68 | 0 | 16 | 99 | 16 |
| 28 | 4 | 106157329 | C | T | TET2 | p.Q744X | 0 | 58 | 0 | 12 | 63 | 19 |
| 28 | 4 | 106196920.5 | — | A | TET2 | p.Y1751fs | 1 | 95 | 1 | 12 | 64 | 19 |
| 29 | 4 | 106193931 | C | T | TET2 | p.R1465X | 0 | 28 | 0 | 10 | 22 | 45 |
| 29 | 4 | 106197360 | C | T | TET2 | p.S1898F | 0 | 55 | 0 | 27 | 60 | 45 |

TABLE 5

Predicted somatic variants identified in PTCL by targeted deep sequencing
Percentage of variant reads are indicated

| Mutations | BCN2 | BCN2b | BCN3 | BCN4b | BCN5b | BCN6b | BCN7b | BCN9b | BCN11b | BCN12 | BCN13b | BCN14b | BCN15 | BCN15b | BCN16b | BCN17b | BCN19 | BCN19b |
|---|---|---|---|---|---|---|---|---|---|---|---|---|---|---|---|---|---|---|
| ATM p.D2959N | | | | | | | | | | | | | | | | | | |
| ATM p.T2333K | | | | | | | | | | | | | | | | | | |
| DNMT3A p.G453fs | | | | | | | | | | | | | | | | | | |
| DNMT3A p.L459P | | | | | | 56 | | | | | | | | | | | | |
| DNMT3A p.L461Q | | | | | | | | | | | | | | | | | | |
| DNMT3A p.N649D | | | | | | | | | | | | | | | | | | |
| DNMT3A p.N690D | | | | | | | | | | | | | | | | | | |
| DNMT3A p.P682fs | | | | | | | | | | | | | | | | | | |
| DNMT3A p.R547C | | | | | | | | | | | | | | | | | 17 | |
| DNMT3A p.R693C | | | | | | | | | | | | | | | | | | |
| DNMT3A p.R693H | | | | | | | | | | | | | | | | | | |
| DNMT3A p.V433fs | | | | | | | | | | | | | | | | | | |
| DNMT3A p.V501D | | | | | | | | | | | | | | | | | | |
| DNMT3A p.W671X | | | | | | | | | | | | | | | | | | |
| FYN p.L174R | | | | | | | | | | | | | | | | | | |
| FYN p.R176C | | | | | | 39 | | 33 | | | | | | | | | | |
| IDH2 p.R172K | | | | | | | | | | | | | | | | | | |
| IDH2 p.R172S | | | | | | | | | | | | | | | | | | |
| RHOA T19I | | | | | | | | | | | | | | | | | | |
| RHOA p.C16R | | | | | | | | | | | | | | | | | | |
| RHOA p.D120Y | | | | | | | | | | | | 11 | | | | | | |
| RHOA p.G17E | | | | | | | | | | | | | | | | | | |
| RHOA p.G17V | | 34 | 8 | | | | | | 6 | | | | | 9 | | | | |
| TET2 p.1166_splice | | | | | | | | | | | | | | | | | | |
| TET2 p.1513_splice | | | | | | | | | | | | | | | | | | |
| TET2 p.A1443fs | | | | | | | | | | | | | | | | | | |
| TET2 p.A1562fs | | | | | | | | | | | | | | | | | | |
| TET2 p.C1221Y | | | | | | | | | | | | | | | 9 | | | |
| TET2 p.C1273F | | | | | | | | | | | | | | | | | | |
| TET2 p.C1378F | | | | | | | | | | | | | | | | | | |
| TET2 p.D390fs | | | | | | | | | | | | | 31 | | | | | |
| TET2 p.E1141fs | | 32 | | | | | | | | | | | | | | | | |
| TET2 p.E1162fs | | | | | | | | | | | | | | | | | | |
| TET2 p.E1318fs | | | | | | | | | | | | | | | | | | |
| TET2 p.E1437fs | | | | | | | | | | | | | | | | | | |
| TET2 p.E1490fs | | | | | | | | | | | | | | | | | | |
| TET2 p.E452X | | | | | | | | | | | | | | | | | | |
| TET2 p.E807fs | | | | | | | | | | | | | | | | | | |
| TET2 p.G1860fs | | | | | 21 | | | | | | | | | | | | | |
| TET2 p.H1380L | | | | | | | | | | | | | | | | | | |
| TET2 p.H1551fs | | | | | | | | | | | | | | | | | | |
| TET2 p.H1881R | | | | | | | | | | | | | | | | | | |
| TET2 p.H762fs | | | | | | | | | | | | 15 | | | | | | |
| TET2 p.1518fs | | | | | | | | | | | | | | | | | | |
| TET2 p.L1340R | | | | | | | | | | | | | | | | | | |
| TET2 p.L532X | | | | | | | | | | | | | | | | | | |

TABLE 5-continued

Predicted somatic variants identified in PTCL by targeted deep sequencing
Percentage of variant reads are indicated

| Mutations | BCN20b | BCN22b | BCN25 | BCN25b | BCN27b | BCN29b | BCN30b | BCN32b | BCN34b | CU1 | CU2 | CU4 | CU7 | CU8 | CU11 | CU16 | CU20 | CU22 |
|---|---|---|---|---|---|---|---|---|---|---|---|---|---|---|---|---|---|---|
| TET2 p.L957fs | | | | | | | | | | | | | | | 16 | 15 | | |
| TET2 p.M1570fs | | | | | | | | | | | | | | | | | | |
| TET2 p.N1774fs | | | | | | | | | | | | | | | 15 | 19 | | |
| TET2 p.P1092fs | | | | | | | 19 | | | | | | | | | | | |
| TET2 p.Q1030X | | | | | | | 22 | | | | | | | | | | | |
| TET2 p.Q417X | | | | | | | | | | | | | | | | | | |
| TET2 p.Q674X | | | | | | | | | | | | | | | | | | |
| TET2 p.Q731X | | | | | | | | | | | | | | | | | | |
| TET2 p.Q746X | | | | | | | | | | | | | | | | | | |
| TET2 p.Q821fs | | | | | | | | | | | | | | | | | | |
| TET2 p.Q916X | | 26 | | | | | | | | | | | | | | | | |
| TET2 p.R1404X | | | | | | | | | | | 22 | | | | | | | |
| TET2 p.R1465X | | | | | | | | | | | | 12 | | | | | | |
| TET2 p.R1516X | | | | | | | | | | | | | | | | | 36 | |
| TET2 p.R550X | | | | | | | | | | | | | | | | | | |
| TET2 p.S1688fs | | | | | 23 | | | | | | | | | | | | | |
| TET2 p.S1870L | | | | | | | | | | | | | | | | | | |
| TET2 p.T1078fs | | | | | | | | | | | | | | | | | | |
| TET2 p.V1054fs | | | | | | | | | | | | | | | | | | |
| TET2 p.V160fs | | | | | | | | | | | | | | | | | | |
| TET2 p.V841fs | | | | | | | | | | | | | | | | | | |
| TET2 p.V927fs | | | | | | | | | | | | | | | | | | |
| TET2 p.Y1255fs | | | | | | 44 | | | | | | | | | | | | |
| TET3 p.G1360S | | | | | | | | | | | | | | | | | | |
| B2M p.E56X | | | | | | | | | | | | | | | | | | |
| B2M p.M1R | | | | | | | | | | | | | | | | | | |
| CD58 p.F43fs | | | | | | | | | | | | | | | | | | |
| CD58 p.G210C | | | | | | | | | | | | | | | | | | 36 |
| CD58 p.G210S | | | | | | | | | | | | | | | | | | |
| CD58 p.K60fs | | | | | | | | | | | | | | | | | | |
| CD58 p.R152X | | | | | | | | 22 | | | | | | | | | | |
| CD58 p.S107X | | | | | | | | | | | | | | | | | | |
| CDKN2A p.E69X | 53 | | | | | | | | | | | | | | | | | |
| PRKD2 p.R147W | | | | | | | 16 | | | | | | | | | | | |
| RHOT2 p.442_splice | | | | 35 | | | | | | | | | | | | | | |
| SMARCAL1 p.T417M | | | | | | | | | | | | | | | | | | |
| ATM p.D2959N | | | | | | | | | | 28 | | | | | | | | |
| ATM p.T2333K | | | | | | | | | | | | | | | | | | |
| DNMT3A p.G453fs | | | | | | | 39 | | | | | | | | | | | |
| DNMT3A p.L459P | | | | | | | | | | | | | | | | | | |
| DNMT3A p.L461Q | | | | | | | | | | | | | | | | | | |
| DNMT3A p.N649D | | | | | | | | | | | | | | | | | | |
| DNMT3A p.N690D | | | | | | | | | | | | | | | | | | |
| DNMT3A p.P682fs | 21 | | | | | | | | | | | | | | | | | |
| DNMT3A p.R547C | | | | | | | | | | | | | | | | | | |
| DNMT3A p.R693C | | | | | | | | | | | | | | | | | | |
| DNMT3A p.R693H | | | | | | | | 33 | | | | | | | | | | |

TABLE 5-continued

Predicted somatic variants identified in PTCL by targeted deep sequencing
Percentage of variant reads are indicated

| | | | | | | | | | | | | | |
|---|---|---|---|---|---|---|---|---|---|---|---|---|---|
| DNMT3A p.V433fs | | | | | | | | | | | 29 | | |
| DNMT3A p.V501D | | | | | | | | | | | | | |
| DNMT3A p.W671X | | | | | | 35 | | | | | | | |
| FYN p.L174R | | | | 14 | | | | | | | | | |
| FYN p.R176C | | | | | | | | | | | | | |
| IDH2 p.R172K | | | | | | | | 16 | | | | | |
| IDH2 p.R172S | | | | | | | | | | | | | |
| RHOA T19I | | | | | | | | | | | | | |
| RHOA p.C16R | | | | | | | | | | | | | 19 |
| RHOA p.D120Y | | | | | | | | | | | | | |
| RHOA p.G17E | | | | | | | | | | | | | |
| RHOA p.G17V | | 26 | | 9 | 21 | 58 | 28 | 11 | 6 | 7 | 20 | | |
| TET2 p.1166_splice | | | | | | | | | | | | | |
| TET2 p.1513_splice | | | | | 28 | | | | | | | | |
| TET2 p.A1443fs | | | 39 | | | | | | | | | | |
| TET2 p.A1562fs | 17 | | | | | | | | | | | | |
| TET2 p.C1221Y | | | | | | | | | | | | | |
| TET2 p.C1273F | | | | | | | | | | | | | |
| TET2 p.C1378F | | | | | | | | | | | | | |
| TET2 p.D390fs | | | | | | | | | | | | | |
| TET2 p.E1141fs | | | | | | | | | | | | | |
| TET2 p.E1162fs | | | | | | | | | | | 31 | | |
| TET2 p.E1318fs | | | | 45 | | | | | | | | | |
| TET2 p.E1437fs | | | | | | | | | | | | | |
| TET2 p.E1490fs | | | | | | | | | | | | | |
| TET2 p.E452X | | | | 36 | | | | | | | | | |
| TET2 p.E807fs | | | | | | | | | | | | | |
| TET2 p.G1860fs | | | | | | | | | | | | | |
| TET2 p.H1380L | | | | | | | | | | | 29 | | |
| TET2 p.H1551fs | | | | | | | | | | 33 | | | |
| TET2 p.H1881R | | | | | | | | | | | | | |
| TET2 p.H762fs | | | | | | | | | | | | | |
| TET2 p.1518fs | | | | | | | | | | | | | |
| TET2 p.L1340R | | | | | | | | | | | | | |
| TET2 p.L532X | | | | | | | | | | | | 26 | |
| TET2 p.L957fs | | | | | | | | | | | | | |
| TET2 p.M1570fs | | | | | | | | | | | | | |
| TET2 p.N1774fs | | | | | | | | | | | | | |
| TET2 p.P1092fs | | | | | | | | | | | | | |
| TET2 p.Q1030X | | | | | | | | | | | | | |
| TET2 p.Q417X | | | | | | | | | 31 | | | | |
| TET2 p.Q674X | | | | | | | 48 | | | | | | |
| TET2 p.Q731X | | | | | | | | | | | | | |
| TET2 p.Q746X | | | | | | | | | | 28 | | | |
| TET2 p.Q821fs | | | | | | | | | | | | | |
| TET2 p.Q916X | | | | | | | | | | | | | |
| TET2 p.R1404X | | | | | | | | | | | | | |
| TET2 p.R1465X | | | | | | | | | | | | | |
| TET2 p.R1516X | | | | | | | | | | | | | |
| TET2 p.R550X | | | | | | | | | | | | | |

TABLE 5-continued

Predicted somatic variants identified in PTCL by targeted deep sequencing
Percentage of variant reads are indicated

| Mutations | CU24 | CU31 | CU42 | CU44 | CU45 | CU48 | CU49 | CU50 | SDR1 | SDR4 | SDR6 | SDR7 | SDR9 | SDR15 | SDR17 | SDR39 | SDR45 | SDR47 |
|---|---|---|---|---|---|---|---|---|---|---|---|---|---|---|---|---|---|---|
| TET2 p.S1688fs | | | | | | | | | | | | | | | | | | |
| TET2 p.S1870L | | | | | | | | | | | | | | | | | | |
| TET2 p.T1078fs | | | | | | | | | | | | | | | | | | |
| TET2 p.V1054fs | | | | | | 10 | | | | | | | | | | | | |
| TET2 p.V160fs | | | | | | | | | | | | | | | | | | |
| TET2 p.V841fs | | | | | | | | | | | | | | | | | | |
| TET2 p.V927fs | | | | | | | | | | | | | | | | | | |
| TET2 p.Y1255fs | | | | | | | | | | | | | | | | | | |
| TET3 p.G1360S | | | | | | | | | | | | | | | | | | |
| B2M p.E56X | | | | | | | | | | | | | | | | | | |
| B2M p.M1R | | | | | | | | | | | | | | | | | | |
| CD58 p.F43fs | | | | | | | | | | | | | | | | | | |
| CD58 p.G210C | | | | | | | | | | | | | | | | | | |
| CD58 p.G210S | | | | | | | | | | | | | | | | | | |
| CD58 p.K60fs | | | | | | | | | | | | | | | | | | |
| CD58 p.R152X | | | | | | | | | | | | | | | | | | |
| CD58 p.S107X | | | | | | | | | | | | | | | | | | |
| CDKN2A p.E69X | | | | | | | | | | | | | | | | | | |
| PRKD2 p.R147W | | | | | | | | | | | | | | | | | | |
| RHOT2 p.442_splice | | | | | | | | | | | | | | | | | | |
| SMARCAL1 p.T417M | | | | | | | | | | | | | | | | | | |

| Mutations | CU24 | CU31 | CU42 | CU44 | CU45 | CU48 | CU49 | CU50 | SDR1 | SDR4 | SDR6 | SDR7 | SDR9 | SDR15 | SDR17 | SDR39 | SDR45 | SDR47 |
|---|---|---|---|---|---|---|---|---|---|---|---|---|---|---|---|---|---|---|
| ATM p.D2959N | | | | | | | | | | | | | | | | | | |
| ATM p.T2333K | 25 | | | | | | | | | | | | | | | | | |
| DNMT3A p.G453fs | | | | | | | | | | | | | | | | | | |
| DNMT3A p.L459P | | | | | | | | | | | | | | | | | | |
| DNMT3A p.L461Q | | 29 | | | | | | | | | | | | | | | | |
| DNMT3A p.N649D | | | | | | | | | | | | | | | | | 35 | |
| DNMT3A p.N690D | | | | 39 | | | | | | | | | | | | | | |
| DNMT3A p.P682fs | | | | | | | | | | | | | | | | | | |
| DNMT3A p.R547C | | | | | | | | | | | | | | | | | | |
| DNMT3A p.R693C | | | | | | | | | | | 34 | | | | | | | |
| DNMT3A p.R693H | | | | | | | | | | | | | | | | | | |
| DNMT3A p.V433fs | | | | | | | | | | | | | | | | | | |
| DNMT3A p.V501D | | | | | | | | | | | | | | | | 24 | | |
| DNMT3A p.W671X | | | | | | | | | | | | | | | | | | |
| FYN p.L174R | | | | | | | | | | | | | | | | | | |
| FYN p.R176C | | | | | | | | | | | | | | | | | | |
| IDH2 p.R172K | | | | | | | | | | | | | | | | | | 8 |
| IDH2 p.R172S | | | | | | | | | | | 7 | 6 | | | | | | |
| RHOA T19I | 7 | | | | | | | | | | | | | | | | | |
| RHOA p.C16R | | | | | | | | | | | | | | | | | | |
| RHOA p.D120Y | | | | | | | | | | | | | | | | | | |
| RHOA p.G17E | | | | | | | | | | | | | | | | | | |
| RHOA p.G17V | | | | | | | | | | | 7 | | | 8 | | 10 | | |
| TET2 p.1166_splice | | | | | | | | | | | | | 49 | | | | | |
| TET2 p.1513_splice | | | | | | | | | | | | | | | | | | |
| TET2 p.A1443fs | | | | | | | | | | | | | | | | | | |

TABLE 5-continued

Predicted somatic variants identified in PTCL by targeted deep sequencing
Percentage of variant reads are indicated

| | | | | | | | | | | | | |
|---|---|---|---|---|---|---|---|---|---|---|---|---|
| TET2 p.A1562fs | | | | | | | | | | | | |
| TET2 p.C1221Y | | | | | | | | | | | | |
| TET2 p.C1273F | | | | | | | | | 18 | | | |
| TET2 p.C1378F | | | | | | 27 | | | | | | |
| TET2 p.D390fs | | | | | | | | | | | | |
| TET2 p.E1141fs | | | | | | | | | | | | |
| TET2 p.E1162fs | | | | | | | | | | | | |
| TET2 p.E1318fs | | | | | | | | | | | | |
| TET2 p.E1437fs | | | | | | | | 16 | | | | |
| TET2 p.E1490fs | | | | | | | | | | | | |
| TET2 p.E452X | | | | | | | | | | | | |
| TET2 p.E807fs | | 38 | | | | | | | | | | |
| TET2 p.G1860fs | | | | | | | | | | | | |
| TET2 p.H1380L | | | | | | | | | | | | |
| TET2 p.H1551fs | | | | | | | | | | | | |
| TET2 p.H1881R | | | 37 | | | | | | | | | |
| TET2 p.H762fs | | | | | | | | | | | | |
| TET2 p.1518fs | | | | 30 | | | | | | | | |
| TET2 p.L1340R | | | | | | | | 33 | | | | |
| TET2 p.L532X | | | | | | | | | | | | |
| TET2 p.L957fs | | | | | | | | | | | | |
| TET2 p.M1570fs | | | | | | | | | | | | |
| TET2 p.N1774fs | | | | | | | | | | | | |
| TET2 p.P1092fs | | | | | | | | | | | | |
| TET2 p.Q1030X | | | | | | | | | | | | |
| TET2 p.Q417X | | | | | | | | | | | | |
| TET2 p.Q674X | | | | | | | | | | | | |
| TET2 p.Q731X | | | | | | | | | | 24 | | |
| TET2 p.Q746X | | | | | | | | | | | | |
| TET2 p.Q821fs | | | | | | | | | | | | |
| TET2 p.Q916X | | | | | | | | | | | 40 | |
| TET2 p.R1404X | | | | | | | | | | | | |
| TET2 p.R1465X | | | | | | | | | | | | |
| TET2 p.R1516X | | | | | | | | | | | | |
| TET2 p.R550X | | | | | | | | | | | | 11 |
| TET2 p.S1688fs | | | | | | | | | | | | |
| TET2 p.S1870L | | | | | | | 14 | | | | | |
| TET2 p.T1078fs | 20 | | | | | | | | | | | |
| TET2 p.V1054fs | | | | | | | | | | | | |
| TET2 p.V160fs | | | | | | 14 | | | | | | |
| TET2 p.V841fs | | | | | | | | | | | | |
| TET2 p.V927fs | | | | | | | | | 23 | | | |
| TET2 p.Y1255fs | | | | | | | | | | | | |
| TET3 p.G1360S | | | | | 60 | | | | | | | |
| B2M p.E56X | | | | | | | | | 27 | | | |
| B2M p.M1R | | | | | | | | | 19 | | | |
| CD58 p.F43fs | | | | 34 | | | | | | | | |
| CD58 p.G210C | | | | | | | | | | | | |
| CD58 p.G210S | | | | | | | | | | | | |
| CD58 p.K60fs | | | | | | | | | | | | |

TABLE 5-continued

Predicted somatic variants identified in PTCL by targeted deep sequencing
Percentage of variant reads are indicated

| Mutations | SDR50 | SDR51 | SDR52 | SDR53 | d3389093 | s2353922 | s614558 | s6TF | s7TF | s12TF |
|---|---|---|---|---|---|---|---|---|---|---|
| CD58 p.R152X | | | | | | | | | | |
| CD58 p.S107X | | | | | | | | | | |
| CDKN2A p.E69X | | | | | | | | | | |
| PRKD2 p.R147W | | | | | | | | | | |
| RHOT2 p.442_splice | | | | | | | | | | |
| SMARCAL1 p.T417M | | | 30 | | | | | | | |
| ATM p.D2959N | | | | | | | | | | |
| ATM p.T2333K | | | | | | | | | | |
| DNMT3A p.G453fs | | | | | | | | | | |
| DNMT3A p.L459P | | | | | | | | | | |
| DNMT3A p.L461Q | | | | | | | | | | |
| DNMT3A p.N649D | | | | | | | | | | |
| DNMT3A p.N690D | | | | | | | | | | |
| DNMT3A p.P682fs | | | | | | | | | | |
| DNMT3A p.R547C | | | | | | | | | | |
| DNMT3A p.R693C | | | | | | | | | | |
| DNMT3A p.R693H | 14 | | | | | | | | | |
| DNMT3A p.V433fs | | | | | | | | | | |
| DNMT3A p.V501D | | | | | | | | | | |
| DNMT3A p.W671X | | | | | | | | | | |
| FYN p.L174R | | | | | | | | | | |
| FYN p.R176C | | | | | | | | | | |
| IDH2 p.R172K | | | | | | | | | | |
| IDH2 p.R172S | | | | | | | | | | |
| RHOA T19I | | | | | | | | | | |
| RHOA p.C16R | | | | | | | | | | |
| RHOA p.D120Y | | | | | | | | | | |
| RHOA p.G17E | | | | | | | 16 | | | |
| RHOA p.G17V | 6 | 12 | | | | | | 13 | | |
| TET2 p.1166_splice | | | | | | | | | | |
| TET2 p.1513_splice | | | | | | | | | | |
| TET2 p.A1443fs | | | | | | | | | | |
| TET2 p.A1562fs | | | | | | | | | | |
| TET2 p.C1221Y | | | | | | | | | | |
| TET2 p.C1273F | | | | | | | | | | |
| TET2 p.C1378F | | | | | | | | | | |
| TET2 p.D390fs | | | | | | | | | | |
| TET2 p.E1141fs | | | | | | | | | | |
| TET2 p.E1162fs | | | | | | | | | | |
| TET2 p.E1318fs | | | | | | | | | | |
| TET2 p.E1437fs | 12 | | | | | | | | | |
| TET2 p.E1490fs | | | | | | | | 28 | | |
| TET2 p.E452X | | | | | | | | | | |
| TET2 p.E807fs | | | | | | | | | | |
| TET2 p.G1860fs | | | | | | | | | | |
| TET2 p.H1380L | | | | | | | | | | |
| TET2 p.H1551fs | | | | | | | | | | |

TABLE 5-continued

Predicted somatic variants identified in PTCL by targeted deep sequencing
Percentage of variant reads are indicated

| | | | | | |
|---|---|---|---|---|---|
| TET2 p.H1881R | | | | | |
| TET2 p.H762fs | | | | | |
| TET2 p.1518fs | | | | | |
| TET2 p.L1340R | | | | | |
| TET2 p.L532X | | | | | |
| TET2 p.L957fs | | | | | |
| TET2 p.M1570fs | | | | 13 | |
| TET2 p.N1774fs | | | | | |
| TET2 p.P1092fs | | | | | |
| TET2 p.Q1030X | | | | | |
| TET2 p.Q417X | | | | | |
| TET2 p.Q674X | | | | | |
| TET2 p.Q731X | | | | | |
| TET2 p.Q746X | | | | | |
| TET2 p.Q821fs | | 37 | | | |
| TET2 p.Q916X | 14 | | | | |
| TET2 p.R1404X | | | | | |
| TET2 p.R1465X | | | | | |
| TET2 p.R1516X | | | | | |
| TET2 p.R550X | | | | | |
| TET2 p.S1688fs | | | | | |
| TET2 p.S1870L | | | | | |
| TET2 p.T1078fs | | | | | |
| TET2 p.V1054fs | | | | | |
| TET2 p.V160fs | | | | | |
| TET2 p.V841fs | | 33 | | | |
| TET2 p.V927fs | | | | | |
| TET2 p.Y1255fs | | | | | |
| TET3 p.G1360S | | | | | |
| B2M p.E56X | | | | | |
| B2M p.M1R | | | | | |
| CD58 p.F43fs | | | | | |
| CD58 p.G210C | | | | | |
| CD58 p.G210S | | | | | 28 |
| CD58 p.K60fs | | | 22 | | |
| CD58 p.R152X | | | | | |
| CD58 p.S107X | | | 18 | | |
| CDKN2A p.E69X | | | | | |
| PRKD2 p.R147W | | | | | |
| RHOT2 p.442_splice | | | | | |
| SMARCAL1 p.T417M | | | | | |

TABLE 6

RHOA p. Gly17Val mutation detection results by quantitative allele specific PCR

| Sample | Diagnosis | RHOA G17V allele (%) |
|---|---|---|
| BCN34b | AITL | 79.5 |
| BCN30b | AITL | 61.2 |
| BCN25b | AITL | 59.7 |
| BCN2b | AITL | 56.5 |
| CU1 | AITL | 53.7 |
| SDR36 | PTCL-NOS | 52.7 |
| CU2 | AITL | 43.5 |
| CU8 | AITL | 41.5 |
| 6TF | AITL | 39.4 |
| SDR47 | AITL | 36.1 |
| BCN32b | PTCL-NOS | 35.3 |
| BCN15b | AITL | 17.8 |
| CU3 | AITL | 17.3 |
| SDR39 | AITL | 16.9 |
| SDR50 | PTCL-NOS | 16.9 |
| CU4 | AITL | 16.1 |
| SDR51 | AITL | 14 |
| SDR6 | AITL | 13.9 |
| BCN11b | AITL | 13.1 |
| BCN13b | PTCL-NOS | 12.8 |
| BCN15 | PTCL-NOS | 12.8 |
| SDR15 | AITL | 11.4 |
| CU7 | AITL | 11.1 |
| SDR4 | PTCL-NOS | 9.42 |
| SDR7 | AITL | 9.3 |
| CU6 | AITL | 8.56 |
| SDR45 | AITL | 7.7 |
| BCN3 | PTCL-NOS | 6.22 |
| BCN29b | PTCL-NOS | 1.27 |
| BCN17b | AITL | 1.25 |
| CU5 | AITL | 0 |
| s4312442 | AITL | 0 |
| 7TF | AITL | 0 |
| BCN14b | AITL | 0 |
| BCN19 | AITL | 0 |
| BCN27b | AITL | 0 |
| BCN5b | AITL | 0 |
| BCN7b | AITL | 0 |
| CU10 | AITL | 0 |
| SDR1 | AITL | 0 |
| SDR52 | AITL | 0 |
| SDR53 | AITL | 0 |
| CU11 | AITL | 0 |
| BCN26b | ALCL | 0 |
| BCN31b | ALCL | 0 |
| SDR10 | ALCL | 0 |
| SDR54 | ALCL | 0 |
| BCN12b | ALCL ALK− | 0 |
| BCN18b | ALCL ALK− | 0 |
| BCN20b | ALCL ALK− | 0 |
| BCN30 | ALCL ALK− | 0 |
| BCN36b | ALCL ALK− | 0 |
| BCN8b | ALCL ALK− | 0 |
| CU13 | ALCL ALK− | 0 |
| CU14 | ALCL ALK− | 0 |
| CU15 | ALCL ALK− | 0 |
| SDR48 | ALCL ALK− | 0 |
| CU16 | ALCL ALK− | 0 |
| CU17 | ALCL ALK− | 0 |
| 12TF | ALCL ALK+ | 0 |
| 8TF | ALCL ALK+ | 0 |
| BCN22b | ALCL ALK+ | 0 |
| BCN23b | ALCL ALK+ | 0 |
| BCN24b | ALCL ALK+ | 0 |
| BCN33 | ALCL ALK+ | 0 |
| BCN33b | ALCL ALK+ | 0 |
| BCN3b | ALCL ALK+ | 0 |
| CU18 | ALCL ALK+ | 0 |
| CU19 | ALCL ALK+ | 0 |
| CU20 | ALCL ALK+ | 0 |
| CU22 | ALCL ALK+ | 0 |
| CU23 | ALCL ALK+ | 0 |
| CU24 | ATLL | 0 |
| 0U25 | ATLL | 0 |

TABLE 6-continued

RHOA p. Gly17Val mutation detection results by quantitative allele specific PCR

| Sample | Diagnosis | RHOA G17V allele (%) |
|---|---|---|
| CU26 | ATLL | 0 |
| CU27 | ATLL | 0 |
| CU28 | ATLL | 0 |
| 2TF | CTCL | 0 |
| CU53 | CTCL | 0 |
| CU30 | CTCL | 0 |
| CU31 | EATL | 0 |
| CU32 | EATL | 0 |
| CU33 | EATL | 0 |
| CU35 | HSTCL | 0 |
| CU36 | HSTCL | 0 |
| CU37 | HSTCL | 0 |
| CU34 | Hydroa Vacciniforme like | 0 |
| BCN4b | MF/Sézary syndrome | 0 |
| BCN10b | PTCL-NOS | 0 |
| BCN12 | PTCL-NOS | 0 |
| BCN14 | PTCL-NOS | 0 |
| BCN16b | PTCL-NOS | 0 |
| BCN17 | PTCL-NOS | 0 |
| BCN19b | PTCL-NOS | 0 |
| BCN1b | PTCL-NOS | 0 |
| BCN2 | PTCL-NOS | 0 |
| BCN24 | PTCL-NOS | 0 |
| BCN28b | PTCL-NOS | 0 |
| BCN35b | PTCL-NOS | 0 |
| BCN6b | PTCL-NOS | 0 |
| BCN9b | PTCL-NOS | 0 |
| CU12 | PTCL-NOS | 0 |
| CU42 | PTCL-NOS | 0 |
| CU43 | PTCL-NOS | 0 |
| CU44 | PTCL-NOS | 0 |
| CU45 | PTCL-NOS | 0 |
| CU46 | PTCL-NOS | 0 |
| CU47 | PTCL-NOS | 0 |
| s2353922 | PTCL-NOS | 0 |
| s3389093 | PTCL-NOS | 0 |
| SDR11 | PTCL-NOS | 0 |
| SDR16 | PTCL-NOS | 0 |
| SDR17 | PTCL-NOS | 0 |
| SDR30 | PTCL-NOS | 0 |
| SDR40 | PTCL-NOS | 0 |
| SDR49 | PTCL-NOS | 0 |
| SDR5 | PTCL-NOS | 0 |
| SDR8 | PTCL-NOS | 0 |
| SDR9 | PTCL-NOS | 0 |
| BCN25 | PTCL-NOS | 0 |
| CU48 | PTCL-NOS | 0 |
| CU49 | PTCL-NOS | 0 |
| CU50 | PTCL-NOS | 0 |
| s614558 | PTCL-NOS | 0 |
| CU51 | TLGL | 0 |

Cutoff for RHOA p.Gly17Val positivity = 1%

TABLE 7

RNAseq depth and coverage results

| Sample | Number of Reads | Number of Reads Mapped | Percentage of Reads Mapped |
|---|---|---|---|
| BCN1 | 57309822 | 48282519 | 84.25 |
| BCN10 | 66026002 | 55502342 | 84.06 |
| BCN11 | 57564914 | 47204108 | 82 |
| BCN12 | 56167286 | 25287448 | 45.02 |
| BCN13 | 66486354 | 47256299 | 71.08 |
| BCN14 | 69449958 | 48162506 | 69.35 |
| BCN15 | 62075032 | 47638393 | 76.74 |
| BCN16 | 64558528 | 47818509 | 74.07 |
| BCN17 | 68193452 | 54864720 | 80.45 |
| BCN18 | 57507948 | 44566812 | 77.5 |
| BCN19 | 65198542 | 22716666 | 34.84 |

TABLE 7-continued

RNAseq depth and coverage results

| Sample | Number of Reads | Number of Reads Mapped | Percentage of Reads Mapped |
|---|---|---|---|
| BCN2 | 62813468 | 50209686 | 79.93 |
| BCN20 | 77048836 | 60927623 | 79.08 |
| BCN22 | 66601826 | 55126524 | 82.77 |
| BCN23 | 68804894 | 56774155 | 82.51 |
| BCN24 | 68690036 | 55786185 | 81.21 |
| BCN25 | 66382910 | 52954763 | 79.77 |
| BCN26 | 68191502 | 51159409 | 75.02 |
| BCN27 | 74695958 | 62456657 | 83.61 |
| BCN28 | 60458552 | 46973216 | 77.69 |
| BCN29 | 62913466 | 49359796 | 78.46 |
| BCN3 | 69662696 | 55762051 | 80.05 |
| BCN30 | 67551530 | 47292078 | 70.01 |

TABLE 7-continued

RNAseq depth and coverage results

| Sample | Number of Reads | Number of Reads Mapped | Percentage of Reads Mapped |
|---|---|---|---|
| BCN32 | 66725890 | 48275733 | 72.35 |
| BCN33 | 71678418 | 58970680 | 82.27 |
| BCN34 | 114115570 | 92076843 | 80.69 |
| BCN35 | 83434026 | 66003187 | 79.11 |
| BCN36 | 67845860 | 51049830 | 75.24 |
| BCN4 | 59896710 | 43796501 | 73.12 |
| BCN5 | 62270464 | 35646271 | 57.24 |
| BCN6 | 67030222 | 53609640 | 79.98 |
| BCN7 | 68444974 | 55396409 | 80.94 |
| BCN8 | 61473258 | 48372544 | 78.69 |
| BCN9 | 68521236 | 54431244 | 79.44 |

TABLE 8

Identification of fusion oncogenes via RNAseq analysis

| Sample | Detection Program | Number of Split Reads | 5' fusion gene chromo-some | 5' fusion gene | 5' fusion gene breakpoint | 3' fusion gene chromo-some | 3' fusion gene | 3' fusion gene break-point |
|---|---|---|---|---|---|---|---|---|
| BCN22 | chimerascan | 69 | 5 | NPM1 | 170818802 | 2 | ALK | 29446393 |
| BCN23 | chimerascan | 33 | 5 | NPM1 | 170818802 | 2 | ALK | 29446393 |
| BCN23 | defuse | 50 | 5 | NPM1 | 170818803 | 2 | ALK | 29446394 |
| BCN24 | chimerascan | 54 | 3 | TFG | 100447701 | 2 | ALK | 29446393 |
| BCN24 | defuse | 98 | 3 | TFG | 100447702 | 2 | ALK | 29446394 |
| BCN33 | chimerascan | 220 | 5 | NPM1 | 170818802 | 2 | ALK | 29446393 |
| BCN33 | defuse | 335 | 5 | NPM1 | 170818803 | 2 | ALK | 29446394 |

TABLE 9

Non synonymous candidate variants in PTCL mutated genes identified by RNAseq

| Sample | Chromo-some | Position | Reference sequence | Variant sequence | Variant frequency | Quality | Variant Depth | Total Depth |
|---|---|---|---|---|---|---|---|---|
| BCN26 | 8 | 139833546-139833546 | A | C | 99 | 37.2099 | 81 | 82 |
| BCN35 | X | 48547113-48547126 | GGGGGGTAACAAGG (SEQ ID NO: 8) | | 88 | 19 | 37 | 42 |
| BCN35 | X | 48547102-48547102 | C | — | 82 | 19 | 64 | 78 |
| BCN18 | 1 | 39908447-39908447 | A | G | 75 | 37.0417 | 24 | 32 |
| BCN16 | 1 | 205273239-205273239 | C | T | 66 | 32.4828 | 29 | 44 |
| BCN26 | 2 | 56420575-56420575 | G | T | 64 | 36.4242 | 16.5 | 25 |
| BCN35 | 17 | 29632575-29632575 | G | T | 63 | 37.8519 | 27 | 43 |
| BCN34 | 2 | 32689664-32689664 | C | T | 59 | 34.3 | 50 | 85 |
| BCN23 | 2 | 32770910-32770910 | A | G | 57 | 36.7742 | 62 | 109 |
| BCN18 | 20 | 49518597-49518597 | C | T | 55 | 37.3871 | 31 | 56 |
| BCN11 | 12 | 15822734-15822734 | C | T | 54 | 37.0444 | 20.03 | 37 |

TABLE 9-continued

Non synonymous candidate variants in PTCL mutated genes identified by RNAseq

| | | | | | | | | |
|---|---|---|---|---|---|---|---|---|
| BCN25 | 7 | 2255909-2255909 | T | C | 53 | 34.75 | 8 | 15 |
| BCN2 | 12 | 28605561-28605561 | A | G | 52 | 35.7 | 50 | 96 |
| BCNS | 7 | 107566686-107566686 | G | T | 52 | 37.6159 | 45.3 | 87 |
| BCN16 | 1 | 16255266-16255266 | G | A | 52 | 36.7059 | 34 | 66 |
| BCN17 | 1 | 16255266-16255266 | G | A | 51 | 36.6 | 35 | 69 |
| BCN3 | 3 | 9426346-9426346 | G | — | 51 | 19 | 24 | 47 |
| BCN18 | 10 | 95072946-95072946 | C | T | 50 | 36.9429 | 70 | 140 |
| BCN18 | 7 | 107572640-107572640 | T | A | 49 | 35.502 | 101.6 | 206.3 |
| BCN35 | 15 | 75648955-75648955 | G | A | 49 | 35.3097 | 56.5 | 115.5 |
| BCN8 | 21 | 38497019-38497019 | A | C | 47 | 38 | 7 | 15 |
| BCN18 | 12 | 51121495-51121495 | C | T | 46 | 35.7692 | 13 | 28 |
| BCN13 | 1 | 3431182-3431182 | A | G | 46 | 32.375 | 16 | 35 |
| BCN34 | 3 | 49412973-49412973 | C | A | 46 | 35.6991 | 1253 | 2720 |
| BCN30 | 16 | 722002-722002 | C | A | 46 | 35.4435 | 82.3 | 178.7 |
| BCN34 | 4 | 106196902-106196906 | CAATC | — | 46 | 19 | 8 | 18 |
| BCN34 | 2 | 32688343-32688343 | C | A | 45 | 35.5349 | 43 | 95 |
| BCN13 | 12 | 26780968-26780968 | G | A | 45 | 37 | 13 | 29 |
| BCN26 | 1 | 55603331-55603331 | G | A | 45 | 36.4 | 57.5 | 126 |
| BCN22 | 11 | 108203579-108203579 | T | C | 44 | 38.12 | 25 | 57 |
| BCN11 | 2 | 32641048-32641048 | A | T | 44 | 36.1429 | 7 | 16 |
| BCN10 | 1 | 180053158-180053158 | A | G | 42 | 36.7143 | 14 | 33 |
| BCN5 | 10 | 95168556-95168556 | — | A | 42 | 38.4 | 5 | 12 |
| BCN25 | 17 | 2911416-2911416 | G | A | 42 | 36.3 | 10 | 24 |
| BCN2 | 4 | 106155783-106155783 | A | C | 42 | 31.4 | 5 | 12 |
| BCN6 | 6 | 112025223-112025223 | G | A | 41 | 36.3021 | 134.4 | 326 |
| BCN8 | 1 | 46746986-46746986 | G | A | 41 | 36.6383 | 47 | 115.3 |

TABLE 9-continued

Non synonymous candidate variants in PTCL mutated genes identified by RNAseq

| | | | | | | | | |
|---|---|---|---|---|---|---|---|---|
| BCN14 | 21 | 38568211-38568211 | G | C | 41 | 36.6923 | 13 | 32 |
| BCN13 | 22 | 28503654-28503654 | — | T | 40 | 34.5 | 6 | 15 |
| BCN26 | 18 | 51013323-51013328 | GTCAGT | — | 39 | 19 | 10 | 26 |
| BCN9 | 6 | 112025223-112025223 | G | A | 39 | 36.9291 | 165.1 | 423 |
| BCN27 | 4 | 106193865-106193865 | — | C | 39 | 33 | 12 | 31 |
| BCN30 | 6 | 112025228-112025228 | A | C | 36 | 36.6483 | 72.5 | 200 |
| BCN7 | 1 | 39844193-39844193 | A | C | 36 | 33.8 | 5 | 14 |
| BCN33 | 10 | 95121308-95121308 | C | T | 36 | 34.2 | 5 | 14 |
| BCN36 | 1 | 16257098-16257098 | T | G | 35 | 38.3333 | 18 | 51.5 |
| BCN35 | 18 | 51013323-51013328 | GTCAGT | — | 34 | 19 | 31 | 93 |
| BCN36 | 1 | 16257099-16257099 | C | T | 34 | 35 | 17 | 50.5 |
| BCN4 | 1 | 21106336-21106336 | G | C | 32 | 35.5584 | 38.5 | 119 |
| BCN25 | 4 | 106197248-106197248 | G | A | 32 | 36.1667 | 6 | 19 |
| BCN5 | 4 | 106197245-106197245 | G | — | 32 | 18.8889 | 9 | 28 |
| BCN7 | 1 | 39844191-39844191 | C | G | 31 | 33.75 | 4 | 13 |
| BCN1 | 2 | 217279791-217279791 | A | T | 30 | 35.8 | 10 | 33 |
| BCN23 | 5 | 173370050-173370050 | G | A | 29 | 34.75 | 4 | 14 |
| BCN18 | 19 | 50411776-50411776 | C | T | 29 | 34.3558 | 14.67 | 49 |
| BCN2 | 6 | 159172985-159172985 | G | A | 29 | 34.5385 | 13 | 45 |
| BCN17 | 1 | 205273239-205273239 | C | T | 28 | 35.9 | 10 | 36 |
| BCN8 | 10 | 95126210-95126210 | — | A | 26 | 38.4 | 5 | 19.03 |
| BCN24 | X | 77243750-77243750 | — | A | 25 | 39.4 | 5 | 20 |
| BCN16 | 1 | 3415702-3415702 | C | T | 24 | 35.5 | 4 | 17 |
| BCN25 | 3 | 49412973-49412973 | C | A | 24 | 35.6213 | 338 | 1434 |
| BCN15 | 1 | 39800767-39800767 | — | AA | 23 | 40.6667 | 3 | 13 |
| BCN10 | X | 135080645-135080645 | — | T | 23 | 40 | 3 | 13 |

TABLE 9-continued

Non synonymous candidate variants in PTCL mutated genes identified by RNAseq

| | | | | | | | | |
|---|---|---|---|---|---|---|---|---|
| BCN35 | 19 | 50412219-50412219 | — | CTG | 22 | 34 | 10 | 46 |
| BCN14 | 4 | 106193931-106193931 | C | T | 22 | 35.2 | 5 | 23 |
| BCN17 | 1 | 25785197-25785197 | A | G | 21 | 36.8 | 10 | 48 |
| BCN4 | 1 | 3413665-3413665 | A | T | 20 | 33 | 6 | 30.7 |
| BCN13 | 3 | 78710241-78710241 | — | AA | 20 | 34.6667 | 6 | 30 |
| BCN14 | 19 | 36336917-36336917 | C | G | 79 | 35 | 15 | 19 |
| BCN35 | 18 | 50918083-50918083 | A | C | 73 | 33.4545 | 11 | 15 |
| BCN18 | 7 | 100414857-100414857 | G | A | 70 | 36.3077 | 19.5 | 27 |
| BCN17 | 10 | 95185871-95185871 | T | C | 69 | 35.8889 | 27 | 39 |
| BCN13 | 3 | 78717172-78717172 | G | A | 67 | 37.9444 | 18 | 27 |
| BCN16 | 9 | 131073837-131073837 | G | A | 60 | 35.5152 | 33 | 55 |
| BCN15 | 1 | 39913749-39913749 | A | G | 58 | 36 | 55 | 95 |
| BCN11 | 15 | 75660919-75660919 | C | G | 58 | 36 | 7 | 12 |
| BCN13 | 2 | 153475605-153475605 | C | T | 57 | 34.52 | 25 | 44 |
| BCN27 | 1 | 16256317-16256317 | T | C | 55 | 36.2121 | 33 | 60 |
| BCN16 | 10 | 95185871-95185871 | T | C | 54 | 37.7143 | 7 | 13 |
| BCN13 | 12 | 32908734-32908734 | G | A | 52 | 35.2353 | 17 | 33 |

| Sample | RPKM | Predicted amino acid change | Transcript | Gene | CCDS | CCDS exon |
|---|---|---|---|---|---|---|
| BCN26 | 16.28 | p.F360V | NM_152888 | COL22A1 | CCDS6376.1 | 6 |
| BCN35 | 66 | p.G333fs | NM_000377 | WAS | CCDS14303.1 | 10 |
| BCN35 | 66.1 | p.P329fs | NM_000377 | WAS | CCDS14303.1 | 10 |
| BCN18 | 3.82 | p.N4330S | NM_012090 | MACF1 | CCDS435.1 | 73 |
| BCN16 | 11 | p.G409D | NM_030952 | NUAK2 | CCDS1453.1 | 7 |
| BCN26 | 60.96 | p.E414X | NM_001080433 | CCDC85A | CCDS46290.1 | 2 |
| BCN35 | 9.79 | p.T18K | NM_006495 | EVI28 | CCDS11266.1 | 1 |
| BCN34 | 34.25 | p.P1677S | NM_016252 | BIRC6 | CCDS33175.2 | 25 |
| BCN23 | 13.6 | p.S4265G | NM_016252 | BIRC6 | CCDS33175.2 | 63 |
| BCN18 | 14.21 | p.W53X | NM_015339 | ADNP | CCDS13433.1 | 2 |
| BCN11 | 10.08 | p.R77Q | NM_004447 | EPS8 | CCDS31753.1 | 4 |
| BCN25 | 4.28 | p.K231R | NM_001013836 | MAD1L1 | CCDS43539.1 | 6 |

TABLE 9-continued

Non synonymous candidate variants in PTCL mutated genes identified by RNAseq

| | | | | | | |
|---|---|---|---|---|---|---|
| BCN2 | 12.21 | p.I359V | NM_018318 | CCDC91 | CCDS8716.1 | 10 |
| BCN5 | 14.41 | p.A1669E | NM_002291 | LAM81 | CCDS5750.1 | 31 |
| BCN16 | 14.52 | p.R844Q | NM_015001 | SPEN | CCDS164.1 | 11 |
| BCN17 | 13.14 | p.R844Q | NM_015001 | SPEN | CCDS164.1 | 11 |
| BCN3 | 6.5 | p.G500fs | NM_001114092 | THUMPD3 | CCDS2573.1 | 9 |
| BCN18 | 11.92 | p.R1894H | NM_013451 | MYOF | CCDS41550.1 | 50 |
| BCN18 | 30.48 | p.E1457D | NM_002291 | LAM81 | CCDS5750.1 | 27 |
| BCN35 | 25.81 | p.P910L | NM_006715 | MAN2C1 | CCDS32298.1 | 23 |
| BCN8 | 8.57 | p.N404H | NM_001001894 | TTC3 | CCDS13651.1 | 13 |
| BCN18 | 7.89 | p.P1137L | NM_173602 | DIP28 | CCDS31799.1 | 29 |
| BCN13 | 7.64 | p.V262A | NM_001409 | MEGF6 | CCDS41237.1 | 7 |
| BCN34 | 950.69 | p.G17V | NM_001664 | RHOA | CCDS2795.1 | 1 |
| BCN30 | 44.59 | p.T366N | NM_138769 | RHOT2 | CCDS10417.1 | 13 |
| BCN34 | 5 | p.S1744fs | NM_001127208 | TET2 | CCDS47120.1 | 9 |
| BCN34 | 34.25 | p.A1612E | NM_016252 | BIRC6 | CCDS33175.2 | 24 |
| BCN13 | 9.48 | p.S1021L | NM_002223 | ITPR2 | CCDS41764.1 | 23 |
| BCN26 | 27.91 | p.H860Y | NM_015306 | USP24 | CCDS44154.1 | 25 |
| BCN22 | 12.43 | p.Y2627H | NM_000051 | ATM | CCDS31669.1 | 52 |
| BCN11 | 12.85 | p.I897F | NM_016252 | BIRC6 | CCDS33175.2 | 10 |
| BCN10 | 10.83 | p.T2044A | NM_014810 | CEP350 | CCDS1336.1 | 30 |
| BCN5 | 3.67 | p.P239fs | NM_013451 | MYOF | CCDS41550.1 | 7 |
| BCN25 | 3.67 | p.G491R | NM_001100398 | RAP1GAP2 | CCDS45573.1 | 17 |
| BCN2 | 4.21 | p.K228N | NM_001127208 | TET2 | CCDS47120.1 | 1 |
| BCN6 | 49.27 | p.R176C | NM_002037 | FYN | CCDS5094.1 | 4 |
| BCN8 | 30.67 | p.R523C | NM_006369 | LRRC41 | CCDS533.1 | 5 |
| BCN14 | 8.45 | p.R1818P | NM_001001894 | TTC3 | CCDS13651.1 | 41 |
| BCN13 | 3.07 | p.K727fs | NM_001145418 | TTC28 | CCDS46678.1 | 7 |
| BCN26 | 5 | p.1298_1299del | NM_005215 | DCC | CCDS11952.1 | 26 |
| BCN9 | 53.12 | p.R176C | NM_002037 | FYN | CCDS5094.1 | 4 |
| BCN27 | 4.62 | p.A1443fs | NM_001127208 | TET2 | CCDS47120.1 | 8 |
| BCN30 | 30 | p.L174R | NM_002037 | FYN | CCDS5094.1 | 4 |
| BCN7 | 15.95 | p.K2363T | NM_033044 | MACF1 | CCDS435.1 | 47 |
| BCN33 | 3.52 | p.D946N | NM_013451 | MYOF | CCDS41550.1 | 27 |
| BCN36 | 13.86 | p.S1455A | NM_015001 | SPEN | CCDS164.1 | 11 |
| BCN35 | 18 | p.1298_1299del | NM_005215 | DCC | CCDS11952.1 | 26 |
| BCN36 | 13.86 | p.S1455F | NM_015001 | SPEN | CCDS164.1 | 11 |
| BCN4 | 55.25 | p.S55R | NM_016287 | HP18P3 | CCDS30621.1 | 2 |
| BCN25 | 4.57 | p.G1861R | NM_001127208 | TET2 | CCDS47120.1 | 9 |
| BCN5 | 4.98 | p.G1860fs | NM_001127208 | TET2 | CCDS47120.1 | 9 |

TABLE 9-continued

| Non synonymous candidate variants in PTCL mutated genes identified by RNAseq | | | | | | |
|---|---|---|---|---|---|---|
| BCN7 | 15.95 | p.C2362W | NM_033044 | MACF1 | CCDS435.1 | 47 |
| BCN1 | 5.18 | p.I122F | NM_001127207 | SMARCAL1 | CCDS2403.1 | 1 |
| BCN23 | 11.83 | p.R427K | NM_030627 | CPE84 | CCDS4390.1 | 4 |
| BCN18 | 9.87 | p.R430H | NM_001193357 | NUP62 | CCDS12788.1 | 1 |
| BCN2 | 7.71 | p.D286N | NM_001009991 | SYTL3 | CCDS34563.1 | 8 |
| BCN17 | 9.94 | p.G409D | NM_030952 | NUAK2 | CCDS1453.1 | 7 |
| BCN8 | 12.69 | p.F885fs | NM_013451 | MYOF | CCDS41550.1 | 25 |
| BCN24 | 3.48 | p.E45fs | NM_000052 | ATP7A | CCDS35339.1 | 2 |
| BCN16 | 4.37 | p.A1032T | NM_001409 | MEGF6 | CCDS41237.1 | 24 |
| BCN25 | 441.97 | p.G17V | NM_001664 | RHOA | CCDS2795.1 | 1 |
| BCN15 | 8.94 | p.A1276fs | NM_033044 | MACF1 | CCDS436.1 | 1 |
| BCN10 | 3.34 | p.H171fs | NM_006359 | SLC9A6 | CCDS14654.1 | 4 |
| BCN35 | 19.43 | p.T282fs | NM_001193357 | NUP62 | CCDS12788.1 | 1 |
| BCN14 | 4.08 | p.R1465X | NM_001127208 | TET2 | CCDS47120.1 | 8 |
| BCN17 | 10.1 | p.K323R | NM_018202 | TMEM57 | CCDS30638.1 | 6 |
| BCN4 | 15.37 | p.F1167Y | NM_001409 | MEGF6 | CCDS41237.1 | 28 |
| BCN13 | 4.87 | p.P714fs | NM_001145845 | ROBO1 | CCDS46872.1 | 14 |
| BCN14 | 5.01 | p.A540A | NM_004646 | NPHS1 | CCDS32996.1 | 12 |
| BCN35 | 18.25 | p.P838P | NM_005215 | DCC | CCDS11952.1 | 17 |
| BCN18 | 5.06 | p.Y515Y | NM_004444 | EPHB4 | CCDS5706.1 | 8 |
| BCN17 | 13.73 | p.P130P | NM_013451 | MYOF | CCDS41550.1 | 5 |
| BCN13 | 4.87 | p.T570T | NM_001145845 | ROBO1 | CCDS46872.1 | 12 |
| BCN16 | 12.84 | p.I1681 | NM_015679 | TRUB2 | CCDS6897.1 | 6 |
| BCN15 | 9.44 | p.A4612A | NM_012090 | MACF1 | CCDS435.1 | 78 |
| BCN11 | 22.41 | p.A2A | NM_006715 | MAN2C1 | CCDS32298.1 | 1 |
| BCN13 | 15.25 | p.A520A | NM_052905 | FMNL2 | CCDS46429.1 | 14 |
| BCN27 | 15.28 | p.S1194S | NM_015001 | SPEN | CCDS164.1 | 11 |
| BCN16 | 5.33 | p.P130P | NM_013451 | MYOF | CCDS41550.1 | 5 |
| BCN13 | 7.66 | p.P25P | NM_001040436 | YARS2 | CCDS31770.1 | 1 |

TABLE 10

| Primer sequences | | | | | | | |
|---|---|---|---|---|---|---|---|
| Gene/ Chr | SEQ ID NO | Forward Primer | SEQ ID NO | Reverse primer | Chr | From | To |
| DNMT3A | 9 | ACAGGGCTCTCCCTCTCC | 10 | ATAATTCCTTCCCCAAAGCCCAG | chr2 | 25536728 | 25536922 |
| DNMT3A | 11 | CCCATCACTTCTGGTTTTCCAGT | 12 | GTGGCTTGGGCTGGGAG | chr2 | 25497746 | 25497934 |
| DNMT3A | 13 | ATGGAGAGAGGAGAGCAGGAC | 14 | GCATCCCCCACTGTGGCTA | chr2 | 25470820 | 25471001 |
| DNMT3A | 15 | GCCTCACCTCCCTTTTCCAG | 16 | ACCCTAATGCCCTAATGTCTGTC | chr2 | 25497803 | 25497991 |

TABLE 10-continued

Primer sequences

| Gene/ Chr | SEQ ID NO | Forward Primer | SEQ ID NO | Reverse primer | Chr | From | To |
|---|---|---|---|---|---|---|---|
| DNMT3A | 17 | CGTGTGTGTTGTGTGTGTGC | 18 | GCTGGGATCCACCTCTGG | chr2 | 25522958 | 25523157 |
| DNMT3A | 19 | TTAGGGCCAGAAGGCTGGAAG | 20 | CTGTCCTGACAACCCCAACC | chr2 | 25469509 | 25469684 |
| DNMT3A | 21 | CTCGTACTCTGGCTCGTCATCG | 22 | GCAGGAATGAATGCTGTGGAAGA | chr2 | 25470906 | 25471097 |
| DNMT3A | 23 | CAGCCCTGGTGTGGATCTG | 24 | GATGAGAGTGACACTGCCAAGG | chr2 | 25469427 | 25469597 |
| DNMT3A | 25 | ATTAGCGAAGAACATCTGGAGCC | 26 | CTCCTCTGCTCACTGGGTCT | chr2 | 25467042 | 25467235 |
| DNMT3A | 27 | CAGCCATTTTCCACTGCTCTTG | 28 | TGATCTCCAAGTCCCCATCCAT | chr2 | 25505351 | 25505546 |
| DNMT3A | 29 | CTGGAGAGCCAAGTCCCTGA | 30 | CCAGCAGAGGGAGAGGGT | chr2 | 25505234 | 25505415 |
| DNMT3A | 31 | CCAGCTAAGGAGACCACTGGAG | 32 | CCTGGTGGTTTCTGACCCTTC | chr2 | 25467371 | 25467556 |
| DNMT3A | 33 | AGATGTCCCTCTTGTCACTAACG | 34 | CACACCACTGTCCTATGCAGAC | chr2 | 25463185 | 25463377 |
| DNMT3A | 35 | CAGGGCAGAAATATCCAAGGAGG | 36 | GCCCATCACGTTGCCTTTATC | chr2 | 25463430 | 25463627 |
| DNMT3A | 37 | CTCTGCAAGGGGAGGAGAGC | 38 | CAGCTGCCTACGCACCAC | chr2 | 25468932 | 25469124 |
| DNMT3A | 39 | TGGACATACATGCTTCTGTGTGA | 40 | GGAGATGGCTCCAAGTAACGG | chr2 | 25464422 | 25464619 |
| DNMT3A | 41 | TACCACTGAGAATTTGCCGTCTC | 42 | GTGTAATGATTTCTGCTCCTTGGG | chr2 | 25470457 | 25470649 |
| DNMT3A | 43 | TTCCTAAGTGCCTCTGCTACTCT | 44 | AGGAGGCCTGCATCCGAG | chr2 | 25468818 | 25468996 |
| DNMT3A | 45 | GTGGACACAGTCAGCCAGAAG | 46 | GGTACTCACCCCATCCCCTC | chr2 | 25468051 | 25468235 |
| DNMT3A | 47 | ACTTCCAGGCCTCCTAGTG | 48 | GCTTGTCCCCCCAGGT | chr2 | 25469861 | 25470041 |
| DNMT3A | 49 | AACAAAATGAAAGGAGGCAAGGG | 50 | CTCGGAGGTGTGTGAGGACT | chr2 | 25464344 | 25464527 |
| DNMT3A | 51 | CTCAGGCCCCACAACCAA | 52 | ATTAAGGAAGACCCCTGGAACTG | chr2 | 25466959 | 25467149 |
| DNMT3A | 53 | GGTGGAACGCACTGCAAAA | 54 | TATCACTGTATCTGGTCCCCTCC | chr2 | 25469976 | 25470158 |
| DNMT3A | 55 | CAGGGCTCCCCTCCTCTG | 56 | ACCCTCCTCTTGTGTATCTTTCT | chr2 | 25505439 | 25505614 |
| DNMT3A | 57 | GGATCAAGAACCTTCCCCCAC | 58 | GGAAACTGCGGGGCTTCTC | chr2 | 25470409 | 25470581 |
| DNMT3A | 59 | CATTTCGTTTTGCCAGAGTTGCC | 60 | CATCTGACCTGTTGTGCTCACT | chr2 | 25466680 | 25466879 |
| DNMT3A | 61 | CTCATCCTGCCCTTCCTTCTC | 62 | CGCTGTTATCCAGGTTTCTGTTG | chr2 | 25459746 | 25459922 |
| DNMT3A | 63 | CCACAGAGGGATGTGTAAAGAAGG | 64 | GAACTGGTCCCTTTGTTCTTCCC | chr2 | 25498248 | 25498444 |
| DNMT3A | 65 | TGTGCGCTCATCAATAATCTCCT | 66 | CTGTCAGCCTGTAACTGACCTTG | chr2 | 25469033 | 25469222 |
| DNMT3A | 67 | CTCAGGGGCTTCCCCACTAT | 68 | TCATCTTCAAACCGTCTCCTGTT | chr2 | 25461920 | 25462113 |
| DNMT3A | 69 | GATGAAGCAGCAGTCCAAGGTA | 70 | TCTTTGAGTTCTACCGCCTCCT | chr2 | 25463106 | 25463301 |
| DNMT3A | 71 | ATGTCCCTTACACACACGCAAAA | 72 | CTGCCCTCTCTGCCTTTTCTC | chr2 | 25457141 | 25457316 |
| DNMT3A | 73 | GATGCGGGGTCAGTGGG | 74 | CCTTGCTAATTCCTGGAGAGGTC | chr2 | 25470997 | 25471174 |
| DNMT3A | 75 | TGGAAAACAAGTCAGGTGGGAAA | 76 | AACTCCATAAAGCAGGGCAAAGA | chr2 | 25458478 | 25458661 |
| DNMT3A | 77 | CTCCATCCTCATGTTCTTGGTGT | 78 | AGGCAGAGACTGCTGGG | chr2 | 25457054 | 25457234 |
| DNMT3A | 79 | TACCTTTCCATTTCAGTGCACCA | 80 | GCATATTTGGTAGACGCATGACC | chr2 | 25458573 | 25458772 |
| FYN | 81 | CAGGAAGCTCTGCAAGTACTCAA | 82 | CACTCTCACTGCGCTTGTCTT | chr6 | 111982996 | 111983176 |
| FYN | 83 | GTCCCCGTATGAGACGAAGAGTT | 84 | AGAAGCAACAAAACTGACGGAGG | chr6 | 112041031 | 112041228 |
| FYN | 85 | CTGCGTGGAAGTTGTTGTAGTTG | 86 | CCCTTTTTTGTCTTTGGCAGGAA | chr6 | 112041089 | 112041285 |
| FYN | 87 | CTTACCTGGGTATGGCACTCTTC | 88 | CCCTCTGCCTGATGAATAACCAA | chr6 | 111995697 | 111995871 |
| FYN | 89 | ACTTCCATTTCTCTCCCCTAAACA | 90 | CAATGTCCCCCGAATCATTCCTT | chr6 | 112017409 | 112017608 |

TABLE 10-continued

| Primer sequences | | | | | | | |
|---|---|---|---|---|---|---|---|
| Gene/ Chr | SEQ ID NO | Forward Primer | SEQ ID NO | Reverse primer | Chr | From | To |
| FYN | 91 | GCTGGCTACGGAATTGAAAGCTA | 92 | ATGATCCACTGCTGGAAAAAGGA | chr6 | 111982864 | 111983061 |
| FYN | 93 | ATTGCCAAAAGATTTAAGGGTGG | 94 | CTCCATCCCCAACTACAACAACT | chr6 | 112040947 | 112041120 |
| FYN | 95 | GCCCATTTCCCAGTCTCTTGAT | 96 | ACATGTGTTCTGCTCTTCTCTCC | chr6 | 112021328 | 112021522 |
| FYN | 97 | GAGGATGGGGCTTAGAAAGCAAA | 98 | GTACGGGAGGTTCACAATCAAGT | chr6 | 111995604 | 111995790 |
| FYN | 99 | TCTTCTATCAATCGGGCCAATCC | 100 | CGTGTCTAAGTACATTGGGTCGT | chr6 | 112015601 | 112015788 |
| FYN | 101 | ACCAGAAATGCAAGACCCCTTC | 102 | TCTCCCTTCTTGTGAATTTCGTT | chr6 | 112035483 | 112035676 |
| FYN | 103 | TTTCTGAAGGAAGGGAAGGGAAG | 104 | GCGATCAGCAAACATTCTAGTGG | chr6 | 112015480 | 112015678 |
| FYN | 105 | CCTTCCATCTTTGGTGTTTGGGA | 106 | GGCTTACCGATCTGTCTGTCAAAA | chr6 | 112021236 | 112021414 |
| FYN | 107 | AGCCTTTCATCCCCTCTGACTAA | 108 | GGTGGTACTTTGGAAAACTTGGC | chr6 | 112025132 | 112025306 |
| FYN | 109 | ATGTAGATGGGCTCCTCAGACAC | 110 | TGGTTTGACTTCATATTCTGGGATG | chr6 | 112017503 | 112017691 |
| FYN | 111 | GTCAACTGGAGCCACATAATTGC | 112 | GTGGCAGGATGATTAGGTGACAG | chr6 | 112029142 | 112029328 |
| FYN | 113 | TACCTTTGGTGGTTTCACTCTCG | 114 | AGAGGGGAATTCATGGGCAAAAA | chr6 | 112025199 | 112025398 |
| FYN | 115 | ACTTTCCTGCTCTGGGCCTAT | 116 | TGGGATGATATGAAAGGAGACCAT | chr6 | 112024016 | 112024211 |
| FYN | 117 | GCCCAATGCTGATGGCATTTTATT | 118 | TTTACAGGGAAGGAGATTGGTGG | chr6 | 112029047 | 112029230 |
| FYN | 119 | CTGCTGAAGTGTTTCAAACTGGG | 120 | ATGAGGCCTAAAAAGCAAGCTGA | chr6 | 112024107 | 112024304 |
| FYN | 121 | ACCCAATGTACTTAGACACGTCA | 122 | AGCTCTCTGTTGGGAATTATCTTTCA | chr6 | 112015769 | 112015968 |
| IDH1 | 123 | CCTTGCTTAATGGGTGTAGATACCA | 124 | GGCTTGTGAGTGGATGGGTAAAA | chr2 | 209112978 | 209113151 |
| IDH2 | 125 | TGTACTGCAGAGACAAGAGGATG | 126 | GGAGCCCATCATCTGCAAAAAC | chr15 | 90631731 | 90631906 |
| IDH2 | 127 | GGACTAGGCGTGGGATGTTTTT | 128 | GTGTTGTTGCTTGGGGTTCAAAT | chr15 | 90631869 | 90632056 |
| RHOA | 129 | GCTCCCCAAACCTCCAAACT | 130 | AAACATCCCAGAAAAGTGGACCC | chr3 | 49399859 | 49400058 |
| RHOA | 131 | CATGTCTGCTTTTCAGCCACTTG | 132 | CTGGGCAGGAAGATTATGATCGC | chr3 | 49405770 | 49405956 |
| RHOA | 133 | TCTGCCACATAGTTCTCAAACAC | 134 | TGACTTCTTGTGCATTGCAGGTA | chr3 | 49412889 | 49413069 |
| RHOA | 135 | CAGGCAGTGACAAATATCAGGGT | 136 | CCTTGCACTCTTGTGGTTGTTTT | chr3 | 49405824 | 49406015 |
| RHOA | 137 | GTTTCACAAGACAAGGCACCCAG | 138 | GTGAAACCTGAAGAAGGCAGAGA | chr3 | 49397639 | 49397809 |
| RHOA | 139 | TGAAAAAGGCCAGTAATCATACACT AA | 140 | TGGAGTGTTCAGCAAAGACCAAA | chr3 | 49397558 | 49397754 |
| RHOA | 141 | CTAGCTCCCGCCTTGTGTG | 142 | TGCAATTTCACTGAGGTTCTTGG | chr3 | 49399943 | 49400138 |
| RHOA | 143 | AGCTCTAATTCTCTACATGCTCCA | 144 | TGGAAAGACATGCTTGCTCATAGT | chr3 | 49412791 | 49412975 |
| RHOA | 145 | ACCTCTCTCACTCCATCTTTGGT | 146 | aaTCTTTTAGATGAATTTGAATACTT TTTACTTACT | chr3 | 49397715 | 49397902 |
| RHOA | 147 | GAACACTCCATGTACCCAAAAGC | 148 | GACCGACGAGCAAAACTGTCTC | chr3 | 49397745 | 49397939 |
| TET2 | 149 | GTCCACTCTTATGGCACCAACAT | 150 | TGCAGTGGTTTCAACAATTAAGAGG | chr4 | 106182948 | 106183139 |
| TET2 | 151 | CTCACTAGCCTTCATAAAATAATCA TCAA | 152 | CTCTGTCTGAGGGTGATGTG | chr4 | 106196133 | 106196332 |
| TET2 | 153 | AACTTTTGCGACTTTCAGGACCA | 154 | CTAACTGGATTGGGCCGTCTCAT | chr4 | 106196205 | 106196397 |
| TET2 | 155 | GCAGTGAAGAGAAGCTACTGTGTT | 156 | TTACTCTTCATTCAAGGCACACC | chr4 | 106164743 | 106164939 |
| TET2 | 157 | TTGTTTTGTTTTGGTTGGGGTGG | 158 | CGAGTAGAGTTTGTCAGCCAGAG | chr4 | 106164671 | 106164870 |
| TET2 | 159 | ACAAACTCTACTCGGAGCTTACC | 160 | AAAGTGCACGCTGAACTCTCTTC | chr4 | 106164857 | 106165027 |
| TET2 | 161 | ATGCTAATGGTCAGGAAAAGCAG | 162 | TTTAAAGGGGTTGTGGCATGCAG | chr4 | 106197129 | 106197327 |

TABLE 10-continued

| Gene/ Chr | SEQ ID NO | Forward Primer | SEQ ID NO | Reverse primer | Chr | From | To |
|---|---|---|---|---|---|---|---|
| TET2 | 163 | GAGGACAACGATGAGGTCTGGT | 164 | TGCTGGTAAAAGACGAGGGAGAT | chr4 | 106197188 | 106197378 |
| TET2 | 165 | ATATGAACACAGAGCACCAGAGT | 166 | CTAAGCTGTCCTCAGCCCAA | chr4 | 106190772 | 106190929 |
| TET2 | 167 | TCGAGAATTTGGAGGAAAACCTG | 168 | GTCTTGACTGGCTCTGCTAACAT | chr4 | 106193747 | 106193926 |
| TET2 | 169 | CCCTTACCCTGGGCTTTTGAAT | 170 | ACCTTGGCTGGTAAAGTGTATGG | chr4 | 106196515 | 106196714 |
| TET2 | 171 | GCTTACTTCAAGCAAAGCTCAGT | 172 | AGTGTTGTGTTACTTTGGTTGGG | chr4 | 106156234 | 106156433 |
| TET2 | 173 | TCAGGAGGAGAAAAAACGGAGTG | 174 | TGGGGCTGACTTTTCCTTTTCAT | chr4 | 106193840 | 106194026 |
| TET2 | 175 | CATGCTTTCCCACACAGCTAATG | 176 | CTGACCAGACCTCATCGTTGTC | chr4 | 106197031 | 106197212 |
| TET2 | 177 | CCATTCCTGATACCATCACCTCC | 178 | ACTCACACGACTATTCTGGCTTC | chr4 | 106155145 | 106155324 |
| TET2 | 179 | GAGACAAGGAGCAAACACGAGAT | 180 | TCCAGTGTATTGTTTGGAGGTCA | chr4 | 106156730 | 106156920 |
| TET2 | 181 | ACACACACACACGTTTTCTTTGG | 182 | CTTCCACACTCCCAAACTCATCC | chr4 | 106193658 | 106193838 |
| TET2 | 183 | TCAGCTGCACAGCCTATATAATG | 184 | ACTTCCTTGGGATCTTGCTTCTG | chr4 | 106180715 | 106180897 |
| TET2 | 185 | TCAGCAGTTGTACCATTAGACCAAA | 186 | GGAGCTGCACTGTAGTTATGGAT | chr4 | 106196784 | 106196976 |
| TET2 | 187 | AAAATGGCTGAAAAAGCCCGTGA | 188 | GTCACGGACATGGTCCTTTCG | chr4 | 106197425 | 106197603 |
| TET2 | 189 | TGAGCCACATGAAACTTCAGAGC | 190 | ACAGGTTGGTTGTGGTCTTTTCA | chr4 | 106197529 | 106197728 |
| TET2 | 191 | TCTAACTCTGAGCTGCCTCCAAA | 192 | GCTTTGTGGTTCCCTGGATGTTA | chr4 | 106155937 | 106156135 |
| TET2 | 193 | TGAGGCATCACTGCCATCAATTC | 194 | TTGGGACTGCCCTTGATTCATTT | chr4 | 106156845 | 106157031 |
| TET2 | 195 | CAGGTTCCTCAGCTTCCTTCAG | 196 | TTTCAGAAAGCATCGGAGAAGGG | chr4 | 106156339 | 106156534 |
| TET2 | 197 | CCATGCAAATGTTTTTCCTGTGC | 198 | TTAATTGGCCTGTGCATCTGACT | chr4 | 106157868 | 106158044 |
| TET2 | 199 | TGCTGCTCTAAGGTGGCAT | 200 | GCAGGTGGATTCTCTTGCTTAGTT | chr4 | 106157946 | 106158140 |
| TET2 | 201 | AAATGCCATTAACAGTCAGGCTA | 202 | AGGTATTTAGCATTGCAGCTAGTTT | chr4 | 106155846 | 106156039 |
| TET2 | 203 | GCTTTCAAGAACAGGAGCAGAAG | 204 | CTTTTGAGTGTCCTTCTGGGGAG | chr4 | 106157744 | 106157943 |
| TET2 | 205 | GGAAGTGAAAATAGAGGGTAAACCT GA | 206 | TGAGGTGTTCTGACATTGGTCTT | chr4 | 106156440 | 106156636 |
| TET2 | 207 | CACATTTTAATTTTTGTTTCCATGC TCT | 208 | GGCAGTGGGCTTCCATTCT | chr4 | 106155022 | 106155221 |
| TET2 | 209 | AAGAATCCCAATAGGAATCACCC | 210 | TGGGATTTCTGAGGCACATAGTC | chr4 | 106197326 | 106197501 |
| TET2 | 211 | ACTTCATGGGAGCCACCTCTA | 212 | TGGGAAAGCATGTCATTCTCCTT | chr4 | 106196862 | 106197042 |
| TET2 | 213 | GGTTCCTATTCTCCCCAGTCTCA | 214 | TCTCCCTGCATATTTTGGTTTCC | chr4 | 106196606 | 106196778 |
| TET2 | 215 | CATTCACACACACTTTTATTTTTCA GATT | 216 | GCTGCCATTCTGCATGTTGTG | chr4 | 106190741 | 106190898 |
| TET2 | 217 | CACCTCAAGCATAACCCACCAAT | 218 | GATTCCGCTTGGTGAAAACGAG | chr4 | 106156630 | 106156829 |
| TET2 | 219 | CCCAAACTGAGTCTTGCCATAGT | 220 | TGGTCTCAATGATGCTCTTTTGC | chr4 | 106158002 | 106158181 |
| TET2 | 221 | AAGGCAAGCTTACACCCAGAAA | 222 | TGACTGCACATGAGCTTTTGGTA | chr4 | 106156947 | 106157124 |
| TET2 | 223 | CTACACATGTATGCAGCCCTTCT | 224 | AGTTGTCCTGTAGCTCTCCACT | chr4 | 106156496 | 106156684 |
| TET2 | 225 | AGTCACTGTGTGGCACTAGATTT | 226 | GAGGGAGATGTGAACTCTGGGAT | chr4 | 106157120 | 106157317 |
| TET2 | 227 | ATGCTGATGATGCTGATAATGCC | 228 | GCTTGCAAATTGCTGCTGGA | chr4 | 106155989 | 106156184 |
| TET2 | 229 | AGAAACCTGTGGTGCCTCCT | 230 | TGTCATATTGTTCACTTCATCTAAGC TA | chr4 | 106180806 | 106181005 |
| TET2 | 231 | AATCCACCTGCAAGCTGTGATAA | 232 | GTTCTGCAGCAGTGGTTTGTCTA | chr4 | 106158130 | 106158319 |

TABLE 10-continued

| Primer sequences | | | | | | | |
|---|---|---|---|---|---|---|---|
| Gene/ Chr | SEQ ID NO | Forward Primer | SEQ ID NO | Reverse primer | Chr | From | To |
| TET2 | 233 | TGTCAACTCTTATTCTGCTTCTGGA | 234 | GGGTAAGGGTTCATGGGATTAGAA | chr4 | 106196335 | 106196523 |
| TET2 | 235 | TCCATACACTTTACCAGCCAAGG | 236 | TAATCTAGAGGTGGCTCCCATGA | chr4 | 106196691 | 106196887 |
| TET2 | 237 | TATCTATGGAAGCACCAGCCCTA | 238 | CTGGGGAGAATAGGAACCCAGAT | chr4 | 106196428 | 106196623 |
| TET2 | 239 | CTCAAATCACAGAAGCAAGTAAAAG T | 240 | GTATCTAGTAATTTGGAAGGTGACTC TA | chr4 | 106158241 | 106158440 |
| TET2 | 241 | TTGTATGTGTGTGTGTTTCTGTGG | 242 | GCCCAAGATTTAAGACCAAAGGC | chr4 | 106163956 | 106164126 |
| TET2 | 243 | CGACAAAGGAAACTAGAAGCCAA | 244 | TTTAATATACCACACAACACATTTAT CTACA | chr4 | 106193931 | 106194127 |
| TET2 | 245 | GTACAGTGGACCAACATCTCCAG | 246 | GCCTGTTGATTCAAGTGCTGTTT | chr4 | 106157033 | 106157219 |
| TET2 | 247 | CCAAAAGGCTAATGGAGAAAGACG | 248 | CTCTGGATTTTCAGGCCCACT | chr4 | 106155444 | 106155633 |
| TET2 | 249 | AAAGCTAGCGTCTGGTGAAGAAT | 250 | AAGAAGCAATTGTGATGGTGGTG | chr4 | 106156131 | 106156317 |
| TET2 | 251 | AAACCAGCAACAGCAGCAAAAAT | 252 | CCAGTCCCATTTGGACATTATGAG | chr4 | 106157319 | 106157518 |
| TET2 | 253 | CAGTGGGCCTGAAAATCCAGAG | 254 | ACAATCTGGATAATATTGAGACAGTG TTTTT | chr4 | 106155612 | 106155810 |
| TET2 | 255 | TGCTAATGCCTAATGGTGCTACA | 256 | GGTGAGTGATCTCACAGGACAAC | chr4 | 106155713 | 106155898 |
| TET2 | 257 | AGCCAAGAAAGAAATCCAGGTGA | 258 | CACTTTTCCCCTCCTGCTCATT | chr4 | 106155481 | 106155667 |
| TET2 | 259 | AGACTACACATCCTGAACTTTTTGC | 260 | CGCAGCTTGTTGACCAGACATA | chr4 | 106157639 | 106157835 |
| TET2 | 261 | GCTCATCCAGAAGTAAATGGAGACA | 262 | TTGATCTGAAGGAGCCCAGAGAG | chr4 | 106155229 | 106155428 |
| TET2 | 263 | TGAGCCATTTTCAAACTCACACC | 264 | TCCTTCTCTTTGCTGATCATTGTTG | chr4 | 106157229 | 106157418 |
| TET2 | 265 | CACCCAATCTGAGCAATCCAAAC | 266 | ATCATGGTTAAGAGCTGGAAGCA | chr4 | 106196889 | 106197088 |
| TET2 | 267 | TAGAGGGTATTCCAAGTGTTTGC | 268 | AGACATTTGGTTGACTGCTTTCAC | chr4 | 106155345 | 106155523 |
| TET2 | 269 | TGTGTCATTCCATTTTGTTTCTGGA | 270 | CCTTCCTTCAGACCCAGACG | chr4 | 106190625 | 106190816 |
| TET2 | 271 | GGCCAGACTAAAGTGGAAGAATGT | 272 | TCTGAAACTAGGTGTGTATTGTTTGA | chr4 | 106157428 | 106157627 |
| TET2 | 273 | TGGGATTCAAAATGTAAGGGGAA | 274 | ATATGCATCAGGTGCAAGTTTCT | chr4 | 106182816 | 106182996 |
| TET2 | 275 | AGAGCAGCAAACAACTTCTTCAG | 276 | CGCCATGTGTCTCAGTACATTTCT | chr4 | 106158342 | 106158541 |
| TET2 | 277 | ATCGTAGAAATTCCCCTTATAGTCA G | 278 | AGATCTTGCTTTGGGATCACATT | chr4 | 106157537 | 106157732 |
| TET2 | 279 | GGTTAAGCTTTGTGGATGTAGCC | 280 | GTTAATCTGCCCTGTGCCTTTG | chr4 | 106162419 | 106162618 |
| TET3 | 281 | GCTGAGCCCCAGCAGAAAG | 282 | GCAAAAGCACCACAGAGACAG | chr2 | 74329169 | 74329367 |
| TET3 | 283 | GCCAGTGATTACATCCAGTCAGTA | 284 | GCTTGTGGTGGAGGTGCT | chr2 | 74274452 | 74274650 |
| TET3 | 285 | CCAGGAAGTGCAGGCTCAT | 286 | GGAAGAGGGCCAGTGGAG | chr2 | 74274955 | 74275146 |
| TET3 | 287 | CTGTGGGACCCCTTCAGC | 288 | CACACTCGATGAGGATGGAGC | chr2 | 74328719 | 74328917 |
| TET3 | 289 | CCCCTTCCCACTTCACAGATG | 290 | CAGGGCCGAGTTGAAATCCC | chr2 | 74328357 | 74328553 |
| TET3 | 291 | CAAGAACCTCAACCAGCCCAA | 292 | CGACCCCCTTCTTCTCTTTCTG | chr2 | 74329003 | 74329202 |
| TET3 | 293 | CTTCCCCCGCGAGGTC | 294 | GCACCCTCCCCCCACA | chr2 | 74326567 | 74326758 |
| TET3 | 295 | ATGCAGAGGAGCACGGGTA | 296 | CTCCGAGGCTACGGGGAAT | chr2 | 74314902 | 74315086 |
| TET3 | 297 | CGCTTAAGAAGCCCAACCG | 298 | CTTCTTCCCGTAGAGCTTGGC | chr2 | 74328945 | 74329144 |
| TET3 | 299 | ATGAGTTTGGTAGCGAGGAGAAC | 300 | GCTCAGCTTCTCCTTCTGAATCTT | chr2 | 74326500 | 74326681 |
| TET3 | 301 | GTATGAAACCACCCAACTGCAA | 302 | AGAGATCTGGGGCACCTCTG | chr2 | 74273841 | 74274040 |

TABLE 10-continued

| Primer sequences | | | | | | | |
|---|---|---|---|---|---|---|---|
| Gene/ Chr | SEQ ID NO | Forward Primer | SEQ ID NO | Reverse primer | Chr | From | To |
| TET3 | 303 | CTGACACCCCTCCAGCAAC | 304 | GAGGAAGAGGGTGCCTCCA | chr2 | 74274360 | 74274537 |
| TET3 | 305 | CTCAGGGGTGCCGGTCAAT | 306 | CCCCATAAGAGGACACAGCTTC | chr2 | 74273497 | 74273687 |
| TET3 | 307 | GTCGGACAGTGAACACAACTTCC | 308 | TTGGGCTGGTTGAGGTTCTTG | chr2 | 74328832 | 74329023 |
| TET3 | 309 | CTTCCAGGGTGCAGGGTCT | 310 | GTGACATGTGGGCAGCAAAAG | chr2 | 74319964 | 74320155 |
| TET3 | 311 | CATGTCCCCCAAGAGGACTAAC | 312 | CCGTCCTCCAGAGTGGGAAG | chr2 | 74328244 | 74328436 |
| TET3 | 313 | TTTGGTCTGCCCCTGGGAT | 314 | TCCAGGAAGTTGTGTTCACTGTC | chr2 | 74328659 | 74328858 |
| TET3 | 315 | CAGGCAGCTTCCCACTCTG | 316 | CTTTCATGGGGTTCCACAGCTT | chr2 | 74328410 | 74328599 |
| TET3 | 317 | CCAGCAGGAGGCCAAGC | 318 | CTGTAGGGGCCAGTGACCTTC | chr2 | 74329114 | 74329290 |
| TET3 | 319 | GCAGCAGTGGCAGTTTTGAG | 320 | TTGGGAAGCAGATACTCCTTGGG | chr2 | 74327844 | 74328027 |
| TET3 | 321 | GCCCATTCAGATCAAGAAGTCCA | 322 | TAGGTGCAAATAGCGCAAGAGAA | chr2 | 74274859 | 74275052 |
| TET3 | 323 | TCTGTGGTCATGGAAGGAGGG | 324 | ATGGCGGTCTGCAAGCTG | chr2 | 74273918 | 74274117 |
| TET3 | 325 | GGCCACCACTGCCAGAAC | 326 | CTGGCCCTGAAGCCCTCT | chr2 | 74315014 | 74315192 |
| TET3 | 327 | GGGAACAACAGCAGGGGAC | 328 | TCCCCTCCTTCCATGACCA | chr2 | 74273741 | 74273940 |
| TET3 | 329 | CTCCTTCAGAGCCTTCTGCTCC | 330 | GGCCTGGACTTCTTGATCTGAAT | chr2 | 74274693 | 74274885 |
| TET3 | 331 | CCAAGGCAAAGACCCCAACA | 332 | CAGGCGAGAAAGGATGGGAG | chr2 | 74317039 | 74317221 |
| TET3 | 333 | AGGTCATGTGTTTTGGGTGCTC | 334 | CGCTACCAAACTCATCCGTGTT | chr2 | 74326315 | 74326514 |
| TET3 | 335 | ATCCTCGGAGCCCGACA | 336 | CTTCTTCTTCTCCTTGGGTGGTC | chr2 | 74274586 | 74274784 |
| TET3 | 337 | CCAGATCTCTCCCCAAGAGGG | 338 | GGTGACAAGGCCTCAGGAAG | chr2 | 74274031 | 74274213 |
| TET3 | 339 | TACTCCACTCAGTGTCCAGGG | 340 | TCCTGAGTACTGTCCCCAAAGG | chr2 | 74328036 | 74328235 |
| TET3 | 341 | CAAGTACGCTCTCCCGTCTTTTA | 342 | CTCGGCAAACTCAGCACCA | chr2 | 74327746 | 74327932 |
| TET3 | 343 | CTGAAAGGTAGTCCTGGGTTCC | 344 | CCACAGCTTCTCCTCTGACTTC | chr2 | 74328551 | 74328724 |
| TET3 | 345 | ATCAAGCAAGAGCCAGTAGACCC | 346 | CAGACGAGAACACACCCCAG | chr2 | 74328101 | 74328299 |
| TET3 | 347 | GAGCCGCAGAACCACTTCA | 348 | TAAAAGACGGGAGAGCGTACTTG | chr2 | 74327576 | 74327768 |
| TET3 | 349 | TTCCCCCTTCTCTCTCTCTTTAG | 350 | CTTTTGGTCTACCCGCCAAGG | chr2 | 74273382 | 74273581 |
| TET3 | 351 | AGGCTGTGGTGTTGTCTGC | 352 | CAGCACCGAGTAGCTCTCCA | chr2 | 74327470 | 74327644 |
| TET3 | 353 | CTCATCTTTTGCTCCTGATAGCTC | 354 | GCCGCTTGAATACTGACTGGATG | chr2 | 74274286 | 74274485 |
| TET3 | 355 | CAAGGCTGAGAACCCACTCAC | 356 | CTTTCTCTGCCCTTCCCTGATAC | chr2 | 74275399 | 74275575 |
| TET3 | 357 | CAGGCTGTTCCCACAGACG | 358 | CTACTGGCTCTTGCTTGATGGAT | chr2 | 74327942 | 74328119 |
| TET3 | 359 | ATACTGCTCGCCTGGAAGATG | 360 | CAGTGTGTCAAGGTCTTCGC | chr2 | 74273613 | 74273812 |
| TET3 | 361 | CACAGGTGACCAACGAGGAAATA | 362 | ACAGGTGGGGCTATGACAGG | chr2 | 74320651 | 74320825 |
| TET3 | 363 | AAGAAGAAGAAGCTCCCAACACC | 364 | GGATGAGCCTGCACTTCCTG | chr2 | 74274776 | 74274975 |
| TET3 | 365 | TAACATCCCTCCTTCCAAGACCT | 366 | GGGCACAGAAGTCCATGCAG | chr2 | 74320560 | 74320749 |
| TET3 | 367 | CTGCCCCCTACTCAGGAAATG | 368 | GGGAGACATGTTTGCTGGTTCT | chr2 | 74275073 | 74275272 |
| TET3 | 369 | CACCCTGACCAAGGAAGACAATC | 370 | CAGGCGTCGGACCTCG | chr2 | 74326408 | 74326591 |
| TET3 | 371 | CTTCTCATTCCACCCCCCAG | 372 | CCCAGGCTTCAGGGAACTCA | chr2 | 74274162 | 74274356 |
| TET3 | 373 | CGTTCCCCCAAGCAAATCAAG | 374 | GGGTGTGTCCAGGTACTTAAGAG | chr2 | 74275298 | 74275471 |
| TET3 | 375 | GGCAGTTTGAGGCTGAATTTGGA | 376 | TCCCTCCTCTGAATGGAAGCAG | chr2 | 74275179 | 74275378 |

TABLE 10-continued

| Primer sequences | | | | | | | | |
|---|---|---|---|---|---|---|---|---|
| Gene/ Chr | SEQ ID NO | Forward Primer | SEQ ID NO | Reverse primer | Chr | From | To |
| TET3 | 377 | ACTCCAGAACGAAGGGATATTGC | 378 | CGGAACTTGCGAGGTGTCTT | chr2 | 74316968 | 74317149 |
| TET3 | 379 | CGTGTACTCCTACCACTCCTACT | 380 | GTCTGGCTTCTTCTCAAAACTGC | chr2 | 74327683 | 74327875 |
| TET3 | 381 | AGTTGTTCTCCTTTGGGGTTCTG | 382 | TGAGTGGGCTCAACACTCAC | chr2 | 74307568 | 74307738 |
| TET3 | 383 | TTCCAAAAATGTTTACTCTCTGTGT T | 384 | AATGAGAGGCGCTTAATATCCGT | chr2 | 74300643 | 74300840 |
| TET3 | 385 | CCGGATCGAGAAGGTCATCTACA | 386 | ACCCACCTGGCCCCAC | chr2 | 74307649 | 74307847 |

REFERENCES

1. Armitage, J. O. The aggressive peripheral T-cell lymphomas: 2012 update on diagnosis, risk stratification, and management. *Am J Hematol* 87, 511-9 (2012).
2. Rudiger, T. et al. Peripheral T-cell lymphoma (excluding anaplastic large-cell lymphoma): results from the Non-Hodgkin's Lymphoma Classification Project. *Ann Oncol* 13, 140-9 (2002).
3. Schiller, M. R. Coupling receptor tyrosine kinases to Rho GTPases—GEFs what's the link. *Cell Signal* 18, 1834-43 (2006).
4. Bar-Sagi, D. & Hall, A. Ras and Rho GTPases: a family reunion. *Cell* 103, 227-38 (2000).
5. Vega, F. M. & Ridley, A. J. Rho GTPases in cancer cell biology. *FEBS Lett* 582, 2093-101 (2008).
6. Hanna, S. & El-Sibai, M. Signaling networks of Rho GTPases in cell motility. *Cell Signal* (2013).
7. Hall, A. Rho family GTPases. *Biochem Soc Trans* 40, 1378-82 (2012).
8. Longenecker, K. et al. Structure of a constitutively activated RhoA mutant (Q63L) at 1.55 A resolution. *Acta Crystallogr D Biol Crystallogr* 59, 876-80 (2003).
9. Mayer, T., Meyer, M., Janning, A., Schiedel, A. C. & Barnekow, A. A mutant form of the rho protein can restore stress fibers and adhesion plaques in v-src transformed fibroblasts. *Oncogene* 18, 2117-28 (1999).
10. Zhang, S. et al. Rho family GTPases regulate p38 mitogen-activated protein kinase through the downstream mediator Pak1. *J Biol Chem* 270, 23934-6 (1995).
11. Ghosh, P. M. et al. Role of RhoA activation in the growth and morphology of a murine prostate tumor cell line. *Oncogene* 18, 4120-30 (1999).
12. Pan, Z. K. et al. Role of the Rho GTPase in bradykinin-stimulated nuclear factor-kappaB activation and IL-1beta gene expression in cultured human epithelial cells. *J Immunol* 160, 3038-45 (1998).
13. Reid, T. et al. Rhotekin, a new putative target for Rho bearing homology to a serine/threonine kinase, PKN, and rhophilin in the rho-binding domain. *J Biol Chem* 271, 13556-60 (1996).
14. Garcia-Mata, R. et al. Analysis of activated GAPs and GEFs in cell lysates. *Methods Enzymol* 406, 425-37 (2006).
15. Couronne, L., Bastard, C. & Bernard, O. A. TET2 and DNMT3A mutations in human T-cell lymphoma. *N Engl J Med* 366, 95-6 (2012).
16. Quivoron, C. et al. TET2 inactivation results in pleiotropic hematopoietic abnormalities in mouse and is a recurrent event during human lymphomagenesis. *Cancer Cell* 20, 25-38 (2011).
17. Cairns, R. A. et al. IDH2 mutations are frequent in angioimmunoblastic T-cell lymphoma. *Blood* 119, 1901-3 (2012).
18. Palacios, E. H. & Weiss, A. Function of the Src-family kinases, Lck and Fyn, in T-cell development and activation. *Oncogene* 23, 7990-8000 (2004).
19. McCormack, P. L. & Keam, S. J. Dasatinib: a review of its use in the treatment of chronic myeloid leukaemia and Philadelphia chromosome-positive acute lymphoblastic leukaemia. *Drugs* 71, 1771-95 (2011).
20. Li, H. & Durbin, R. Fast and accurate long-read alignment with Burrows-Wheeler transform. *Bioinformatics* 26, 589-95 (2010).
21. Langmead, B. & Salzberg, S. L. Fast gapped-read alignment with Bowtie 2. *Nat Methods* 9, 357-9 (2012).
22. Schmitz, R. et al. Burkitt lymphoma pathogenesis and therapeutic targets from structural and functional genomics. *Nature* 490, 116-20 (2012).
23. Maher, C. A. et al. Chimeric transcript discovery by paired-end transcriptome sequencing. *Proc Natl Acad Sci USA* 106, 12353-8 (2009).
24. McPherson, A. et al. deFuse: an algorithm for gene fusion discovery in tumor RNA-Seq data. *PLoS Comput Biol* 7, e1001138 (2011).
25. Pettersen, E. F. et al. UCSF Chimera—a visualization system for exploratory research and analysis. *J Comput Chem* 25, 1605-12 (2004).
26. Altschul, S. F. et al. Gapped BLAST and PSI-BLAST: a new generation of protein database search programs. *Nucleic Acids Res* 25, 3389-402 (1997).
27. Roy, A., Kucukural, A. & Zhang, Y. I-TASSER: a unified platform for automated protein structure and function prediction. *Nat Protoc* 5, 725-38 (2010).
28. Subauste, M. C. et al. Rho family proteins modulate rapid apoptosis induced by cytotoxic T lymphocytes and Fas. *J Biol Chem* 275, 9725-33 (2000).
29. Mariotti, A. et al. EGF-R signaling through Fyn kinase disrupts the function of integrin alpha6beta4 at hemidesmosomes: role in epithelial cell migration and carcinoma invasion. *J Cell Biol* 155, 447-58 (2001).
30. Kamanova, J. et al. Adenylate cyclase toxin subverts phagocyte function by RhoA inhibition and unproductive ruffling. *J Immunol* 181, 5587-97 (2008).

31. Pallotta, M. T. et al. Indoleamine 2,3-dioxygenase is a signaling protein in long-term tolerance by dendritic cells. *Nat Immunol* 12, 870-8 (2011).
32. Harr, M. W. et al. Inhibition of Lck enhances glucocorticoid sensitivity and apoptosis in lymphoid cell lines and in chronic lymphocytic leukemia. *Cell Death Differ* 17, 1381-91 (2010).
33. Widmann, C., Gerwins, P., Johnson, N. L., Jarpe, M. B. & Johnson, G. L. MEK kinase 1, a substrate for DEVD-directed caspases, is involved in genotoxin-induced apoptosis. *Mol Cell Biol* 18, 2416-29 (1998).
34. Schenk, S. et al. Sirt1 enhances skeletal muscle insulin sensitivity in mice during caloric restriction. *J Clin Invest* 121, 4281-8 (2011).
35. Wang, Q. et al. Thrombin and lysophosphatidic acid receptors utilize distinct rhoGEFs in prostate cancer cells. *J Biol Chem* 279, 28831-4 (2004).

What is claimed is:

1. A method, comprising (a) providing a biological sample from a subject that has lymphoma;

(b) analyzing the biological sample to detect for presence of RHOA p.Glyl7Val mutation, (c) determining that the subject has Peripheral T-Cell Lymphoma if RHOA p.Glyl7Val mutation, is detected in the biological sample and (d) if it is determined that the subject has an increased risk of developing Peripheral T-Cell Lymphoma due to the presence of a mutation selected from the group consisting of FYN p.Leu174Arg, FYN p.Arg176Cys, and FYN p.Tyr531His, then prophylactically treating the subject for Peripheral T-Cell Lymphoma by administering a therapeutically effective amount of an SRC kinase inhibitor.

2. The method of claim 1, wherein the biological sample is selected from the group consisting of lymphoma tumor, bone marrow, serum, blood, cerebrospinal fluid and plasma.

3. The method of claim 1, wherein the subject is human.

4. The method of claim 1, wherein the SRC kinase inhibitor is selected from the group consisting of Bosutinib (SKI-606); Saracatinib (AZD0530); Dasatinib (BMS354825); KX2-391; XL-228, JNJ-26483327, A 419259 trihydrochloride; AZM 475271; Damnacanthal, Herbimycin A, Lavendustin A, MNS, 1-Naphthyl PP1 D 166285 dihydrochloride, PP 1, PP 2, SRC I1, KX2-391 (KX01); and NVP-BHG712.

5. The method of claim 1, further comprising:

(e) if it is determined that subject has Peripheral T-Cell Lymphoma and if the RHOA p.Glyl7Val mutation is present then determining that the Peripheral T-Cell Lymphoma has a 70% change of being angioimmunoblastic T-cell lymphoma.

* * * * *